(12) United States Patent
Nakayama et al.

(10) Patent No.: US 7,459,291 B2
(45) Date of Patent: Dec. 2, 2008

(54) CHORDIN-LIKE MOLECULES AND USES THEREOF

(75) Inventors: Naoki Nakayama, Thousand Oaks, CA (US); Duanzhi Wen, Thousand Oaks, CA (US); Chun-ya Han, Thousand Oaks, CA (US); Ching He, Newbury Park, CA (US); Dongyin Yu, Simi Valley, CA (US)

(73) Assignee: Amgen Inc., Thousand Oaks, CA (US)

( * ) Notice: Subject to any disclaimer, the term of this patent is extended or adjusted under 35 U.S.C. 154(b) by 335 days.

(21) Appl. No.: 11/145,198

(22) Filed: Jun. 3, 2005

(65) Prior Publication Data

US 2005/0214856 A1    Sep. 29, 2005

Related U.S. Application Data

(62) Division of application No. 09/724,915, filed on Nov. 28, 2000, now Pat. No. 7,018,810.

(60) Provisional application No. 60/169,494, filed on Dec. 7, 1999.

(51) Int. Cl.
| | |
|---|---|
| C12P 21/02 | (2006.01) |
| C12N 1/21 | (2006.01) |
| C12N 5/10 | (2006.01) |
| C12N 15/12 | (2006.01) |
| C12N 15/63 | (2006.01) |
| C12N 15/79 | (2006.01) |
| C12N 15/86 | (2006.01) |
| C07H 21/04 | (2006.01) |
| C07K 14/475 | (2006.01) |

(52) U.S. Cl. .............. 435/69.1; 435/252.3; 435/254.11; 435/320.1; 435/325; 536/23.5; 530/350

(58) Field of Classification Search ........................ None
See application file for complete search history.

(56) References Cited

U.S. PATENT DOCUMENTS

| | | | | |
|---|---|---|---|---|
| 4,179,337 | A | 12/1979 | Davis et al. | |
| 5,635,489 | A | 6/1997 | Haley | |
| 5,679,783 | A | 10/1997 | De Robertis et al. | 536/23.5 |
| 5,693,775 | A | 12/1997 | Nathans et al. | 536/23.1 |
| 5,986,056 | A | 11/1999 | LaVallie et al. | |
| 2002/0197666 | A1* | 12/2002 | Jacobs et al. | 435/69.1 |

FOREIGN PATENT DOCUMENTS

| | | |
|---|---|---|
| WO | WO 98/40483 | 9/1998 |
| WO | WO 99/31236 | 6/1999 |
| WO | WO 99/57132 | 11/1999 |
| WO | WO 00/09551 | 2/2000 |

OTHER PUBLICATIONS

Alberts et al., "Molecular Biology of the Cell," Garland Publishing, Inc., p. 5-7, 1994.

Bowie et al., "Deciphering the message in protein sequences: tolerance to amino acid substitutions," Science 247 (4948): 1306-10, Mar. 16, 1990.

Celeste et al., "Identification of Transforming Growth Factor Beta Family Members Present in Bone-Inductive Protein Purified from Bovine Bone," Proc. Nat. Acad. Sci. USA 87:9843-47, 1990.

Hogan, "Bone Morphogenetic Proteins: Multifunctional Regulators of Vertebrate Development", Genes Dev. 10:1580-94, 1996.

Jones et al., "Signalling by TGF-Beta Family Members: Short-Range Effects of Xnr-2 and BMP-4 Contrast with the Long-Range Effects of Activin," Curr. Biol. 6:1468-75, 1996.

Jones et al., "Establishment of a BMP-4 Morphogen Gradient by Long-Range Inhibition," Dev. Biol. 194:12-17, 1998.

Nakayama Naoki et al., "A Novel chordin-like protein inhibitor for bone morphongenetic proteins expressed preferentially in mesenchymal cell lineages," Dev Biol 232:372-387, 2001.

NCI-CGAP. National Cancer Institute, Cancer Genome Anatomy Project (CGAP), Tumor Gene Index. GenBank Database Accession No. AI246227, National Center for Biotechnology Information, Bethesda, MD. Jan. 28, 1999.

Ngo et al., The Protein Folding Problem and Tertiary Structure Prediction, Merz and Le Grans (Eds), Springer Verlag, pp. 433 and 492-495, Aug. 1994.

Pappano et al., "Coding Sequence and Expression Patterns of Mouse Chordin and Mapping of the Cognate Mouse chrd and Human CHRD Genes," Genomics 52:236-39, 1998.

Piccolo et al., "Dorsoventral Patterning in Xenopus: Inhibition of Ventral Signals by Direct Binding of Chordin to BMP-4," Cell 86:589-98, 1996.

The I.M.A.G.E. Consortium [online], [retrieved on Nov. 7, 2002]. Retrieved from the internet:<URL:http://image.IInl.gov/image/html/phage.shtml>.

Wozney et al., "Novel Regulators of Bone Formation: Molecular Clones and Activities," Science 242:1528-34, 1988.

Brandon C. Improved immunocytochemical staining through the use of Fab fragments of primary antibody, Fab-specific second antibody, and Fab-horseradish peroxidase. J Histochem Cytochem. Jul. 1985; 33(7):715-719.

Larrain et al. BMP-binding modules in chordin: a model for signalling regulation in the extracellular space. Development. Feb. 2000; 127(4):821-830.

* cited by examiner

Primary Examiner—David S Romeo
(74) Attorney, Agent, or Firm—James E. Klaniecki

(57) ABSTRACT

The present invention provides Chordin-Like, (CHL) polypeptides and nucleic acid molecules encoding the same. The invention also provides selective binding agents, vectors, host cells, and methods for producing CHL polypeptides. The invention further provides pharmaceutical compositions and methods for the diagnosis, treatment, amelioration, and/or prevention of diseases, disorders, and conditions associated with CHL polypeptides.

12 Claims, 31 Drawing Sheets

FIG. 1A

```
ccacgcgtcc ggagcgcccc agggagctca gagcttgtgc aagcgtggca gcaggaggag  60
gccagtgccc agctttagtc caccgctcct ctccttggag ccctgaatt gcattttgca  120 gtagctcgaa ggagaaaaaa gtagaag atg gat ggc atg aaa tac atc att tcc  174
                              Met Asp Gly Met Lys Tyr Ile Ile Ser
                               1               5
```

| | | | | | | | | | | | | | | | | |
|---|---|---|---|---|---|---|---|---|---|---|---|---|---|---|---|---|
| tta | ttt | ttc | atc | ttt | gtt | ttc | cta | gaa | gga | agc | aaa | aca | gaa | caa | gta | 222 |
| Leu | Phe | Phe | Ile | Phe | Val | Phe | Leu | Glu | Gly | Ser | Lys | Thr | Glu | Gln | Val | |
| 10 | | | | 15 | | | | | 20 | | | | | | 25 | |
| aaa | cac | tca | gac | aca | tat | tgc | gtg | ttt | caa | gac | aag | aag | tat | aga | gtg | 270 |
| Lys | His | Ser | Asp | Thr | Tyr | Cys | Val | Phe | Gln | Asp | Lys | Lys | Tyr | Arg | Val | |
| | | | | 30 | | | | | 35 | | | | | 40 | | |
| ggt | gag | aaa | tgg | cat | ccc | tac | ctg | gaa | ccg | tat | gga | ctg | gtt | tac | tgt | 318 |
| Gly | Glu | Lys | Trp | His | Pro | Tyr | Leu | Glu | Pro | Tyr | Gly | Leu | Val | Tyr | Cys | |
| | | | | 45 | | | | | 50 | | | | | 55 | | |
| gtg | aac | tgc | atc | tgc | tct | gag | aat | ggg | aat | gtg | ctt | tgc | agc | cga | gtc | 366 |
| Val | Asn | Cys | Ile | Cys | Ser | Glu | Asn | Gly | Asn | Val | Leu | Cys | Ser | Arg | Val | |
| | | | 60 | | | | | 65 | | | | | 70 | | | |
| aga | tgt | cca | agt | ctt | cat | tgc | ctt | tca | ccc | gtg | cat | att | cct | cat | ctc | 414 |
| Arg | Cys | Pro | Ser | Leu | His | Cys | Leu | Ser | Pro | Val | His | Ile | Pro | His | Leu | |
| | 75 | | | | | 80 | | | | | 85 | | | | | |
| tgt | tgc | ccc | cgc | tgc | cca | gac | tcc | tta | cca | cca | gtg | aac | aat | aag | gtg | 462 |
| Cys | Cys | Pro | Arg | Cys | Pro | Asp | Ser | Leu | Pro | Pro | Val | Asn | Asn | Lys | Val | |
| 90 | | | | | 95 | | | | | 100 | | | | | 105 | |
| acc | agc | aag | tca | tgc | gaa | tac | aat | gga | acc | act | tac | caa | cat | gga | gaa | 510 |
| Thr | Ser | Lys | Ser | Cys | Glu | Tyr | Asn | Gly | Thr | Thr | Tyr | Gln | His | Gly | Glu | |
| | | | | 110 | | | | | 115 | | | | | 120 | | |
| ctg | ttc | ata | gct | gaa | ggg | ctc | ttt | cag | aac | cgg | caa | ccc | aat | cag | tgc | 558 |
| Leu | Phe | Ile | Ala | Glu | Gly | Leu | Phe | Gln | Asn | Arg | Gln | Pro | Asn | Gln | Cys | |
| | | | | 125 | | | | | 130 | | | | | 135 | | |
| agt | cag | tgt | agc | tgc | tcg | gag | ggg | aat | gta | tac | tgt | ggt | ctc | aag | act | 606 |
| Ser | Gln | Cys | Ser | Cys | Ser | Glu | Gly | Asn | Val | Tyr | Cys | Gly | Leu | Lys | Thr | |
| | | | 140 | | | | | 145 | | | | | 150 | | | |
| tgc | ccc | aaa | ctg | acc | tgt | gca | ttc | cca | gtc | tct | gtt | cca | gat | tct | tgc | 654 |
| Cys | Pro | Lys | Leu | Thr | Cys | Ala | Phe | Pro | Val | Ser | Val | Pro | Asp | Ser | Cys | |
| | | 155 | | | | | 160 | | | | | 165 | | | | |
| tgc | cga | gta | tgc | aga | ggg | gat | gca | gaa | tta | tcg | tgg | gaa | cat | gcg | gat | 702 |
| Cys | Arg | Val | Cys | Arg | Gly | Asp | Ala | Glu | Leu | Ser | Trp | Glu | His | Ala | Asp | |
| 170 | | | | 175 | | | | | 180 | | | | | 185 | | |

FIG. 1B

```
ggt gat atc ttc cgg caa cct gcc aac aga gaa gca aga cat tct tac    750
Gly Asp Ile Phe Arg Gln Pro Ala Asn Arg Glu Ala Arg His Ser Tyr
            190                 195                 200 ctc cgt tcc ccc tac gat cct cca cca aac aga caa gct gga ggt ctt    798
Leu Arg Ser Pro Tyr Asp Pro Pro Pro Asn Arg Gln Ala Gly Gly Leu
            205                 210                 215 ccc cgc ttt cct ggg agc aga agt cac cgg gga gct gtt ata gat tcc    846
Pro Arg Phe Pro Gly Ser Arg Ser His Arg Gly Ala Val Ile Asp Ser
            220                 225                 230 cag caa gca tcc ggg acc atc gtg cag att gtc atc aat aac aag cac    894
Gln Gln Ala Ser Gly Thr Ile Val Gln Ile Val Ile Asn Asn Lys His
    235                 240                 245 aaa cat gga caa gtg tgt gtt tcc aat gga aag acc tac tct cat gga    942
Lys His Gly Gln Val Cys Val Ser Asn Gly Lys Thr Tyr Ser His Gly
250                 255                 260                 265 gag tcc tgg cac cca aat cta cga gca ttt ggc att gtg gaa tgt gta    990
Glu Ser Trp His Pro Asn Leu Arg Ala Phe Gly Ile Val Glu Cys Val
                270                 275                 280 cta tgc act tgt aat gtc acc aag caa gaa tgt aag aaa atc cac tgc   1038
Leu Cys Thr Cys Asn Val Thr Lys Gln Glu Cys Lys Lys Ile His Cys
                285                 290                 295 ccc aat cga tac ccc tgc aag tat cct caa aaa ata gat gga aag tgc   1086
Pro Asn Arg Tyr Pro Cys Lys Tyr Pro Gln Lys Ile Asp Gly Lys Cys
            300                 305                 310 tgc aag gtg tgc cca ggt aaa aag gca aaa ggt gca ttg gct gga ggc   1134
Cys Lys Val Cys Pro Gly Lys Lys Ala Lys Gly Ala Leu Ala Gly Gly
    315                 320                 325 cct gcc ttt ggt tgaatgagat tcacacatag tcctattcag tcttctttgt       1186
Pro Ala Phe Gly
330 tcatcaaaac tataaatgac ctgtcttata gttctaacga taatagttct agcaagaatg 1246 aacttcatcc tttcgtcttc tgagacactg atggttgctt tgaaggaatt aactactcag 1306 agtttctttt gtctacaatg tcaaacacat gccaagttgc ttatcttgtt cttgcttttc 1366 taaattagag agtttacgtt atcactgttt tagaaaaagt cacacctttc atggtttaaa 1426 tcaccaactc acttcaagac ataatccagt actcttttca gatgagatat aaatgagtta 1486 cagtggagag aaattagatt ctgatccaaa tgcatcaaat ccacaagtat cttaccccat 1546 gtgaacattt taaagtttat tactgtgttc cacattgcta ttttaatttg caatttcttt 1606
```

FIG. 1C

```
ttaaatttc   tgagatattg  tatctgtata  tacttatggg  gtacagtatg  ttaattcaat  1666
acaaatatac  aaggtataat  tgtcaaatca  gggtaattat  cattctctct  cctctgattt  1726
tatccctaga  ctcttctagt  cattttaaaa  tttatcatca  attgggtttt  tgatatggta  1786
actccactgt  gctaaagaaa  ccattcattc  taatggcatt  ttaggatcta  ctatctaacc  1846
tctatctccc  cttctgtt                                                    1864
```

FIG. 2A

```
ccacgcgtcc gagcgcccca gggagctcag agcgtgtgca agcgtggcag aaggaagagg    60
ccagtgccca gctttagccc accagtccta ggagtctctg agctgcattt tgcagtagct   120
caaaggagaa gagagtggaa a atg gaa ggc ata aaa tat atc gcc tcc ttg    171
                        Met Glu Gly Ile Lys Tyr Ile Ala Ser Leu
                         1               5                    10 gtt ttc ttc ttt gtt ttc ctg gaa gca agc aaa aca gag cca gta aaa    219
Val Phe Phe Phe Val Phe Leu Glu Ala Ser Lys Thr Glu Pro Val Lys
                 15                  20                  25 cac tca gag aca tat tgc atg ttt caa gac aag aag tat aga gtt ggt    267
His Ser Glu Thr Tyr Cys Met Phe Gln Asp Lys Lys Tyr Arg Val Gly
             30                  35                  40 gag aaa tgg cat ccc tac ctg gaa cca tat gga ctg gtt tac tgt gtg    315
Glu Lys Trp His Pro Tyr Leu Glu Pro Tyr Gly Leu Val Tyr Cys Val
         45                  50                  55 aac tgc atc tgc tca gag aat ggg aat gtg ctt tgc agc cga gtc aga    363
Asn Cys Ile Cys Ser Glu Asn Gly Asn Val Leu Cys Ser Arg Val Arg
     60                  65                  70 tgt cca act ctt cat tgc ctt tca ccc gtg cat att cct cat ctg tgt    411
Cys Pro Thr Leu His Cys Leu Ser Pro Val His Ile Pro His Leu Cys
 75                  80                  85                  90 tgc ccc cgt tgc cca gac tcc tta cca ccg atg aac aat aag gtg acc    459
Cys Pro Arg Cys Pro Asp Ser Leu Pro Pro Met Asn Asn Lys Val Thr
                 95                 100                 105 agc aag tcc tgc gaa tac aat ggg acc acc tac caa cac gga gag ctc    507
Ser Lys Ser Cys Glu Tyr Asn Gly Thr Thr Tyr Gln His Gly Glu Leu
            110                 115                 120 ttc ata gct gaa ggg ctc ttt cag aac cgg cag ccc aat cag tgc agt    555
Phe Ile Ala Glu Gly Leu Phe Gln Asn Arg Gln Pro Asn Gln Cys Ser
        125                 130                 135 cag tgc agc tgc tcg gag ggg aat gtg tat tgt ggt ctc aag act tgc    603
Gln Cys Ser Cys Ser Glu Gly Asn Val Tyr Cys Gly Leu Lys Thr Cys
    140                 145                 150 ccc aaa ctg acc tgt gca ttc cca gtc tct gtt cca gat tcc tgc tgc    651
Pro Lys Leu Thr Cys Ala Phe Pro Val Ser Val Pro Asp Ser Cys Cys
155                 160                 165                 170 cga gta tgc aga ggg gat gga gaa tta tca tgg gaa cat tct gat gct    699
Arg Val Cys Arg Gly Asp Gly Glu Leu Ser Trp Glu His Ser Asp Ala
                175                 180                 185
```

FIG. 2B

```
gat atc ttc cgg caa cct gcc aac aga gaa gca aga cat tct tac ctc    747
Asp Ile Phe Arg Gln Pro Ala Asn Arg Glu Ala Arg His Ser Tyr Leu
        190                 195                 200 cgt tcc ccc tac gat cct cca cca agc aga caa gct gga ggt ctt cct    795
Arg Ser Pro Tyr Asp Pro Pro Pro Ser Arg Gln Ala Gly Gly Leu Pro
        205                 210                 215 cgc ttt gct ggg agc aga agt cac cgg gga gct gtc att gat tct cag    843
Arg Phe Ala Gly Ser Arg Ser His Arg Gly Ala Val Ile Asp Ser Gln
        220                 225                 230 caa gca tca ggg acc atc gtg cag atc gtc atc aat aac aag cac aaa    891
Gln Ala Ser Gly Thr Ile Val Gln Ile Val Ile Asn Asn Lys His Lys
235                 240                 245                 250 cat gga caa gtg tgt gtt tcc aat gga aag acc tat tct cac gga gaa    939
His Gly Gln Val Cys Val Ser Asn Gly Lys Thr Tyr Ser His Gly Glu
                    255                 260                 265 tcc tgg cat tca aat cta cga gct ttt ggc att gtg gaa tgt gtt cta    987
Ser Trp His Ser Asn Leu Arg Ala Phe Gly Ile Val Glu Cys Val Leu
                270                 275                 280 tgc act tgt aat gtc acc aag caa gaa tgt aag aaa atc cac tgc ccc   1035
Cys Thr Cys Asn Val Thr Lys Gln Glu Cys Lys Lys Ile His Cys Pro
            285                 290                 295 aat cga tac ccc tgc aag tat cct caa aaa tta gat gga aag tgc tgc   1083
Asn Arg Tyr Pro Cys Lys Tyr Pro Gln Lys Leu Asp Gly Lys Cys Cys
        300                 305                 310 aag gtg tgc cca gaa gaa cct cca agt caa aac ttt gac agc aaa ggt   1131
Lys Val Cys Pro Glu Glu Pro Pro Ser Gln Asn Phe Asp Ser Lys Gly
315                 320                 325                 330 tcc ttt tgt gga gaa gaa acc atg cct gta tat gag gct gtg ctc gtg   1179
Ser Phe Cys Gly Glu Glu Thr Met Pro Val Tyr Glu Ala Val Leu Val
                    335                 340                 345 gag gat gga gag aca gcc aga aaa gta gca ctg gag acc gag aaa cca   1227
Glu Asp Gly Glu Thr Ala Arg Lys Val Ala Leu Glu Thr Glu Lys Pro
                350                 355                 360 cct caa gta gta ggt tca cgt ttg gac tat tcg aaa ggg cat tct cca   1275
Pro Gln Val Val Gly Ser Arg Leu Asp Tyr Ser Lys Gly His Ser Pro
            365                 370                 375 gca ctt cca cat tgagaagatt tccaaggaga tgtttgggga gctccatcat       1327
Ala Leu Pro His
        380 ttcaagctgg tgactcgaac caccatgaac cagtggaaga tcttcgctga aggagaagct 1387
```

FIG. 2C

```
cagctcagcc agatgtgctc aagtcgggtg tgcagaacag aactggaaga tttggtccag  1447
gttttgtacc tggagagacc tgaaaaggac cactgttaga caaaacagtc aggattgaat  1507
agtatcaatc aaggaaaccc aagctgcagc tggactgccg gcttacttta cttaagtcaa  1567
cagtgctcca aaaccccaaa gtcaacctca gtcaaattat ccagtcacag cacaccttgt  1627
tcctctatgt gcagcggtgt gccagccctc aaacatctcc tgtaaagaga atagaggagt  1687
ctttaatggt ttctgggggt gggggggagaa gggataggac tttgtggtac agctctattt  1747
tctctgagaa tcacatttat ttgcaggtta aagtagaaaa gaaaaccact ttttagggat  1807
tctatgtaga aagtcacaag agagagagag agagaaattg ctgagtttga gttggatcat  1867
gccaaacaaa tttgtgtgaa atacttttg aatgttcaag tgtcttccct actttaaaaa  1927
tgttattcag ttggtggttg aacagtcagg tgattatgga gcacatacct ataatatgtg  1987
gagacctggg ttctagtctc agaactgaca aaaaaatttc tatcctcata tctcacatgc  2047
acacacacac acacacacac acacacacac acacacacac acacacacac acagcacacg  2107
aaactgcatt tctttctggc tcctaaacac ctttgtggtt gttcgtatcc agggaaacaa  2167
actaaaaatg tatgcaaaaa actctgccct caagcctttg aggcaggttg taagaaatca  2227
gccatagtct tagagtgaag aatgccattt gtgggtcttg tttccttcga agtactaaat  2287
acattttgcc tagtaatatc acttctcttt tcttatctgg caccccatt aggaaggtag  2347
aatttggaga actcatcaga aactaaattt attccaaaca aaatgacaat agaagaatat  2407
aactgataaa aaataaaata gtccattttt tgttttggtt ttacagctat aaatctaact  2467
gattaatagg ctaatgatgc tcactaattt tcttgaggca atagtcacct aggcagacac  2527
tttaggttga cacttttatt ctaaaagcct ttttaagggt aatttcctac tttgattaca  2587
ggagttgaaa tgtaactttt caaaaaggct caatccttac aagcttctca acatcagttc  2647
ttctgttaag tgctactgtt cattcacaga gctgagaatt ctggcaaaga tctttgtccc  2707
aacccttcct aatatccttg ccttattctt gagcatgggt tgcagcaggg attgtgacag  2767
cactacttct aaaatgttca tttgcagccc agtgcctcaa catcaatttt ccttcctgag  2827
gcttggcttt agaaatcacc ttttggaaaa actataacta ttccctagca aagatcatag  2887
gttcactgga tctgtccatc tgccgagcat gaatgaactc acatgagtac taagaaatgt  2947
gaagatcaag aaattctata tttcccactc taagtgagaa aacatgatag gaaaaagtat  3007
```

FIG. 2D

```
gaagagtctg gtctttacta gaacctgaca gagaagggaa ggctttgggg ccagggcttc 3067 atgagacaaa cttcctgcca gccaattaca cattctccca agaagagaag catagggcgt 3127 cctgggctgc aaagacactg aacattattg aagatgtgat ggggcaatgc caaccctctg 3187 ctgcttccct cttggaggaa acactatttc cagagtgcgg agatcaatca caggtcctga 3247 aggaaagtgg tgattcctgt gctagacgat tcacccgcag ggaaggtggt gattcccgtg 3307 ctagatgatt cactcacaaa ccttcccgcc caggtgttct ctgaaagctt agcctcaagg 3367 gaacacctaa agagctcccc tacctacata aacccctgcc tccaagtgta ggaactcacc 3427 tttctaaagc gctgtgggaa gcaggaactg ggcatctgtg ctaagtcaat gtagaatttc 3487 tccagcgttt taatgctggg tagaatatag agcatagggg aaaggggcca aactgcctat 3547 agttagtaga gaaaaatgaa tgtggttctt ttgtgcattt atgtgtatca taaacacttg 3607 ggaaagcaaa aaccataagc accattttgc aactttatcc attttccagt tagctcatgt 3667 aaacgagcac gaataacaaa acagtattac tctttcgcac ttctcacagg acatgtaccc 3727 aaatacggta cttatttatg tagtcactgt gtttcaggac ttttacgtta ataaaatttt 3787 tatttaaaat tttaaaaaaa aaaaaaaaaa aaaaaaaaa                   3827
```

FIG. 3A

```
tagccagacc tcggacgaga gcgccccggg gagctcggag cgcgtgcacg cgtggcagac    60
ggagaaggcc agtgcccagc ttgaaggttc tgccaccttt tgcagtggtc caaatgagaa   120
aaaagtggaa a atg gga ggc atg aaa tac atc ttt tcg ttg ttg ttc ttt   170
            Met Gly Gly Met Lys Tyr Ile Phe Ser Leu Leu Phe Phe
             1           5                       10 ctt ttg cta gaa gga ggc aaa aca gag caa gta aaa cat tca gag aca    218
Leu Leu Leu Glu Gly Gly Lys Thr Glu Gln Val Lys His Ser Glu Thr
        15              20                  25 tat tgc atg ttt caa gac aag aag tac aga gtg ggt gag aga tgg cat    266
Tyr Cys Met Phe Gln Asp Lys Lys Tyr Arg Val Gly Glu Arg Trp His
 30                  35                  40                  45 cct tac ctg gaa cct tat ggg ttg gtt tac tgc gtg aac tgc atc tgc    314
Pro Tyr Leu Glu Pro Tyr Gly Leu Val Tyr Cys Val Asn Cys Ile Cys
                 50                  55                  60 tca gag aat ggg aat gtg ctt tgc agc cga gtc aga tgt cca aat gtt    362
Ser Glu Asn Gly Asn Val Leu Cys Ser Arg Val Arg Cys Pro Asn Val
             65                  70                  75 cat tgc ctt tct cct gtg cat att cct cat ctg tgc tgc cct cgc tgc    410
His Cys Leu Ser Pro Val His Ile Pro His Leu Cys Cys Pro Arg Cys
         80                  85                  90 cca gaa gac tcc tta ccc cca gtg aac aat aag gtg acc agc aag tct    458
Pro Glu Asp Ser Leu Pro Pro Val Asn Asn Lys Val Thr Ser Lys Ser
     95                 100                 105 tgc gag tac aat ggg aca act tac caa cat gga gag ctg ttc gta gct    506
Cys Glu Tyr Asn Gly Thr Thr Tyr Gln His Gly Glu Leu Phe Val Ala
110                 115                 120                 125 gaa ggg ctc ttt cag aat cgg caa ccc aat caa tgc acc cag tgc agc    554
Glu Gly Leu Phe Gln Asn Arg Gln Pro Asn Gln Cys Thr Gln Cys Ser
                130                 135                 140 tgt tcg gag gga aac gtg tat tgt ggt ctc aag act tgc ccc aaa tta    602
Cys Ser Glu Gly Asn Val Tyr Cys Gly Leu Lys Thr Cys Pro Lys Leu
            145                 150                 155 acc tgt gcc ttc cca gtc tct gtt cca gat tcc tgc tgc cgg gta tgc    650
Thr Cys Ala Phe Pro Val Ser Val Pro Asp Ser Cys Cys Arg Val Cys
        160                 165                 170 aga gga gat gga gaa ctg tca tgg gaa cat tct gat ggt gat atc ttc    698
Arg Gly Asp Gly Glu Leu Ser Trp Glu His Ser Asp Gly Asp Ile Phe
    175                 180                 185
```

FIG. 3B

```
cgg caa cct gcc aac aga gaa gca aga cat tct tac cac cgc tct cac    746
Arg Gln Pro Ala Asn Arg Glu Ala Arg His Ser Tyr His Arg Ser His
190             195                 200                 205 tat gat cct cca cca agc cga cag gct gga ggt ctg tcc cgc ttt cct    794
Tyr Asp Pro Pro Pro Ser Arg Gln Ala Gly Gly Leu Ser Arg Phe Pro
                210                 215                 220 ggg gcc aga agt cac cgg gga gct ctt atg gat tcc cag caa gca tca    842
Gly Ala Arg Ser His Arg Gly Ala Leu Met Asp Ser Gln Gln Ala Ser
            225                 230                 235 gga acc att gtg caa att gtc atc aat aac aaa cac aag cat gga caa    890
Gly Thr Ile Val Gln Ile Val Ile Asn Asn Lys His Lys His Gly Gln
        240                 245                 250 gtg tgt gtt tcc aat gga aag acc tat tct cat ggc gag tcc tgg cac    938
Val Cys Val Ser Asn Gly Lys Thr Tyr Ser His Gly Glu Ser Trp His
    255                 260                 265 cca aac ctc cgg gca ttt ggc att gtg gag tgt gtg cta tgt act tgt    986
Pro Asn Leu Arg Ala Phe Gly Ile Val Glu Cys Val Leu Cys Thr Cys
270                 275                 280                 285 aat gtc acc aag caa gag tgt aag aaa atc cac tgc ccc aat cga tac   1034
Asn Val Thr Lys Gln Glu Cys Lys Lys Ile His Cys Pro Asn Arg Tyr
                290                 295                 300 ccc tgc aag tat cct caa aaa ata gac gga aag tgc tgc aag gtg tgt   1082
Pro Cys Lys Tyr Pro Gln Lys Ile Asp Gly Lys Cys Cys Lys Val Cys
                305                 310                 315 cca ggt aaa aaa gca aaa gaa gaa ctt cca ggc caa agc ttt gac aat   1130
Pro Gly Lys Lys Ala Lys Glu Glu Leu Pro Gly Gln Ser Phe Asp Asn
        320                 325                 330 aaa ggc tac ttc tgc ggg gaa gaa acg atg cct gtg tat gag tct gta   1178
Lys Gly Tyr Phe Cys Gly Glu Glu Thr Met Pro Val Tyr Glu Ser Val
    335                 340                 345 ttc atg gag gat ggg gag aca acc aga aaa ata gca ctg gag act gag   1226
Phe Met Glu Asp Gly Glu Thr Thr Arg Lys Ile Ala Leu Glu Thr Glu
350                 355                 360                 365 aga cca cct cag gta gag gtc cac gtt tgg act att cga aag ggc att   1274
Arg Pro Pro Gln Val Glu Val His Val Trp Thr Ile Arg Lys Gly Ile
                370                 375                 380 ctc cag cac ttc cat att gag aag atc tcc aag agg atg ttt gag gag   1322
Leu Gln His Phe His Ile Glu Lys Ile Ser Lys Arg Met Phe Glu Glu
        385                 390                 395
```

FIG. 3C

```
ctt cct cac ttc aag ctg gtg acc aga aca acc ctg agc cag tgg aag    1370
Leu Pro His Phe Lys Leu Val Thr Arg Thr Thr Leu Ser Gln Trp Lys
        400                 405                 410 atc ttc acc gaa gga gaa gct cag atc agc cag atg tgt tca agt cgt    1418
Ile Phe Thr Glu Gly Glu Ala Gln Ile Ser Gln Met Cys Ser Ser Arg
        415                 420                 425 gta tgc aga aca gag ctt gaa gat tta gtc aag gtt ttg tac ctg gag    1466
Val Cys Arg Thr Glu Leu Glu Asp Leu Val Lys Val Leu Tyr Leu Glu
430                 435                 440                 445 aga tct gaa aag ggc cac tgt taggcaagg                              1496
Arg Ser Glu Lys Gly His Cys
                450
```

FIG. 4A

```
atg gga ggc atg aaa tac atc ttt tcg ttg ttg ttc ttt ctt ttg cta    48
Met Gly Gly Met Lys Tyr Ile Phe Ser Leu Leu Phe Phe Leu Leu Leu
 1               5                  10                  15 gaa gga ggc aaa aca gag caa gta aaa cat tca gag aca tat tgc atg    96
Glu Gly Gly Lys Thr Glu Gln Val Lys His Ser Glu Thr Tyr Cys Met
             20                  25                  30 ttt caa gac aag aag tac aga gtg ggt gag aga tgg cat cct tac ctg   144
Phe Gln Asp Lys Lys Tyr Arg Val Gly Glu Arg Trp His Pro Tyr Leu
         35                  40                  45 gaa cct tat ggg ttg gtt tac tgc gtg aac tgc atc tgc tca gag aat   192
Glu Pro Tyr Gly Leu Val Tyr Cys Val Asn Cys Ile Cys Ser Glu Asn
     50                  55                  60 ggg aat gtg ctt tgc agc cga gtc aga tgt cca aat gtt cat tgc ctt   240
Gly Asn Val Leu Cys Ser Arg Val Arg Cys Pro Asn Val His Cys Leu
 65                  70                  75                  80 tct cct gtg cat att cct cat ctg tgc tgc cct cgc tgc cca gaa gac   288
Ser Pro Val His Ile Pro His Leu Cys Cys Pro Arg Cys Pro Glu Asp
                 85                  90                  95 tcc tta ccc cca gtg aac aat aag gtg acc agc aag tct tgc gag tac   336
Ser Leu Pro Pro Val Asn Asn Lys Val Thr Ser Lys Ser Cys Glu Tyr
             100                 105                 110 aat ggg aca act tac caa cat gga gag ctg ttc gta gct gaa ggg ctc   384
Asn Gly Thr Thr Tyr Gln His Gly Glu Leu Phe Val Ala Glu Gly Leu
         115                 120                 125 ttt cag aat cgg caa ccc aat caa tgc acc cag tgc agc tgt tcg gag   432
Phe Gln Asn Arg Gln Pro Asn Gln Cys Thr Gln Cys Ser Cys Ser Glu
     130                 135                 140 gga aac gtg tat tgt ggt ctc aag act tgc ccc aaa tta acc tgt gcc   480
Gly Asn Val Tyr Cys Gly Leu Lys Thr Cys Pro Lys Leu Thr Cys Ala
145                 150                 155                 160 ttc cca gtc tct gtt cca gat tcc tgc tgc cgg gta tgc aga gga gat   528
Phe Pro Val Ser Val Pro Asp Ser Cys Cys Arg Val Cys Arg Gly Asp
                 165                 170                 175 gga gaa ctg tca tgg gaa cat tct gat ggt gat atc ttc cgg caa cct   576
Gly Glu Leu Ser Trp Glu His Ser Asp Gly Asp Ile Phe Arg Gln Pro
             180                 185                 190 gcc aac aga gaa gca aga cat tct tac cac cgc tct cac tat gat cct   624
Ala Asn Arg Glu Ala Arg His Ser Tyr His Arg Ser His Tyr Asp Pro
         195                 200                 205
```

FIG. 4B

| | | | | | | | | | | | | | | | | |
|---|---|---|---|---|---|---|---|---|---|---|---|---|---|---|---|---|
| cca | cca | agc | cga | cag | gct | gga | ggt | ctg | tcc | cgc | ttt | cct | ggg | gcc | aga | 672 |
| Pro | Pro | Ser | Arg | Gln | Ala | Gly | Gly | Leu | Ser | Arg | Phe | Pro | Gly | Ala | Arg | |
| | 210 | | | | 215 | | | | | 220 | | | | | | |

| | | | | | | | | | | | | | | | | |
|---|---|---|---|---|---|---|---|---|---|---|---|---|---|---|---|---|
| agt | cac | cgg | gga | gct | ctt | atg | gat | tcc | cag | caa | gca | tca | gga | acc | att | 720 |
| Ser | His | Arg | Gly | Ala | Leu | Met | Asp | Ser | Gln | Gln | Ala | Ser | Gly | Thr | Ile | |
| 225 | | | | | 230 | | | | 235 | | | | | | 240 | |

| | | | | | | | | | | | | | | | | |
|---|---|---|---|---|---|---|---|---|---|---|---|---|---|---|---|---|
| gtg | caa | att | gtc | atc | aat | aac | aaa | cac | aag | cat | gga | caa | gtg | tgt | gtt | 768 |
| Val | Gln | Ile | Val | Ile | Asn | Asn | Lys | His | Lys | His | Gly | Gln | Val | Cys | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| tcc | aat | gga | aag | acc | tat | tct | cat | ggc | gag | tcc | tgg | cac | cca | aac | ctc | 816 |
| Ser | Asn | Gly | Lys | Thr | Tyr | Ser | His | Gly | Glu | Ser | Trp | His | Pro | Asn | Leu | |
| | | | 260 | | | | | 265 | | | | | 270 | | | |

| | | | | | | | | | | | | | | | | |
|---|---|---|---|---|---|---|---|---|---|---|---|---|---|---|---|---|
| cgg | gca | ttt | ggc | att | gtg | gag | tgt | gtg | cta | tgt | act | tgt | aat | gtc | acc | 864 |
| Arg | Ala | Phe | Gly | Ile | Val | Glu | Cys | Val | Leu | Cys | Thr | Cys | Asn | Val | Thr | |
| | | 275 | | | | | 280 | | | | | 285 | | | | |

| | | | | | | | | | | | | | | | | |
|---|---|---|---|---|---|---|---|---|---|---|---|---|---|---|---|---|
| aag | caa | gag | tgt | aag | aaa | atc | cac | tgc | ccc | aat | cga | tac | ccc | tgc | aag | 912 |
| Lys | Gln | Glu | Cys | Lys | Lys | Ile | His | Cys | Pro | Asn | Arg | Tyr | Pro | Cys | Lys | |
| | 290 | | | | | 295 | | | | | 300 | | | | | |

| | | | | | | | | | | | | | | | | |
|---|---|---|---|---|---|---|---|---|---|---|---|---|---|---|---|---|
| tat | cct | caa | aaa | ata | gac | gga | aag | tgc | tgc | aag | gtg | tgt | cca | gaa | gaa | 960 |
| Tyr | Pro | Gln | Lys | Ile | Asp | Gly | Lys | Cys | Cys | Lys | Val | Cys | Pro | Glu | Glu | |
| 305 | | | | | 310 | | | | 315 | | | | | | 320 | |

| | | | | | | | | | | | | | | | | |
|---|---|---|---|---|---|---|---|---|---|---|---|---|---|---|---|---|
| ctt | cca | ggc | caa | agc | ttt | gac | aat | aaa | ggc | tac | ttc | tgc | ggg | gaa | gaa | 1008 |
| Leu | Pro | Gly | Gln | Ser | Phe | Asp | Asn | Lys | Gly | Tyr | Phe | Cys | Gly | Glu | Glu | |
| | | | | 325 | | | | | 330 | | | | | 335 | | |

| | | | | | | | | | | | | | | | | |
|---|---|---|---|---|---|---|---|---|---|---|---|---|---|---|---|---|
| acg | atg | cct | gtg | tat | gag | tct | gta | ttc | atg | gag | gat | ggg | gag | aca | acc | 1056 |
| Thr | Met | Pro | Val | Tyr | Glu | Ser | Val | Phe | Met | Glu | Asp | Gly | Glu | Thr | Thr | |
| | | | 340 | | | | | 345 | | | | | 350 | | | |

| | | | | | | | | | | | | | | | | |
|---|---|---|---|---|---|---|---|---|---|---|---|---|---|---|---|---|
| aga | aaa | ata | gca | ctg | gag | act | gag | aga | cca | cct | cag | gta | gag | gtc | cac | 1104 |
| Arg | Lys | Ile | Ala | Leu | Glu | Thr | Glu | Arg | Pro | Pro | Gln | Val | Glu | Val | His | |
| | | 355 | | | | | 360 | | | | | 365 | | | | |

| | | | | | | | | | | | | | | | | |
|---|---|---|---|---|---|---|---|---|---|---|---|---|---|---|---|---|
| gtt | tgg | act | att | cga | aag | ggc | att | ctc | cag | cac | ttc | cat | att | gag | aag | 1152 |
| Val | Trp | Thr | Ile | Arg | Lys | Gly | Ile | Leu | Gln | His | Phe | His | Ile | Glu | Lys | |
| | 370 | | | | 375 | | | | | 380 | | | | | | |

| | | | | | | | | | | | | | | | | |
|---|---|---|---|---|---|---|---|---|---|---|---|---|---|---|---|---|
| atc | tcc | aag | agg | atg | ttt | gag | gag | ctt | cct | cac | ttc | aag | ctg | gtg | acc | 1200 |
| Ile | Ser | Lys | Arg | Met | Phe | Glu | Glu | Leu | Pro | His | Phe | Lys | Leu | Val | Thr | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| aga | aca | acc | ctg | agc | cag | tgg | aag | atc | ttc | acc | gaa | gga | gaa | gct | cag | 1248 |
| Arg | Thr | Thr | Leu | Ser | Gln | Trp | Lys | Ile | Phe | Thr | Glu | Gly | Glu | Ala | Gln | |
| | | | | 405 | | | | | 410 | | | | | 415 | | |

FIG. 4C

```
atc agc cag atg tgt tca agt cgt gta tgc aga aca gag ctt gaa gat    1296
Ile Ser Gln Met Cys Ser Ser Arg Val Cys Arg Thr Glu Leu Glu Asp
            420                 425                 430 tta gtc aag gtt ttg tac ctg gag aga tct gaa aag ggc cac tgt        1341
Leu Val Lys Val Leu Tyr Leu Glu Arg Ser Glu Lys Gly His Cys
            435                 440                 445
```

CR: pro-collagen repeat
sp: signal peptide
tm: transmembrane domain (only in Drosophila sog)
*: possible BMP1 cleavage site (A/GD sequence)

FIG. 6A

```
              1                                                      50
Hch1        ~~~~~~~~~~  ~~~~~~~~~~  ~~~~~~~~~~  ~~~~~~~~~~  ~~~~~~~~~~
Hch1d5      ~~~~~~~~~~  ~~~~~~~~~~  ~~~~~~~~~~  ~~~~~~~~~~  ~~~~~~~~~~
Mch1        ~~~~~~~~~~  ~~~~~~~~~~  ~~~~~~~~~~  ~~~~~~~~~~  ~~~~~~~~~~
Rch1        ~~~~~~~~~~  ~~~~~~~~~~  ~~~~~~~~~~  ~~~~~~~~~~  ~~~~~~~~~~
Mchordin    MPSLPAPPAP  RLLLGLLLLG  SRPASGTGPE  PPALPIRSEK  EPLPVRGAAG
Rchordin    ~~~~~~~~~~  ~~~~~~~~~~  ~~~~~~~~~~  ~~~~~~~~~~  ~~~~~~~~~~
Hchordin    ~~~~~~~~~~  ~~~~~~~~~~  ~~~~~~~~~~  ~~~~~~~~~~  ~~~~~~~~~~

51                                                     100
Hch1        ~~~~~~~~~~  ~~~~~~~~~~  ~~~~~~~~~~  ~~~~~~~~~~  ~~~~~~~~~~
Hch1d5      ~~~~~~~~~~  ~~~~~~~~~~  ~~~~~~~~~~  ~~~~~~~~~~  ~~~~~~~~~~
Mch1        ~~~~~~~~~~  ~~~~~~~~~~  ~~~~~~~~~~  ~~~~~~~~~~  ~~~~~~~~~~
Rch1        ~~~~~~~~~~  ~~~~~~~~~~  ~~~~~~~~~~  ~~~~~~~~~~  ~~~~~~~~~~
Mchordin    CSFGGKVYAL  DETWHPDLGE  PFGVMRCVLC  ACEAPQWARR  GRGPGRVSCK
Rchordin    ~~~~~~~~~~  ~~~~~~~~~~  ~~~~~~~~~~  ~~~~~~~~~~  ~~~~~~~~~~
Hchordin    ~~~~~~~~~~  ~~~~~~~~~~  ~~~~~~~~~~  ~~~~~~~~~~  ~~~~~~~~~~

101                                                    150
Hch1        ~~~~~~~~~~  ~~~~~~~~~~  ~~~~~~~~~~  ~~~~~~~~~~  ~~~~~~~~~~
Hch1d5      ~~~~~~~~~~  ~~~~~~~~~~  ~~~~~~~~~~  ~~~~~~~~~~  ~~~~~~~~~~
Mch1        ~~~~~~~~~~  ~~~~~~~~~~  ~~~~~~~~~~  ~~~~~~~~~~  ~~~~~~~~~~
Rch1        ~~~~~~~~~~  ~~~~~~~~~~  ~~~~~~~~~~  ~~~~~~~~~~  ~~~~~~~~~~
Mchordin    NIKPQCPTLA  CRQPRQLPGH  CCQTCPQERS  NLDPQPAGLV  FEYPRDPEHR
Rchordin    ~~~~~~~~~~  ~~~~~~~~~~  ~~~~~~~~~~  ~~~~~~~~~~  ~~~~~~~~~~
Hchordin    ~~~~~~~~~~  ~~~~QVAAGH  CCQTCPQERS  SSERQPSGLS  FEYPRDPEHR 151                                                    200
Hch1        ~~~~~~~~~~  ~~~~~~~~~~  ~~~~~~~~~~  ~~~~~~~~~~  ~~~~~~~~~~
Hch1d5      ~~~~~~~~~~  ~~~~~~~~~~  ~~~~~~~~~~  ~~~~~~~~~~  ~~~~~~~~~~
Mch1        ~~~~~~~~~~  ~~~~~~~~~~  ~~~~~~~~~~  ~~~~~~~~~~  ~~~~~~~~~~
Rch1        ~~~~~~~~~~  ~~~~~~~~~~  ~~~~~~~~~~  ~~~~~~~~~~  ~~~~~~~~~~
Mchordin    SYSDRGEPGV  GERTRADGHT  DFVALLTGPR  SQAVARARVS  LLRSSLRFSV
Rchordin    ~~~~~~~~~~  ~~~~~~~~~~  ~~~~~~~~~~  ~~~~~~~~~~  ~~~~~~~~~~
Hchordin    SYSDRGEPGA  EERARGDGHT  DFVALLTGPR  SQAVARARAS  LLRSSLRFSI 201                                                    250
Hch1        ~~~~~~~~~~  ~~~~~~~~~~  ~~~~~~~~~~  ~~~~~~~~~~  ~~~~~~~~~~
Hch1d5      ~~~~~~~~~~  ~~~~~~~~~~  ~~~~~~~~~~  ~~~~~~~~~~  ~~~~~~~~~~
Mch1        ~~~~~~~~~~  ~~~~~~~~~~  ~~~~~~~~~~  ~~~~~~~~~~  ~~~~~~~~~~
Rch1        ~~~~~~~~~~  ~~~~~~~~~~  ~~~~~~~~~~  ~~~~~~~~~~  ~~~~~~~~~~
Mchordin    SYQRLDRPSR  VRFTDPTGNI  LFEHPATPTQ  DGLVCGVWRA  VPRLSVRLLR
Rchordin    ~~~~~~~~~~  ~~~~~~~~~~  ~~~~~~~~~~  ~~~~~~~~~~  ~~~~~~~~~~
Hchordin    SYRRLDRPTR  IRFSDPNGSV  LFEHPAAPTQ  DGLVCGVWRA  VPRLSLRLLR 251                                                    300
Hch1        ~~~~~~~~~~  ~~~~~~~~~~  ~~~~~~~~~~  ~~~~~~~~~~  ~~~~~~~~~~
Hch1d5      ~~~~~~~~~~  ~~~~~~~~~~  ~~~~~~~~~~  ~~~~~~~~~~  ~~~~~~~~~~
Mch1        ~~~~~~~~~~  ~~~~~~~~~~  ~~~~~~~~~~  ~~~~~~~~~~  ~~~~~~~~~~
Rch1        ~~~~~~~~~~  ~~~~~~~~~~  ~~~~~~~~~~  ~~~~~~~~~~  ~~~~~~~~~~
Mchordin    AEQLRVALVT  STHPSGEVWG  PLIWQGALAA  ETFSAILTLE  DPLQRGVGGI
Rchordin    ~~~~~~~~~~  ~~~~~~~~~~  ~~~~~~~~~~  ~~~~~~~~~~  ~~~~~~~~~~
Hchordin    AEQLHVALVT  LTHPSGEVWG  PLIRHRALAA  ETFSAILTLE  GPPQQGVGGI
```

FIG. 6B

```
           301                                                      350
Hch1       ~~~~~~~~~~ ~~~~~~~~~~ ~~~~~~~~~~ ~~~~~~~~~~ ~~~~~~~~~~
Hch1d5     ~~~~~~~~~~ ~~~~~~~~~~ ~~~~~~~~~~ ~~~~~~~~~~ ~~~~~~~~~~
Mch1       ~~~~~~~~~~ ~~~~~~~~~~ ~~~~~~~~~~ ~~~~~~~~~~ ~~~~~~~~~~
Rch1       ~~~~~~~~~~ ~~~~~~~~~~ ~~~~~~~~~~ ~~~~~~~~~~ ~~~~~~~~~~
Mchordin   ALLTLSDTED SLHFLLLFRG LL....GGLA QAPLKLQILH QGQLLRELQA
Rchordin   ~~~~~~~~~~ ~~~~~~~~~~ ~~~~~~~~~~ ~~~~~~~~~~ ~~~~~~~~~~
Hchordin   TLLTLSDTED SLHFLLLFRG LLEPRSGGLT QVPLRLQILH QGQLLRELQA 351                                                      400
Hch1       ~~~~~~~~~~ ~~~~~~~~~~ ~~~~~~~~~~ ~~~~~~~~~~ ~~~~~~~~~~
Hch1d5     ~~~~~~~~~~ ~~~~~~~~~~ ~~~~~~~~~~ ~~~~~~~~~~ ~~~~~~~~~~
Mch1       ~~~~~~~~~~ ~~~~~~~~~~ ~~~~~~~~~~ ~~~~~~~~~~ ~~~~~~~~~~
Rch1       ~~~~~~~~~~ ~~~~~~~~~~ ~~~~~~~~~~ ~~~~~~~~~~ ~~~~~~~~~~
Mchordin   NTSAQEPGFA EVLPSLTDQE MDWLELGELQ MVLEKAGGPE LRISGYITTR
Rchordin   ~~~~~~~~~~ ~~~~~~~~~~ ~~~~~~~~~~ ~~~~~~~~~~ ~~~~~~~~~~
Hchordin   NVSAQEPGFA EVLPNLTVQE MDWLVLGELQ MALEWAGRPG LRISGHIAAR 401                                                      450
Hch1       ~~~~~~~~~~ ~~~~~~~~~~ ~~~~~~~~~~ ~~~~~~~~~~ ~~~~~~~~~~
Hch1d5     ~~~~~~~~~~ ~~~~~~~~~~ ~~~~~~~~~~ ~~~~~~~~~~ ~~~~~~~~~~
Mch1       ~~~~~~~~~~ ~~~~~~~~~~ ~~~~~~~~~~ ~~~~~~~~~~ ~~~~~~~~~~
Rch1       ~~~~~~~~~~ ~~~~~~~~~~ ~~~~~~~~~~ ~~~~~~~~~~ ~~~~~~~~~~
Mchordin   QSCDVLQSVL CGADALIPVQ TGAAGSASFI LLGNGSLIYQ VQVVGTGSEV
Rchordin   ~~~~~~~~~~ ~~~~~~~~~~ ~~~~~~~~~~ ~~~~~~~~~~ ~~~~~~~~~~
Hchordin   KSCDVLQSVL CGADALIPVQ TGAAGSASLT LLGNGSLIYQ ..........

451                                                      500
Hch1       ~~~~~~~~~~ ~~~~~~~~~~ ~~~~~~~~~~ ~~~~~~~~~~ ~~~~~~~~~~
Hch1d5     ~~~~~~~~~~ ~~~~~~~~~~ ~~~~~~~~~~ ~~~~~~~~~~ ~~~~~~~~~~
Mch1       ~~~~~~~~~~ ~~~~~~~~~~ ~~~~~~~~~~ ~~~~~~~~~~ ~~~~~~~~~~
Rch1       ~~~~~~~~~~ ~~~~~~~~~~ ~~~~~~~~~~ ~~~~~~~~~~ ~~~~~~~~~~
Mchordin   VAMTLETKPQ RKNQRTVLCH MAGLQPGGHM AVGMCSGLGA RGAHMLLQNE
Rchordin   ~~~~~~~~~~ ~~~~~~~~~~ ~~~~~~~~~~ ~~~~~~~~~~ ~~~~~~~~~~
Hchordin   .......... .......... .......... AVGICPGLGA RGAHMLLQNE 501                                                      550
Hch1       ~~~~~~~~~~ ~~~~~~~~~~ ~~~~~~~~~~ ~~~~~~~~~~ ~~~~~~~~~~
Hch1d5     ~~~~~~~~~~ ~~~~~~~~~~ ~~~~~~~~~~ ~~~~~~~~~~ ~~~~~~~~~~
Mch1       ~~~~~~~~~~ ~~~~~~~~~~ ~~~~~~~~~~ ~~~~~~~~~~ ~~~~~~~~~~
Rch1       ~~~~~~~~~~ ~~~~~~~~~~ ~~~~~~~~~~ ~~~~~~~~~~ ~~~~~~~~~~
Mchordin   LFLNVGTKDF PDGELRGHVT ALCYSGHSAR YDRLPVPLAG ALVLPPVRSQ
Rchordin   ~~~~~~~~~~ ~~~~~~~~~~ ~~~~~~~~~~ ~~~~~~~~~~ ~~~~~~~~~~
Hchordin   LFLNVGTKDF PDGELRGHVA ALPYCGHSAR HDTLPVPLAG ALVLPPVKSQ 551                                                      600
Hch1       ~~~~~~~~~~ ~~~~~~~~~~ ~~~~~~~~~~ ~~~~~~~~~~ ~~~~~~~~~~
Hch1d5     ~~~~~~~~~~ ~~~~~~~~~~ ~~~~~~~~~~ ~~~~~~~~~~ ~~~~~~~~~~
Mch1       ~~~~~~~~~~ ~~~~~~~~~~ ~~~~~~~~~~ ~~~~~~~~~~ ~~~~~~~~~~
Rch1       ~~~~~~~~~~ ~~~~~~~~~~ ~~~~~~~~~~ ~~~~~~~~~~ ~~~~~~~~~~
Mchordin   AAGHAWLSLD THCHLHYEVL LAGLGGSEQG TVTAHLLGPP GMPGPQRLLK
Rchordin   ~~~~~~~~~~ ~~~~~~~~~~ ~~~~~~~~~~ ~~~~~~~~~~ ~~~~~~~~~~
Hchordin   AAGHAWLSLD THCHLHYEVL LAGLGGSEQG TVTAHLLGPP GTPGPRRLLK
```

FIG. 6C

```
          601                                                              650
Hchl      ~~~~~~~~~~ ~~~~~~~~~~ ~~~~~~~~~~ ~~~~~~~~~~ ~~~~~~~~~~
Hchld5    ~~~~~~~~~~ ~~~~~~~~~~ ~~~~~~~~~~ ~~~~~~~~~~ ~~~~~~~~~~
Mchl      ~~~~~~~~~~ ~~~~~~~~~~ ~~~~~~~~~~ ~~~~~~~~~~ ~~~~~~~~~~
Rchl      ~~~~~~~~~~ ~~~~~~~~~~ ~~~~~~~~~~ ~~~~~~~~~~ ~~~~~~~~~~
Mchordin  GFYGSEAQGV VKDLEPVLLR HLAQGTASLL ITTKSSPRGE LRGQVHIASQ
Rchordin  ~~~~~~~~~~ ~~~~~~~~~~ ~~~~~~~~~~ ~~~~~~~~~~ ~~~~~~~~~~
Hchordin  GFYGSEAQGV VKDLEPELLR HLAKGMASLL ITTKGSPRGE LRGQVHIANQ 651                                                              700
Hchl      ~~~~~~~~~~ ~~~~~~~~~~ ~~~~~~~~~~ ~~~~~~~~~~ ~~~~~~~~~~
Hchld5    ~~~~~~~~~~ ~~~~~~~~~~ ~~~~~~~~~~ ~~~~~~~~~~ ~~~~~~~~~~
Mchl      ~~~~~~~~~~ ~~~~~~~~~~ ~~~~~~~~~~ ~~~~~~~~~~ ~~~~~~~~~~
Rchl      ~~~~~~~~~~ ~~~~~~~~~~ ~~~~~~~~~~ ~~~~~~~~~~ ~~~~~~~~~~
Mchordin  CEAGGLRLAS EGVQMPLAPN GEAATSPMLP AGPGPEAPVP AKHGSPGRPR
Rchordin  ~~~GGLRLAS EGVRMSLAPN GEAATSPMLP AGPGPEAPVP AKHGSSGRPR
Hchordin  CEVGGLRLEA AGAEGVRALG APDPASAAPP VVPGLPALAP AKPGGPGRPR 701                                                              750
Hchl      ~~~~~~~~~~ ~~~~~~~~~~ ~~~~~~~~~~ ~~~~~~~~~~ ~~~~~~~~~~
Hchld5    ~~~~~~~~~~ ~~~~~~~~~~ ~~~~~~~~~~ ~~~~~~~~~~ ~~~~~~~~~~
Mchl      ~~~~~~~~~~ ~~~~~~~~~~ ~~~~~~~~~~ ~~~~~~~~~~ ~~~~~~~~~~
Rchl      ~~~~~~~~~~ ~~~~~~~~~~ ~~~~~~~~~~ ~~~~~~~~~~ ~~~~~~~~~~
Mchordin  DPNTCFFEGQ QRPHGARWAP NYDPLCSLCI CQRRTVICDP VVCPPPSCPH
Rchordin  DPNTCFFEGQ QRPHGARWAP NYDPLCSLCT CQRRTVICDP VVCPPPRCSQ
Hchordin  DPNTCFFEGQ QRPHGARWAP NYDPLCSLCT CQRRTVICDP VVCPPPSCPH 751                                                              800
Hchl      ~~~~MGGMKY IFSLLF.FLL LEGGKTEQVK HSETYCMFQD KKYRVGERWH
Hchld5    ~~~~MGGMKY IFSLLF.FLL LEGGKTEQVK HSETYCMFQD KKYRVGERWH
Mchl      ~~~~MDGMKY IISLFFIFVF LEGSKTEQVK HSDTYCVFQD KKYRVGEKWH
Rchl      ~~~~MEGIKY IASLVFFFVF LEASKTEPVK HSETYCMFQD KKYRVGEKWH
Mchordin  PVQALDQCCP VCPEKQRSRD LPSLP.NLEP GEGCYFDGDR SWRAAGTRWH
Rchordin  PVQALDQWCP VCSEKQRSRD LSSLP.NLEP GEGCYFDGDR SWRAAGTRWH
Hchordin  PVQAPDQCCP VCPEKQDVRD LPGLPRSRDP GEGCYFDGDR SWRAAGTRWH 801                                                              850
Hchl      PYLEPYGLVY CVNCIC.SEN GNVLCSRVRC PNVHCLSPVH I.PHLCCPRC
Hchld5    PYLEPYGLVY CVNCIC.SEN GNVLCSRVRC PNVHCLSPVH I.PHLCCPRC
Mchl      PYLEPYGLVY CVNCIC..SEN GNVLCSRVRC PSLHCLSPVH I.PHLCCPRC
Rchl      PYLEPYGLVY CVNCIC.SEN GNVLCSRVRC PTLHCLSPVH I.PHLCCPRC
Mchordin  PVVPPFGLIK CAVCTCKGAT GEVHCEKVQC PRLACAQPVR ANPTDCCKQC
Rchordin  PVVPPFGLIK CGVCTCKGVN GEVHSEKVQC ~~~~~~~~~~ ~~~~~~~~~~
Hchordin  PVVPPFGLIK CAVCTCKGGT GEVHCEKVQC PRLACAQPVR VNPTDCCKQC 851                                                              900
Hchl      PEDSLPPVNN KVTSKSCEYN GTTYQHGELF VAEGLFQNRQ PNQCTQCSCS
Hchld5    PEDSLPPVNN KVTSKSCEYN GTTYQHGELF VAEGLFQNRQ PNQCTQCSCS
Mchl      P.DSLPPVNN KVTSKSCEYN GTTYQHGELF IAEGLFQNRQ PNQCSQCSCS
Rchl      P.DSLPPMNN KVTSKSCEYN GTTYQHGELF IAEGLFQNRQ PNQCSQCSCS
Mchordin  PVGS..GTNA KLGDPMQADG PRGCRFAGQW FPENQSWHPS VPPFGEMSCI
Rchordin  ~~~~~~~~~~ ~~~~~~~~~~ ~~~~~~~~~~ ~~~~~~~~~~ ~~~~~~~~~~
Hchordin  PVGS..GAHP QLGDPMQADG PRGCRFAGQW FPESQSWHPS VPPFGEMSCI
```

FIG. 6D

```
          901                                                         950
Hchl      EGNVYCGLKT CPKLTCAFPV SVPDSCCRVC RGDGELSWEH SDGDIFRQPA
Hchld5    EGNVYCGLKT CPKLTCAFPV SVPDSCCRVC RGDGELSWEH SDGDIFRQPA
Mchl      EGNVYCGLKT CPKLTCAFPV SVPDSCCRVC RGDAELSWEH ADGDIFRQPA
Rchl      EGNVYCGLKT CPKLTCAFPV SVPDSCCRVC RGDGELSWEH SDADIFRQPA
Mchordin  TCRCGAGVPH CERDDCSPPL SCGSGKESRC CSHCTAQR.. SSETRTLPEL
Rchordin  ~~~~~~~~~~ ~~~~~~~~~~ ~~~~~~~~~~ ~~~~~~~~~~ ~~~~~~~~~~
Hchordin  TCRCGAGVPH CERDDCSLPL SCGSGKESRC CSRCTAHRRP APETRTDPEL 951                                                        1000
Hchl      NREARHSYHR SHYDPPPSRQ AGGLSRFPGA RSHRGALMDS QQASGTIVQI
Hchld5    NREARHSYHR SHYDPPPSRQ AGGLSRFPGA RSHRGALMDS QQASGTIVQI
Mchl      NREARHSYLR SPYDPPPNRQ AGGLPRFPGS RSHRGAVIDS QQASGTIVQI
Rchl      NREARHSYLR SPYDPPPSRQ AGGLPRFAGS RSHRGAVIDS QQASGTIVQI
Mchordin  EKEAEHS~~~ ~~~~~~~~~~ ~~~~~~~~~~ ~~~~~~~~~~ ~~~~~~~~~~
Rchordin  ~~~~~~~~~~ ~~~~~~~~~~ ~~~~~~~~~~ ~~~~~~~~~~ ~~~~~~~~~~
Hchordin  EKEAEGS~~~ ~~~~~~~~~~ ~~~~~~~~~~ ~~~~~~~~~~ ~~~~~~~~~~

1001                                                       1050
Hchl      VINNKHKHGQ VCVSNGKTYS HGESWHPNLR AFGIVECVLC TCNVTKQECK
Hchld5    VINNKHKHGQ VCVSNGKTYS HGESWHPNLR AFGIVECVLC TCNVTKQECK
Mchl      VINNKHKHGQ VCVSNGKTYS HGESWHPNLR AFGIVECVLC TCNVTKQECK
Rchl      VINNKHKHGQ VCVSNGKTYS HGESWHSNLR AFGIVECVLC TCNVTKQECK
Mchordin  ~~~~~~~~~~ ~~~~~~~~~~ ~~~~~~~~~~ ~~~~~~~~~~ ~~~~~~~~~~
Rchordin  ~~~~~~~~~~ ~~~~~~~~~~ ~~~~~~~~~~ ~~~~~~~~~~ ~~~~~~~~~~
Hchordin  ~~~~~~~~~~ ~~~~~~~~~~ ~~~~~~~~~~ ~~~~~~~~~~ ~~~~~~~~~~

1051                                                       1100
Hchl      KIHCPNRYPC KYPQKIDGKC CKVCPGKKAK EELPGQSFDN KGYFCGEETM
Hchld5    KIHCPNRYPC KYPQKIDGKC CKVCP..... EELPGQSFDN KGYFCGEETM
Mchl      KIHCPNRYPC KYPQKIDGKC CKVCPGKKAK GALAGGPAFG *~~~~~~~~~
Rchl      KIHCPNRYPC KYPQKLDGKC CKVCP..... EEPPSQNFDS KGSFCGEETM
Mchordin  ~~~~~~~~~~ ~~~~~~~~~~ ~~~~~~~~~~ ~~~~~~~~~~ ~~~~~~~~~~
Rchordin  ~~~~~~~~~~ ~~~~~~~~~~ ~~~~~~~~~~ ~~~~~~~~~~ ~~~~~~~~~~
Hchordin  ~~~~~~~~~~ ~~~~~~~~~~ ~~~~~~~~~~ ~~~~~~~~~~ ~~~~~~~~~~

1101                                                       1150
Hchl      PVYESVFMED GETTRKIALE TERPPQVEVH VWTIRKGILQ HFHIEKISKR
Hchld5    PVYESVFMED GETTRKIALE TERPPQVEVH VWTIRKGILQ HFHIEKISKR
Mchl      ~~~~~~~~~~ ~~~~~~~~~~ ~~~~~~~~~~ ~~~~~~~~~~ ~~~~~~~~~~
Rchl      PVYEAVLVED GETARKVALE TEKPPQVVGS RLDYSKGHSP ALPH*~~~~~
Mchordin  ~~~~~~~~~~ ~~~~~~~~~~ ~~~~~~~~~~ ~~~~~~~~~~ ~~~~~~~~~~
Rchordin  ~~~~~~~~~~ ~~~~~~~~~~ ~~~~~~~~~~ ~~~~~~~~~~ ~~~~~~~~~~
Hchordin  ~~~~~~~~~~ ~~~~~~~~~~ ~~~~~~~~~~ ~~~~~~~~~~ ~~~~~~~~~~

1151                                                       1200
Hchl      MFEELPHFKL VTRTTLSQWK IFTEGEAQIS QMCSSRVCRT ELEDLVKVLY
Hchld5    MFEELPHFKL VTRTTLSQWK IFTEGEAQIS QMCSSRVCRT ELEDLVKVLY
Mchl      ~~~~~~~~~~ ~~~~~~~~~~ ~~~~~~~~~~ ~~~~~~~~~~ ~~~~~~~~~~
Rchl      ~~~~~~~~~~ ~~~~~~~~~~ ~~~~~~~~~~ ~~~~~~~~~~ ~~~~~~~~~~
Mchordin  ~~~~~~~~~~ ~~~~~~~~~~ ~~~~~~~~~~ ~~~~~~~~~~ ~~~~~~~~~~
Rchordin  ~~~~~~~~~~ ~~~~~~~~~~ ~~~~~~~~~~ ~~~~~~~~~~ ~~~~~~~~~~
Hchordin  ~~~~~~~~~~ ~~~~~~~~~~ ~~~~~~~~~~ ~~~~~~~~~~ ~~~~~~~~~~
```

FIG. 6E

```
          1201
Hchl      LERSEKGHC*
Hchld5    LERSEKGHC*
Mchl      ~~~~~~~~~~
Rchl      ~~~~~~~~~~
Mchordin  ~~~~~~~~~~
Rchordin  ~~~~~~~~~~
Hchordin  ~~~~~~~~~~
```

CHL expression beta-actin control

IP.with anti-flag Ab

SEQUENCE LISTING

```
<160> NUMBER OF SEQ ID NOS: 37

<210> SEQ ID NO 1
<211> LENGTH: 1864
<212> TYPE: DNA
<213> ORGANISM: Mus musculus
<220> FEATURE:
<221> NAME/KEY: CDS
<222> LOCATION: (148)..(1146)
<220> FEATURE:
<221> NAME/KEY: sig_peptide
<222> LOCATION: (148)..(213)

<400> SEQUENCE: 1
ccacgcgtcc ggagcgcccc agggagctca gagcttgtgc aagcgtggca gcaggaggag      60
gccagtgccc agctttagtc caccgctcct ctccttggag cccctgaatt gcattttgca     120
gtagctcgaa ggagaaaaaa gtagaag atg gat ggc atg aaa tac atc att tcc     174
                             Met Asp Gly Met Lys Tyr Ile Ile Ser
```

-continued

```
                  1                   5
tta ttt ttc atc ttt gtt ttc cta gaa gga agc aaa aca gaa caa gta      222
Leu Phe Phe Ile Phe Val Phe Leu Glu Gly Ser Lys Thr Glu Gln Val
 10              15                  20                  25 aaa cac tca gac aca tat tgc gtg ttt caa gac aag aag tat aga gtg      270
Lys His Ser Asp Thr Tyr Cys Val Phe Gln Asp Lys Lys Tyr Arg Val
                 30                  35                  40 ggt gag aaa tgg cat ccc tac ctg gaa ccg tat gga ctg gtt tac tgt      318
Gly Glu Lys Trp His Pro Tyr Leu Glu Pro Tyr Gly Leu Val Tyr Cys
                 45                  50                  55 gtg aac tgc atc tgc tct gag aat ggg aat gtg ctt tgc agc cga gtc      366
Val Asn Cys Ile Cys Ser Glu Asn Gly Asn Val Leu Cys Ser Arg Val
         60                  65                  70 aga tgt cca agt ctt cat tgc ctt tca ccc gtg cat att cct cat ctc      414
Arg Cys Pro Ser Leu His Cys Leu Ser Pro Val His Ile Pro His Leu
     75                  80                  85 tgt tgc ccc cgc tgc cca gac tcc tta cca cca gtg aac aat aag gtg      462
Cys Cys Pro Arg Cys Pro Asp Ser Leu Pro Pro Val Asn Asn Lys Val
 90                  95                 100                 105 acc agc aag tca tgc gaa tac aat gga acc act tac caa cat gga gaa      510
Thr Ser Lys Ser Cys Glu Tyr Asn Gly Thr Thr Tyr Gln His Gly Glu
                110                 115                 120 ctg ttc ata gct gaa ggg ctc ttt cag aac cgg caa ccc aat cag tgc      558
Leu Phe Ile Ala Glu Gly Leu Phe Gln Asn Arg Gln Pro Asn Gln Cys
                125                 130                 135 agt cag tgt agc tgc tcg gag ggg aat gta tac tgt ggt ctc aag act      606
Ser Gln Cys Ser Cys Ser Glu Gly Asn Val Tyr Cys Gly Leu Lys Thr
            140                 145                 150 tgc ccc aaa ctg acc tgt gca ttc cca gtc tct gtt cca gat tct tgc      654
Cys Pro Lys Leu Thr Cys Ala Phe Pro Val Ser Val Pro Asp Ser Cys
155                 160                 165 tgc cga gta tgc aga ggg gat gca gaa tta tcg tgg gaa cat gcg gat      702
Cys Arg Val Cys Arg Gly Asp Ala Glu Leu Ser Trp Glu His Ala Asp
170                 175                 180                 185 ggt gat atc ttc cgg caa cct gcc aac aga gaa gca aga cat tct tac      750
Gly Asp Ile Phe Arg Gln Pro Ala Asn Arg Glu Ala Arg His Ser Tyr
                190                 195                 200 ctc cgt tcc ccc tac gat cct cca cca aac aga caa gct gga ggt ctt      798
Leu Arg Ser Pro Tyr Asp Pro Pro Pro Asn Arg Gln Ala Gly Gly Leu
                205                 210                 215 ccc cgc ttt cct ggg agc aga agt cac cgg gga gct gtt ata gat tcc      846
Pro Arg Phe Pro Gly Ser Arg Ser His Arg Gly Ala Val Ile Asp Ser
        220                 225                 230 cag caa gca tcc ggg acc atc gtg cag att gtc atc aat aac aag cac      894
Gln Gln Ala Ser Gly Thr Ile Val Gln Ile Val Ile Asn Asn Lys His
    235                 240                 245 aaa cat gga caa gtg tgt gtt tcc aat gga aag acc tac tct cat gga      942
Lys His Gly Gln Val Cys Val Ser Asn Gly Lys Thr Tyr Ser His Gly
250                 255                 260                 265 gag tcc tgg cac cca aat cta cga gca ttt ggc att gtg gaa tgt gta      990
Glu Ser Trp His Pro Asn Leu Arg Ala Phe Gly Ile Val Glu Cys Val
                270                 275                 280 cta tgc act tgt aat gtc acc aag caa gaa tgt aag aaa atc cac tgc     1038
Leu Cys Thr Cys Asn Val Thr Lys Gln Glu Cys Lys Lys Ile His Cys
                285                 290                 295 ccc aat cga tac ccc tgc aag tat cct caa aaa ata gat gga aag tgc     1086
Pro Asn Arg Tyr Pro Cys Lys Tyr Pro Gln Lys Ile Asp Gly Lys Cys
            300                 305                 310 tgc aag gtg tgc cca ggt aaa aag gca aaa ggt gca ttg gct gga ggc     1134
```

```
                Cys Lys Val Cys Pro Gly Lys Lys Ala Lys Gly Ala Leu Ala Gly Gly
                315                 320                 325 cct gcc ttt ggt tgaatgagat tcacacatag tcctattcag tcttctttgt         1186
Pro Ala Phe Gly
330 tcatcaaaac tataaatgac ctgtcttata gttctaacga taatagttct agcaagaatg   1246 aacttcatcc tttcgtcttc tgagacactg atggttgctt tgaaggaatt aactactcag   1306 agtttctttt gtctacaatg tcaaacacat gccaagttgc ttatcttgtt cttgcttttc   1366 taaattagag agtttacgtt atcactgttt tagaaaaagt cacacccttc atggtttaaa   1426 tcaccaactc acttcaagac ataatccagt actcttttca gatgagatat aaatgagtta   1486 cagtggagag aaattagatt ctgatccaaa tgcatcaaat ccacaagtat cttaccccat   1546 gtgaacattt taaagtttat tactgtgttc cacattgcta tttta atttg caatttcttt   1606 ttaaattttc tgagatattg tatctgtata tacttatggg gtacagtatg ttaattcaat   1666 acaaatatac aaggtataat tgtcaaatca gggtaattat cattctctct cctctgattt   1726 tatccctaga ctcttctagt cattttaaaa tttatcatca attgggtttt tgatatggta   1786 actccactgt gctaaagaaa ccattcattc taatggcatt ttaggatcta ctatctaacc   1846 tctatctccc cttctgtt                                                 1864

<210> SEQ ID NO 2
<211> LENGTH: 333
<212> TYPE: PRT
<213> ORGANISM: Mus musculus

<400> SEQUENCE: 2

Met Asp Gly Met Lys Tyr Ile Ile Ser Leu Phe Phe Ile Phe Val Phe
1               5                   10                  15

Leu Glu Gly Ser Lys Thr Glu Gln Val Lys His Ser Asp Thr Tyr Cys
                20                  25                  30

Val Phe Gln Asp Lys Lys Tyr Arg Val Gly Glu Lys Trp His Pro Tyr
            35                  40                  45

Leu Glu Pro Tyr Gly Leu Val Tyr Cys Val Asn Cys Ile Cys Ser Glu
        50                  55                  60

Asn Gly Asn Val Leu Cys Ser Arg Val Arg Cys Pro Ser Leu His Cys
65                  70                  75                  80

Leu Ser Pro Val His Ile Pro His Leu Cys Cys Pro Arg Cys Pro Asp
                85                  90                  95

Ser Leu Pro Pro Val Asn Asn Lys Val Thr Ser Lys Ser Cys Glu Tyr
            100                 105                 110

Asn Gly Thr Thr Tyr Gln His Gly Glu Leu Phe Ile Ala Glu Gly Leu
        115                 120                 125

Phe Gln Asn Arg Gln Pro Asn Gln Cys Ser Gln Cys Ser Cys Ser Glu
    130                 135                 140

Gly Asn Val Tyr Cys Gly Leu Lys Thr Cys Pro Lys Leu Thr Cys Ala
145                 150                 155                 160

Phe Pro Val Ser Val Pro Asp Ser Cys Cys Arg Val Cys Arg Gly Asp
                165                 170                 175

Ala Glu Leu Ser Trp Glu His Ala Asp Gly Asp Ile Phe Arg Gln Pro
            180                 185                 190

Ala Asn Arg Glu Ala Arg His Ser Tyr Leu Arg Ser Pro Tyr Asp Pro
        195                 200                 205

Pro Pro Asn Arg Gln Ala Gly Gly Leu Pro Arg Phe Pro Gly Ser Arg
```

-continued

```
            210                 215                 220
Ser His Arg Gly Ala Val Ile Asp Ser Gln Gln Ala Ser Gly Thr Ile
225                 230                 235                 240

Val Gln Ile Val Ile Asn Asn Lys His Lys His Gly Gln Val Cys Val
                245                 250                 255

Ser Asn Gly Lys Thr Tyr Ser His Gly Glu Ser Trp His Pro Asn Leu
                260                 265                 270

Arg Ala Phe Gly Ile Val Glu Cys Val Leu Cys Thr Cys Asn Val Thr
            275                 280                 285

Lys Gln Glu Cys Lys Lys Ile His Cys Pro Asn Arg Tyr Pro Cys Lys
290                 295                 300

Tyr Pro Gln Lys Ile Asp Gly Lys Cys Cys Lys Val Cys Pro Gly Lys
305                 310                 315                 320

Lys Ala Lys Gly Ala Leu Ala Gly Gly Pro Ala Phe Gly
                325                 330

<210> SEQ ID NO 3
<211> LENGTH: 311
<212> TYPE: PRT
<213> ORGANISM: Mus musculus

<400> SEQUENCE: 3

Glu Gln Val Lys His Ser Asp Thr Tyr Cys Val Phe Gln Asp Lys Lys
1               5                   10                  15

Tyr Arg Val Gly Glu Lys Trp His Pro Tyr Leu Glu Pro Tyr Gly Leu
                20                  25                  30

Val Tyr Cys Val Asn Cys Ile Cys Ser Glu Asn Gly Asn Val Leu Cys
            35                  40                  45

Ser Arg Val Arg Cys Pro Ser Leu His Cys Leu Ser Pro Val His Ile
        50                  55                  60

Pro His Leu Cys Cys Pro Arg Cys Pro Asp Ser Leu Pro Pro Val Asn
65                  70                  75                  80

Asn Lys Val Thr Ser Lys Ser Cys Glu Tyr Asn Gly Thr Thr Tyr Gln
                85                  90                  95

His Gly Glu Leu Phe Ile Ala Glu Gly Leu Phe Gln Asn Arg Gln Pro
                100                 105                 110

Asn Gln Cys Ser Gln Cys Ser Cys Ser Glu Gly Asn Val Tyr Cys Gly
            115                 120                 125

Leu Lys Thr Cys Pro Lys Leu Thr Cys Ala Phe Pro Val Ser Val Pro
        130                 135                 140

Asp Ser Cys Cys Arg Val Cys Arg Gly Asp Ala Glu Leu Ser Trp Glu
145                 150                 155                 160

His Ala Asp Gly Asp Ile Phe Arg Gln Pro Ala Asn Arg Glu Ala Arg
                165                 170                 175

His Ser Tyr Leu Arg Ser Pro Tyr Asp Pro Pro Asn Arg Gln Ala
            180                 185                 190

Gly Gly Leu Pro Arg Phe Pro Gly Ser Arg Ser His Arg Gly Ala Val
        195                 200                 205

Ile Asp Ser Gln Gln Ala Ser Gly Thr Ile Val Gln Ile Val Ile Asn
210                 215                 220

Asn Lys His Lys His Gly Gln Val Cys Val Ser Asn Gly Lys Thr Tyr
225                 230                 235                 240

Ser His Gly Glu Ser Trp His Pro Asn Leu Arg Ala Phe Gly Ile Val
                245                 250                 255
```

```
Glu Cys Val Leu Cys Thr Cys Asn Val Thr Lys Gln Glu Cys Lys Lys
            260                 265                 270

Ile His Cys Pro Asn Arg Tyr Pro Cys Lys Tyr Pro Gln Lys Ile Asp
            275                 280                 285

Gly Lys Cys Cys Lys Val Cys Pro Gly Lys Lys Ala Lys Gly Ala Leu
            290                 295                 300

Ala Gly Gly Pro Ala Phe Gly
305                 310

<210> SEQ ID NO 4
<211> LENGTH: 3827
<212> TYPE: DNA
<213> ORGANISM: Rattus norvegicus
<220> FEATURE:
<221> NAME/KEY: CDS
<222> LOCATION: (142)..(1287)
<220> FEATURE:
<221> NAME/KEY: sig_peptide
<222> LOCATION: (142)..(207)

<400> SEQUENCE: 4
ccacgcgtcc gagcgcccca gggagctcag agcgtgtgca agcgtggcag aaggaagagg      60
ccagtgccca gctttagccc accagtccta ggagtctctg agctgcattt tgcagtagct     120
caaaggagaa gagagtggaa a atg gaa ggc ata aaa tat atc gcc tcc ttg      171
                        Met Glu Gly Ile Lys Tyr Ile Ala Ser Leu
                          1               5                  10 gtt ttc ttc ttt gtt ttc ctg gaa gca agc aaa aca gag cca gta aaa      219
Val Phe Phe Phe Val Phe Leu Glu Ala Ser Lys Thr Glu Pro Val Lys
             15                  20                  25 cac tca gag aca tat tgc atg ttt caa gac aag aag tat aga gtt ggt      267
His Ser Glu Thr Tyr Cys Met Phe Gln Asp Lys Lys Tyr Arg Val Gly
         30                  35                  40 gag aaa tgg cat ccc tac ctg gaa cca tat gga ctg gtt tac tgt gtg      315
Glu Lys Trp His Pro Tyr Leu Glu Pro Tyr Gly Leu Val Tyr Cys Val
     45                  50                  55 aac tgc atc tgc tca gag aat ggg aat gtg ctt tgc agc cga gtc aga      363
Asn Cys Ile Cys Ser Glu Asn Gly Asn Val Leu Cys Ser Arg Val Arg
 60                  65                  70 tgt cca act ctt cat tgc ctt tca ccc gtg cat att cct cat ctg tgt      411
Cys Pro Thr Leu His Cys Leu Ser Pro Val His Ile Pro His Leu Cys
 75                  80                  85                  90 tgc ccc cgt tgc cca gac tcc tta cca ccg atg aac aat aag gtg acc      459
Cys Pro Arg Cys Pro Asp Ser Leu Pro Pro Met Asn Asn Lys Val Thr
                 95                 100                 105 agc aag tcc tgc gaa tac aat ggg acc acc tac caa cac gga gag ctc      507
Ser Lys Ser Cys Glu Tyr Asn Gly Thr Thr Tyr Gln His Gly Glu Leu
            110                 115                 120 ttc ata gct gaa ggg ctc ttt cag aac cgg cag ccc aat cag tgc agt      555
Phe Ile Ala Glu Gly Leu Phe Gln Asn Arg Gln Pro Asn Gln Cys Ser
        125                 130                 135 cag tgc agc tgc tcg gag ggg aat gtg tat tgt ggt ctc aag act tgc      603
Gln Cys Ser Cys Ser Glu Gly Asn Val Tyr Cys Gly Leu Lys Thr Cys
    140                 145                 150 ccc aaa ctg acc tgt gca ttc cca gtc tct gtt cca gat tcc tgc tgc      651
Pro Lys Leu Thr Cys Ala Phe Pro Val Ser Val Pro Asp Ser Cys Cys
155                 160                 165                 170 cga gta tgc aga ggg gat gga gaa tta tca tgg gaa cat tct gat gct      699
Arg Val Cys Arg Gly Asp Gly Glu Leu Ser Trp Glu His Ser Asp Ala
                175                 180                 185 gat atc ttc cgg caa cct gcc aac aga gaa gca aga cat tct tac ctc      747
```

```
                Asp Ile Phe Arg Gln Pro Ala Asn Arg Glu Ala Arg His Ser Tyr Leu
                                190                 195                 200 cgt tcc ccc tac gat cct cca cca agc aga caa gct gga ggt ctt cct         795
Arg Ser Pro Tyr Asp Pro Pro Pro Ser Arg Gln Ala Gly Gly Leu Pro
            205                 210                 215 cgc ttt gct ggg agc aga agt cac cgg gga gct gtc att gat tct cag         843
Arg Phe Ala Gly Ser Arg Ser His Arg Gly Ala Val Ile Asp Ser Gln
        220                 225                 230 caa gca tca ggg acc atc gtg cag atc gtc atc aat aac aag cac aaa         891
Gln Ala Ser Gly Thr Ile Val Gln Ile Val Ile Asn Asn Lys His Lys
235                 240                 245                 250 cat gga caa gtg tgt gtt tcc aat gga aag acc tat tct cac gga gaa         939
His Gly Gln Val Cys Val Ser Asn Gly Lys Thr Tyr Ser His Gly Glu
                255                 260                 265 tcc tgg cat tca aat cta cga gct ttt ggc att gtg gaa tgt gtt cta         987
Ser Trp His Ser Asn Leu Arg Ala Phe Gly Ile Val Glu Cys Val Leu
            270                 275                 280 tgc act tgt aat gtc acc aag caa gaa tgt aag aaa atc cac tgc ccc        1035
Cys Thr Cys Asn Val Thr Lys Gln Glu Cys Lys Lys Ile His Cys Pro
        285                 290                 295 aat cga tac ccc tgc aag tat cct caa aaa tta gat gga aag tgc tgc        1083
Asn Arg Tyr Pro Cys Lys Tyr Pro Gln Lys Leu Asp Gly Lys Cys Cys
300                 305                 310 aag gtg tgc cca gaa gaa cct cca agt caa aac ttt gac agc aaa ggt        1131
Lys Val Cys Pro Glu Glu Pro Pro Ser Gln Asn Phe Asp Ser Lys Gly
                315                 320                 325                 330 tcc ttt tgt gga gaa gaa acc atg cct gta tat gag gct gtc ctc gtg        1179
Ser Phe Cys Gly Glu Glu Thr Met Pro Val Tyr Glu Ala Val Leu Val
                335                 340                 345 gag gat gga gag aca gcc aga aaa gta gca ctg gag acc gag aaa cca        1227
Glu Asp Gly Glu Thr Ala Arg Lys Val Ala Leu Glu Thr Glu Lys Pro
            350                 355                 360 cct caa gta gta ggt tca cgt ttg gac tat tcg aaa ggg cat tct cca        1275
Pro Gln Val Val Gly Ser Arg Leu Asp Tyr Ser Lys Gly His Ser Pro
        365                 370                 375 gca ctt cca cat tgagaagatt tccaaggaga tgtttgggga gctccatcat            1327
Ala Leu Pro His
        380 ttcaagctgg tgactcgaac caccatgaac cagtggaaga tcttcgctga aggagaagct      1387 cagctcagcc agatgtgctc aagtcgggtg tgcagaacag aactggaaga tttggtccag      1447 gttttgtacc tggagagacc tgaaaaggac cactgttaga caaacagtc aggattgaat       1507 agtatcaatc aaggaaaccc aagctgcagc tggactgccg gcttactta cttaagtcaa       1567 cagtgctcca aaaccccaaa gtcaacctca gtcaaattat ccagtcacag cacaccttgt     1627 tcctctatgt gcagcggtgt gccagccctc aaacatctcc tgtaaagaga atagaggagt    1687 ctttaatggt ttctggggt gggggagaaa gggataggac tttgtggtac agctctattt     1747 tctctgagaa tcacatttat ttgcaggtta agtagaaaa gaaaaccact ttttagggat     1807 tctatgtaga aagtcacaag agagagagag agagaaattg ctgagtttga gttggatcat    1867 gccaaacaaa tttgtgtgaa atacttttg aatgttcaag tgtcttccct actttaaaaa     1927 tgttattcag ttggtggttg aacagtcagg tgattatgga gcacatacct ataatatgtg   1987 gagacctggg ttctagtctc agaactgaca aaaaatttc tatcctcata tctcacatgc    2047 acacacacac acacacacac acacacacac acacacacac acacacacac acagcacacg   2107 aaactgcatt tctttctggc tcctaaacac ctttgtggtt gttcgtatcc agggaaacaa    2167
```

```
actaaaaatg tatgcaaaaa actctgccct caagcctttg aggcaggttg taagaaatca      2227
gccatagtct tagagtgaag aatgccattt gtgggtcttg tttccttcga agtactaaat      2287
acattttgcc tagtaatatc acttctcttt tcttatctgg caccccccatt aggaaggtag     2347 aatttggaga actcatcaga aactaaattt attccaaaca aaatgacaat agaagaatat      2407
aactgataaa aaataaaata gtccattttt tgttttggtt ttacagctat aaatctaact      2467
gattaatagg ctaatgatgc tcactaattt tcttgaggca atagtcacct aggcagacac      2527
tttaggttga cacttttatt ctaaaagcct ttttaagggt aatttcctac tttgattaca      2587
ggagttgaaa tgtaacttt caaaaaggct caatccttac aagcttctca acatcagttc       2647
ttctgttaag tgctactgtt cattcacaga gctgagaatt ctggcaaaga tctttgtccc      2707
aacccttcct aatatccttg ccttattctt gagcatgggt tgcagcaggg attgtgacag      2767
cactacttct aaaatgttca tttgcagccc agtgcctcaa catcaattt ccttcctgag       2827 gcttggcttt agaaatcacc ttttggaaaa actataacta ttccctagca aagatcatag      2887
gttcactgga tctgtccatc tgccgagcat gaatgaactc acatgagtac taagaaatgt      2947
gaagatcaag aaattctata tttcccactc taagtgagaa acatgatag gaaaagtat        3007 gaagagtctg gtctttacta gaacctgaca gagaagggaa ggctttgggg ccagggcttc      3067
atgagacaaa cttcctgcca gccaattaca cattctccca agaagagaag catagggcgt      3127
cctgggctgc aaagacactg aacattattg aagatgtgat ggggcaatgc caaccctctg      3187
ctgcttccct cttggaggaa acactatttc cagagtgcgg agatcaatca caggtcctga     3247
aggaaagtgg tgattcctgt gctagacgat tcacccgcag ggaaggtggt gattcccgtg      3307
ctagatgatt cactcacaaa ccttcccgcc caggtgttct ctgaaagctt agcctcaagg      3367
gaacacctaa agagctcccc tacctacata aacccctgcc tccaagtgta ggaactcacc      3427
tttctaaagc gctgtgggaa gcaggaactg ggcatctgtg ctaagtcaat gtagaatttc      3487
tccagcgttt taatgctggg tagaatatag agcataggg aaaggggcca aactgcctat       3547
agttagtaga gaaaatgaa tgtggttctt ttgtgcattt atgtgtatca taaacacttg       3607
ggaaagcaaa aaccataagc accattttgc aactttatcc attttccagt tagctcatgt      3667
aaacgagcac gaataacaaa acagtattac tctttcgcac ttctcacagg acatgtaccc      3727
aaatacggta cttatttatg tagtcactgt gtttcaggac ttttacgtta ataaaatttt      3787
tatttaaaat tttaaaaaaa aaaaaaaaaa aaaaaaaaa                             3827
```

<210> SEQ ID NO 5
<211> LENGTH: 382
<212> TYPE: PRT
<213> ORGANISM: Rattus norvegicus

<400> SEQUENCE: 5

```
Met Glu Gly Ile Lys Tyr Ile Ala Ser Leu Val Phe Phe Val Phe
 1               5                  10                  15

Leu Glu Ala Ser Lys Thr Glu Pro Val Lys His Ser Glu Thr Tyr Cys
                 20                  25                  30

Met Phe Gln Asp Lys Lys Tyr Arg Val Gly Glu Lys Trp His Pro Tyr
             35                  40                  45

Leu Glu Pro Tyr Gly Leu Val Tyr Cys Val Asn Cys Ile Cys Ser Glu
         50                  55                  60

Asn Gly Asn Val Leu Cys Ser Arg Val Arg Cys Pro Thr Leu His Cys
 65                  70                  75                  80
```

```
Leu Ser Pro Val His Ile Pro His Leu Cys Cys Pro Arg Cys Pro Asp
                 85                  90                  95

Ser Leu Pro Pro Met Asn Asn Lys Val Thr Ser Lys Ser Cys Glu Tyr
            100                 105                 110

Asn Gly Thr Thr Tyr Gln His Gly Glu Leu Phe Ile Ala Glu Gly Leu
        115                 120                 125

Phe Gln Asn Arg Gln Pro Asn Gln Cys Ser Gln Cys Ser Cys Ser Glu
130                 135                 140

Gly Asn Val Tyr Cys Gly Leu Lys Thr Cys Pro Lys Leu Thr Cys Ala
145                 150                 155                 160

Phe Pro Val Ser Val Pro Asp Ser Cys Cys Arg Val Cys Arg Gly Asp
                165                 170                 175

Gly Glu Leu Ser Trp Glu His Ser Asp Ala Asp Ile Phe Arg Gln Pro
            180                 185                 190

Ala Asn Arg Glu Ala Arg His Ser Tyr Leu Arg Ser Pro Tyr Asp Pro
        195                 200                 205

Pro Pro Ser Arg Gln Ala Gly Gly Leu Pro Arg Phe Ala Gly Ser Arg
210                 215                 220

Ser His Arg Gly Ala Val Ile Asp Ser Gln Ala Ser Gly Thr Ile
225                 230                 235                 240

Val Gln Ile Val Ile Asn Asn Lys His Lys His Gly Gln Val Cys Val
                245                 250                 255

Ser Asn Gly Lys Thr Tyr Ser His Gly Glu Ser Trp His Ser Asn Leu
            260                 265                 270

Arg Ala Phe Gly Ile Val Glu Cys Val Leu Cys Thr Cys Asn Val Thr
        275                 280                 285

Lys Gln Glu Cys Lys Lys Ile His Cys Pro Asn Arg Tyr Pro Cys Lys
290                 295                 300

Tyr Pro Gln Lys Leu Asp Gly Lys Cys Cys Lys Val Cys Pro Glu Glu
305                 310                 315                 320

Pro Pro Ser Gln Asn Phe Asp Ser Lys Gly Ser Phe Cys Gly Glu Glu
                325                 330                 335

Thr Met Pro Val Tyr Glu Ala Val Leu Val Glu Asp Gly Glu Thr Ala
            340                 345                 350

Arg Lys Val Ala Leu Glu Thr Glu Lys Pro Pro Gln Val Val Gly Ser
        355                 360                 365

Arg Leu Asp Tyr Ser Lys Gly His Ser Pro Ala Leu Pro His
370                 375                 380

<210> SEQ ID NO 6
<211> LENGTH: 360
<212> TYPE: PRT
<213> ORGANISM: Rattus norvegicus

<400> SEQUENCE: 6

Glu Pro Val Lys His Ser Glu Thr Tyr Cys Met Phe Gln Asp Lys Lys
1               5                   10                  15

Tyr Arg Val Gly Glu Lys Trp His Pro Tyr Leu Glu Pro Tyr Gly Leu
            20                  25                  30

Val Tyr Cys Val Asn Cys Ile Cys Ser Glu Asn Gly Asn Val Leu Cys
        35                  40                  45

Ser Arg Val Arg Cys Pro Thr Leu His Cys Leu Ser Pro Val His Ile
    50                  55                  60

Pro His Leu Cys Cys Pro Arg Cys Pro Asp Ser Leu Pro Pro Met Asn
65                  70                  75                  80
```

| | | | | | | | | | | | |
|---|---|---|---|---|---|---|---|---|---|---|---|
|Asn|Lys|Val|Thr|Ser|Lys|Ser|Cys|Glu|Tyr|Asn|Gly|Thr|Thr|Tyr|Gln|
| | | | |85| | | | |90| | | | |95| |

His Gly Glu Leu Phe Ile Ala Glu Gly Leu Phe Gln Asn Arg Gln Pro
              100                 105                 110

Asn Gln Cys Ser Gln Cys Ser Cys Ser Glu Gly Asn Val Tyr Cys Gly
              115                 120                 125

Leu Lys Thr Cys Pro Lys Leu Thr Cys Ala Phe Pro Val Ser Val Pro
        130                 135                 140

Asp Ser Cys Cys Arg Val Cys Arg Gly Asp Gly Glu Leu Ser Trp Glu
145                 150                 155                 160

His Ser Asp Ala Asp Ile Phe Arg Gln Pro Ala Asn Arg Glu Ala Arg
                165                 170                 175

His Ser Tyr Leu Arg Ser Pro Tyr Asp Pro Pro Ser Arg Gln Ala
            180                 185                 190

Gly Gly Leu Pro Arg Phe Ala Gly Ser Arg Ser His Arg Gly Ala Val
            195                 200                 205

Ile Asp Ser Gln Gln Ala Ser Gly Thr Ile Val Gln Ile Val Ile Asn
    210                 215                 220

Asn Lys His Lys His Gly Gln Val Cys Val Ser Asn Gly Lys Thr Tyr
225                 230                 235                 240

Ser His Gly Glu Ser Trp His Ser Asn Leu Arg Ala Phe Gly Ile Val
                245                 250                 255

Glu Cys Val Leu Cys Thr Cys Asn Val Thr Lys Gln Glu Cys Lys Lys
            260                 265                 270

Ile His Cys Pro Asn Arg Tyr Pro Cys Lys Tyr Pro Gln Lys Leu Asp
        275                 280                 285

Gly Lys Cys Cys Lys Val Cys Pro Glu Glu Pro Ser Gln Asn Phe
    290                 295                 300

Asp Ser Lys Gly Ser Phe Cys Gly Glu Glu Thr Met Pro Val Tyr Glu
305                 310                 315                 320

Ala Val Leu Val Glu Asp Gly Glu Thr Ala Arg Lys Val Ala Leu Glu
                325                 330                 335

Thr Glu Lys Pro Pro Gln Val Val Gly Ser Arg Leu Asp Tyr Ser Lys
            340                 345                 350

Gly His Ser Pro Ala Leu Pro His
        355                 360

<210> SEQ ID NO 7
<211> LENGTH: 1496
<212> TYPE: DNA
<213> ORGANISM: Homo sapiens
<220> FEATURE:
<221> NAME/KEY: CDS
<222> LOCATION: (132)..(1487)
<220> FEATURE:
<221> NAME/KEY: sig_peptide
<222> LOCATION: (132)..(185)
<220> FEATURE:
<221> NAME/KEY: sig_peptide
<222> LOCATION: (132)..(194)

<400> SEQUENCE: 7
tagccagacc tcggacgaga gcgccccggg gagctcggag cgcgtgcacg cgtggcagac      60
ggagaaggcc agtgcccagc ttgaaggttc tgccaccttt tgcagtggtc caaatgagaa     120
aaaagtggaa a atg gga ggc atg aaa tac atc ttt tcg ttg ttg ttc ttt     170
            Met Gly Gly Met Lys Tyr Ile Phe Ser Leu Leu Phe Phe
              1               5                  10

-continued

| | | |
|---|---|---|
| ctt ttg cta gaa gga ggc aaa aca gag caa gta aaa cat tca gag aca<br>Leu Leu Leu Glu Gly Gly Lys Thr Glu Gln Val Lys His Ser Glu Thr<br>    15                      20                      25 | | 218 |
| tat tgc atg ttt caa gac aag aag tac aga gtg ggt gag aga tgg cat<br>Tyr Cys Met Phe Gln Asp Lys Lys Tyr Arg Val Gly Glu Arg Trp His<br>30                      35                      40                      45 | | 266 |
| cct tac ctg gaa cct tat ggg ttg gtt tac tgc gtg aac tgc atc tgc<br>Pro Tyr Leu Glu Pro Tyr Gly Leu Val Tyr Cys Val Asn Cys Ile Cys<br>                    50                      55                      60 | | 314 |
| tca gag aat ggg aat gtg ctt tgc agc cga gtc aga tgt cca aat gtt<br>Ser Glu Asn Gly Asn Val Leu Cys Ser Arg Val Arg Cys Pro Asn Val<br>                  65                      70                      75 | | 362 |
| cat tgc ctt tct cct gtg cat att cct cat ctg tgc tgc cct cgc tgc<br>His Cys Leu Ser Pro Val His Ile Pro His Leu Cys Cys Pro Arg Cys<br>        80                      85                      90 | | 410 |
| cca gaa gac tcc tta ccc cca gtg aac aat aag gtg acc agc aag tct<br>Pro Glu Asp Ser Leu Pro Pro Val Asn Asn Lys Val Thr Ser Lys Ser<br>        95                      100                    105 | | 458 |
| tgc gag tac aat ggg aca act tac caa cat gga gag ctg ttc gta gct<br>Cys Glu Tyr Asn Gly Thr Thr Tyr Gln His Gly Glu Leu Phe Val Ala<br>110                      115                    120                    125 | | 506 |
| gaa ggg ctc ttt cag aat cgg caa ccc aat caa tgc acc cag tgc agc<br>Glu Gly Leu Phe Gln Asn Arg Gln Pro Asn Gln Cys Thr Gln Cys Ser<br>                  130                    135                    140 | | 554 |
| tgt tcg gag gga aac gtg tat tgt ggt ctc aag act tgc ccc aaa tta<br>Cys Ser Glu Gly Asn Val Tyr Cys Gly Leu Lys Thr Cys Pro Lys Leu<br>                  145                    150                    155 | | 602 |
| acc tgt gcc ttc cca gtc tct gtt cca gat tcc tgc tgc cgg gta tgc<br>Thr Cys Ala Phe Pro Val Ser Val Pro Asp Ser Cys Cys Arg Val Cys<br>160                      165                    170 | | 650 |
| aga gga gat gga gaa ctg tca tgg gaa cat tct gat ggt gat atc ttc<br>Arg Gly Asp Gly Glu Leu Ser Trp Glu His Ser Asp Gly Asp Ile Phe<br>        175                      180                    185 | | 698 |
| cgg caa cct gcc aac aga gaa gca aga cat tct tac cac cgc tct cac<br>Arg Gln Pro Ala Asn Arg Glu Ala Arg His Ser Tyr His Arg Ser His<br>190                      195                    200                    205 | | 746 |
| tat gat cct cca cca agc cga cag gct gga ggt ctg tcc cgc ttt cct<br>Tyr Asp Pro Pro Pro Ser Arg Gln Ala Gly Gly Leu Ser Arg Phe Pro<br>                  210                    215                    220 | | 794 |
| ggg gcc aga agt cac cgg gga gct ctt atg gat tcc cag caa gca tca<br>Gly Ala Arg Ser His Arg Gly Ala Leu Met Asp Ser Gln Gln Ala Ser<br>                225                    230                    235 | | 842 |
| gga acc att gtg caa att gtc atc aat aac aaa cac aag cat gga caa<br>Gly Thr Ile Val Gln Ile Val Ile Asn Asn Lys His Lys His Gly Gln<br>240                      245                    250 | | 890 |
| gtg tgt gtt tcc aat gga aag acc tat tct cat ggc gag tcc tgg cac<br>Val Cys Val Ser Asn Gly Lys Thr Tyr Ser His Gly Glu Ser Trp His<br>255                      260                    265 | | 938 |
| cca aac ctc cgg gca ttt ggc att gtg gag tgt gta cta tgt act tgt<br>Pro Asn Leu Arg Ala Phe Gly Ile Val Glu Cys Val Leu Cys Thr Cys<br>270                      275                    280                    285 | | 986 |
| aat gtc acc aag caa gag tgt aag aaa atc cac tgc ccc aat cga tac<br>Asn Val Thr Lys Gln Glu Cys Lys Lys Ile His Cys Pro Asn Arg Tyr<br>                  290                    295                    300 | | 1034 |
| ccc tgc aag tat cct caa aaa ata gac gga aag tgc tgc aag gtg tgt<br>Pro Cys Lys Tyr Pro Gln Lys Ile Asp Gly Lys Cys Cys Lys Val Cys<br>                    305                    310                    315 | | 1082 |
| cca ggt aaa aaa gca aaa gaa gaa ctt cca ggc caa agc ttt gac aat<br>Pro Gly Lys Lys Ala Lys Glu Glu Leu Pro Gly Gln Ser Phe Asp Asn | | 1130 |

```
                320                 325                 330
aaa ggc tac ttc tgc ggg gaa gaa acg atg cct gtg tat gag tct gta      1178
Lys Gly Tyr Phe Cys Gly Glu Glu Thr Met Pro Val Tyr Glu Ser Val
        335                 340                 345 ttc atg gag gat ggg gag aca acc aga aaa ata gca ctg gag act gag      1226
Phe Met Glu Asp Gly Glu Thr Thr Arg Lys Ile Ala Leu Glu Thr Glu
350                 355                 360                 365 aga cca cct cag gta gag gtc cac gtt tgg act att cga aag ggc att      1274
Arg Pro Pro Gln Val Glu Val His Val Trp Thr Ile Arg Lys Gly Ile
                370                 375                 380 ctc cag cac ttc cat att gag aag atc tcc aag agg atg ttt gag gag      1322
Leu Gln His Phe His Ile Glu Lys Ile Ser Lys Arg Met Phe Glu Glu
            385                 390                 395 ctt cct cac ttc aag ctg gtg acc aga aca acc ctg agc cag tgg aag      1370
Leu Pro His Phe Lys Leu Val Thr Arg Thr Thr Leu Ser Gln Trp Lys
        400                 405                 410 atc ttc acc gaa gga gaa gct cag atc agc cag atg tgt tca agt cgt      1418
Ile Phe Thr Glu Gly Glu Ala Gln Ile Ser Gln Met Cys Ser Ser Arg
    415                 420                 425 gta tgc aga aca gag ctt gaa gat tta gtc aag gtt ttg tac ctg gag      1466
Val Cys Arg Thr Glu Leu Glu Asp Leu Val Lys Val Leu Tyr Leu Glu
430                 435                 440                 445 aga tct gaa aag ggc cac tgt taggcaagg                                1496
Arg Ser Glu Lys Gly His Cys
                450

<210> SEQ ID NO 8
<211> LENGTH: 452
<212> TYPE: PRT
<213> ORGANISM: Homo sapiens

<400> SEQUENCE: 8

Met Gly Gly Met Lys Tyr Ile Phe Ser Leu Leu Phe Phe Leu Leu Leu
1               5                   10                  15

Glu Gly Gly Lys Thr Glu Gln Val Lys His Ser Glu Thr Tyr Cys Met
            20                  25                  30

Phe Gln Asp Lys Lys Tyr Arg Val Gly Glu Arg Trp His Pro Tyr Leu
        35                  40                  45

Glu Pro Tyr Gly Leu Val Tyr Cys Val Asn Cys Ile Cys Ser Glu Asn
    50                  55                  60

Gly Asn Val Leu Cys Ser Arg Val Arg Cys Pro Asn Val His Cys Leu
65                  70                  75                  80

Ser Pro Val His Ile Pro His Leu Cys Cys Pro Arg Cys Pro Glu Asp
                85                  90                  95

Ser Leu Pro Pro Val Asn Asn Lys Val Thr Ser Lys Ser Cys Glu Tyr
            100                 105                 110

Asn Gly Thr Thr Tyr Gln His Gly Glu Leu Phe Val Ala Glu Gly Leu
        115                 120                 125

Phe Gln Asn Arg Gln Pro Asn Gln Cys Thr Gln Cys Ser Cys Ser Glu
    130                 135                 140

Gly Asn Val Tyr Cys Gly Leu Lys Thr Cys Pro Lys Leu Thr Cys Ala
145                 150                 155                 160

Phe Pro Val Ser Val Pro Asp Ser Cys Cys Arg Val Cys Arg Gly Asp
                165                 170                 175

Gly Glu Leu Ser Trp Glu His Ser Asp Gly Asp Ile Phe Arg Gln Pro
            180                 185                 190

Ala Asn Arg Glu Ala Arg His Ser Tyr His Arg Ser His Tyr Asp Pro
```

```
                195                 200                 205
Pro Pro Ser Arg Gln Ala Gly Gly Leu Ser Arg Phe Pro Gly Ala Arg
    210                 215                 220

Ser His Arg Gly Ala Leu Met Asp Ser Gln Gln Ala Ser Gly Thr Ile
225                 230                 235                 240

Val Gln Ile Val Ile Asn Asn Lys His Lys His Gly Gln Val Cys Val
                245                 250                 255

Ser Asn Gly Lys Thr Tyr Ser His Gly Glu Ser Trp His Pro Asn Leu
            260                 265                 270

Arg Ala Phe Gly Ile Val Glu Cys Val Leu Cys Thr Cys Asn Val Thr
        275                 280                 285

Lys Gln Glu Cys Lys Lys Ile His Cys Pro Asn Arg Tyr Pro Cys Lys
    290                 295                 300

Tyr Pro Gln Lys Ile Asp Gly Lys Cys Cys Lys Val Cys Pro Gly Lys
305                 310                 315                 320

Lys Ala Lys Glu Glu Leu Pro Gly Gln Ser Phe Asp Asn Lys Gly Tyr
                325                 330                 335

Phe Cys Gly Glu Glu Thr Met Pro Val Tyr Glu Ser Val Phe Met Glu
            340                 345                 350

Asp Gly Glu Thr Thr Arg Lys Ile Ala Leu Glu Thr Glu Arg Pro Pro
        355                 360                 365

Gln Val Glu Val His Val Trp Thr Ile Arg Lys Gly Ile Leu Gln His
    370                 375                 380

Phe His Ile Glu Lys Ile Ser Lys Arg Met Phe Glu Glu Leu Pro His
385                 390                 395                 400

Phe Lys Leu Val Thr Arg Thr Thr Leu Ser Gln Trp Lys Ile Phe Thr
                405                 410                 415

Glu Gly Glu Ala Gln Ile Ser Gln Met Cys Ser Ser Arg Val Cys Arg
            420                 425                 430

Thr Glu Leu Glu Asp Leu Val Lys Val Leu Tyr Leu Glu Arg Ser Glu
        435                 440                 445

Lys Gly His Cys
    450

<210> SEQ ID NO 9
<211> LENGTH: 434
<212> TYPE: PRT
<213> ORGANISM: Homo sapiens

<400> SEQUENCE: 9

Gly Lys Thr Glu Gln Val Lys His Ser Glu Thr Tyr Cys Met Phe Gln
  1               5                  10                  15

Asp Lys Lys Tyr Arg Val Gly Glu Arg Trp His Pro Tyr Leu Glu Pro
                 20                  25                  30

Tyr Gly Leu Val Tyr Cys Val Asn Cys Ile Cys Ser Glu Asn Gly Asn
             35                  40                  45

Val Leu Cys Ser Arg Val Arg Cys Pro Asn Val His Cys Leu Ser Pro
         50                  55                  60

Val His Ile Pro His Leu Cys Cys Pro Arg Cys Pro Glu Asp Ser Leu
 65                  70                  75                  80

Pro Pro Val Asn Asn Lys Val Thr Ser Lys Ser Cys Glu Tyr Asn Gly
                 85                  90                  95

Thr Thr Tyr Gln His Gly Glu Leu Phe Val Ala Glu Gly Leu Phe Gln
            100                 105                 110
```

```
Asn Arg Gln Pro Asn Gln Cys Thr Gln Cys Ser Cys Ser Glu Gly Asn
        115                 120                 125

Val Tyr Cys Gly Leu Lys Thr Cys Pro Lys Leu Thr Cys Ala Phe Pro
130                 135                 140

Val Ser Val Pro Asp Ser Cys Cys Arg Val Cys Arg Gly Asp Gly Glu
145                 150                 155                 160

Leu Ser Trp Glu His Ser Asp Gly Asp Ile Phe Arg Gln Pro Ala Asn
                165                 170                 175

Arg Glu Ala Arg His Ser Tyr His Arg Ser His Tyr Asp Pro Pro Pro
                180                 185                 190

Ser Arg Gln Ala Gly Gly Leu Ser Arg Phe Pro Gly Ala Arg Ser His
        195                 200                 205

Arg Gly Ala Leu Met Asp Ser Gln Gln Ala Ser Gly Thr Ile Val Gln
210                 215                 220

Ile Val Ile Asn Asn Lys His Lys His Gly Gln Val Cys Val Ser Asn
225                 230                 235                 240

Gly Lys Thr Tyr Ser His Gly Glu Ser Trp His Pro Asn Leu Arg Ala
                245                 250                 255

Phe Gly Ile Val Glu Cys Val Leu Cys Thr Cys Asn Val Thr Lys Gln
                260                 265                 270

Glu Cys Lys Lys Ile His Cys Pro Asn Arg Tyr Pro Cys Lys Tyr Pro
        275                 280                 285

Gln Lys Ile Asp Gly Lys Cys Cys Lys Val Cys Pro Gly Lys Lys Ala
        290                 295                 300

Lys Glu Glu Leu Pro Gly Gln Ser Phe Asp Asn Lys Gly Tyr Phe Cys
305                 310                 315                 320

Gly Glu Glu Thr Met Pro Val Tyr Glu Ser Val Phe Met Glu Asp Gly
                325                 330                 335

Glu Thr Thr Arg Lys Ile Ala Leu Glu Thr Glu Arg Pro Pro Gln Val
                340                 345                 350

Glu Val His Val Trp Thr Ile Arg Lys Gly Ile Leu Gln His Phe His
        355                 360                 365

Ile Glu Lys Ile Ser Lys Arg Met Phe Glu Glu Leu Pro His Phe Lys
370                 375                 380

Leu Val Thr Arg Thr Thr Leu Ser Gln Trp Lys Ile Phe Thr Glu Gly
385                 390                 395                 400

Glu Ala Gln Ile Ser Gln Met Cys Ser Ser Arg Val Cys Arg Thr Glu
                405                 410                 415

Leu Glu Asp Leu Val Lys Val Leu Tyr Leu Glu Arg Ser Glu Lys Gly
                420                 425                 430

His Cys

<210> SEQ ID NO 10
<211> LENGTH: 431
<212> TYPE: PRT
<213> ORGANISM: Homo sapiens

<400> SEQUENCE: 10

Glu Gln Val Lys His Ser Glu Thr Tyr Cys Met Phe Gln Asp Lys Lys
1               5                   10                  15

Tyr Arg Val Gly Glu Arg Trp His Pro Tyr Leu Glu Pro Tyr Gly Leu
                20                  25                  30

Val Tyr Cys Val Asn Cys Ile Cys Ser Glu Asn Gly Asn Val Leu Cys
            35                  40                  45
```

Ser Arg Val Arg Cys Pro Asn Val His Cys Leu Ser Pro Val His Ile
 50                  55                  60

Pro His Leu Cys Cys Pro Arg Cys Pro Glu Asp Ser Leu Pro Pro Val
 65                  70                  75                  80

Asn Asn Lys Val Thr Ser Lys Ser Cys Glu Tyr Asn Gly Thr Thr Tyr
                 85                  90                  95

Gln His Gly Glu Leu Phe Val Ala Glu Gly Leu Phe Gln Asn Arg Gln
             100                 105                 110

Pro Asn Gln Cys Thr Gln Cys Ser Cys Ser Glu Gly Asn Val Tyr Cys
         115                 120                 125

Gly Leu Lys Thr Cys Pro Lys Leu Thr Cys Ala Phe Pro Val Ser Val
     130                 135                 140

Pro Asp Ser Cys Cys Arg Val Cys Arg Gly Asp Gly Glu Leu Ser Trp
145                 150                 155                 160

Glu His Ser Asp Gly Asp Ile Phe Arg Gln Pro Ala Asn Arg Glu Ala
                165                 170                 175

Arg His Ser Tyr His Arg Ser His Tyr Asp Pro Pro Ser Arg Gln
            180                 185                 190

Ala Gly Gly Leu Ser Arg Phe Pro Gly Ala Arg Ser His Arg Gly Ala
        195                 200                 205

Leu Met Asp Ser Gln Gln Ala Ser Gly Thr Ile Val Gln Ile Val Ile
210                 215                 220

Asn Asn Lys His Lys His Gly Gln Val Cys Val Ser Asn Gly Lys Thr
225                 230                 235                 240

Tyr Ser His Gly Glu Ser Trp His Pro Asn Leu Arg Ala Phe Gly Ile
                245                 250                 255

Val Glu Cys Val Leu Cys Thr Cys Asn Val Thr Lys Gln Glu Cys Lys
            260                 265                 270

Lys Ile His Cys Pro Asn Arg Tyr Pro Cys Lys Tyr Pro Gln Lys Ile
        275                 280                 285

Asp Gly Lys Cys Cys Lys Val Cys Pro Gly Lys Lys Ala Lys Glu Glu
    290                 295                 300

Leu Pro Gly Gln Ser Phe Asp Asn Lys Gly Tyr Phe Cys Gly Glu Glu
305                 310                 315                 320

Thr Met Pro Val Tyr Glu Ser Val Phe Met Glu Asp Gly Glu Thr Thr
                325                 330                 335

Arg Lys Ile Ala Leu Glu Thr Glu Arg Pro Pro Gln Val Glu Val His
            340                 345                 350

Val Trp Thr Ile Arg Lys Gly Ile Leu Gln His Phe His Ile Glu Lys
        355                 360                 365

Ile Ser Lys Arg Met Phe Glu Glu Leu Pro His Phe Lys Leu Val Thr
    370                 375                 380

Arg Thr Thr Leu Ser Gln Trp Lys Ile Phe Thr Glu Gly Glu Ala Gln
385                 390                 395                 400

Ile Ser Gln Met Cys Ser Ser Arg Val Cys Arg Thr Glu Leu Glu Asp
                405                 410                 415

Leu Val Lys Val Leu Tyr Leu Glu Arg Ser Glu Lys Gly His Cys
            420                 425                 430

<210> SEQ ID NO 11
<211> LENGTH: 1341
<212> TYPE: DNA
<213> ORGANISM: Homo sapiens
<220> FEATURE:
<221> NAME/KEY: CDS

```
<222> LOCATION: (1)..(1341)
<220> FEATURE:
<221> NAME/KEY: sig_peptide
<222> LOCATION: (1)..(54)
<220> FEATURE:
<221> NAME/KEY: sig_peptide
<222> LOCATION: (1)..(63)

<400> SEQUENCE: 11 atg gga ggc atg aaa tac atc ttt tcg ttg ttg ttc ttt ctt ttg cta      48
Met Gly Gly Met Lys Tyr Ile Phe Ser Leu Leu Phe Phe Leu Leu Leu
 1               5                  10                  15 gaa gga ggc aaa aca gag caa gta aaa cat tca gag aca tat tgc atg      96
Glu Gly Gly Lys Thr Glu Gln Val Lys His Ser Glu Thr Tyr Cys Met
             20                  25                  30 ttt caa gac aag aag tac aga gtg ggt gag aga tgg cat cct tac ctg     144
Phe Gln Asp Lys Lys Tyr Arg Val Gly Glu Arg Trp His Pro Tyr Leu
         35                  40                  45 gaa cct tat ggg ttg gtt tac tgc gtg aac tgc atc tgc tca gag aat     192
Glu Pro Tyr Gly Leu Val Tyr Cys Val Asn Cys Ile Cys Ser Glu Asn
     50                  55                  60 ggg aat gtg ctt tgc agc cga gtc aga tgt cca aat gtt cat tgc ctt     240
Gly Asn Val Leu Cys Ser Arg Val Arg Cys Pro Asn Val His Cys Leu
 65                  70                  75                  80 tct cct gtg cat att cct cat ctg tgc tgc cct cgc tgc cca gaa gac     288
Ser Pro Val His Ile Pro His Leu Cys Cys Pro Arg Cys Pro Glu Asp
                 85                  90                  95 tcc tta ccc cca gtg aac aat aag gtg acc agc aag tct tgc gag tac     336
Ser Leu Pro Pro Val Asn Asn Lys Val Thr Ser Lys Ser Cys Glu Tyr
            100                 105                 110 aat ggg aca act tac caa cat gga gag ctg ttc gta gct gaa ggg ctc     384
Asn Gly Thr Thr Tyr Gln His Gly Glu Leu Phe Val Ala Glu Gly Leu
        115                 120                 125 ttt cag aat cgg caa ccc aat caa tgc acc cag tgc agc tgt tcg gag     432
Phe Gln Asn Arg Gln Pro Asn Gln Cys Thr Gln Cys Ser Cys Ser Glu
    130                 135                 140 gga aac gtg tat tgt ggt ctc aag act tgc ccc aaa tta acc tgt gcc     480
Gly Asn Val Tyr Cys Gly Leu Lys Thr Cys Pro Lys Leu Thr Cys Ala
145                 150                 155                 160 ttc cca gtc tct gtt cca gat tcc tgc tgc cgg gta tgc aga gga gat     528
Phe Pro Val Ser Val Pro Asp Ser Cys Cys Arg Val Cys Arg Gly Asp
                165                 170                 175 gga gaa ctg tca tgg gaa cat tct gat ggt gat atc ttc cgg caa cct     576
Gly Glu Leu Ser Trp Glu His Ser Asp Gly Asp Ile Phe Arg Gln Pro
            180                 185                 190 gcc aac aga gaa gca aga cat tct tac cac cgc tct cac tat gat cct     624
Ala Asn Arg Glu Ala Arg His Ser Tyr His Arg Ser His Tyr Asp Pro
        195                 200                 205 cca cca agc cga cag gct gga ggt ctg tcc cgc ttt cct ggg gcc aga     672
Pro Pro Ser Arg Gln Ala Gly Gly Leu Ser Arg Phe Pro Gly Ala Arg
    210                 215                 220 agt cac cgg gga gct ctt atg gat tcc cag caa gca tca gga acc att     720
Ser His Arg Gly Ala Leu Met Asp Ser Gln Gln Ala Ser Gly Thr Ile
225                 230                 235                 240 gtg caa att gtc atc aat aac aaa cac aag cat gga caa gtg tgt gtt     768
Val Gln Ile Val Ile Asn Asn Lys His Lys His Gly Gln Val Cys Val
                245                 250                 255 tcc aat gga aag acc tat tct cat ggc gag tcc tgg cac cca aac ctc     816
Ser Asn Gly Lys Thr Tyr Ser His Gly Glu Ser Trp His Pro Asn Leu
            260                 265                 270 cgg gca ttt ggc att gtg gag tgt gtg cta tgt act tgt aat gtc acc     864
```

-continued

| | | | | | | | | | | | | |
|---|---|---|---|---|---|---|---|---|---|---|---|---|
| Arg | Ala | Phe | Gly | Ile | Val | Glu | Cys | Val | Leu | Cys | Thr | Cys | Asn | Val | Thr |
| | | 275 | | | | 280 | | | | 285 | | |

```
aag caa gag tgt aag aaa atc cac tgc ccc aat cga tac ccc tgc aag       912
Lys Gln Glu Cys Lys Lys Ile His Cys Pro Asn Arg Tyr Pro Cys Lys
    290                 295                 300 tat cct caa aaa ata gac gga aag tgc tgc aag gtg tgt cca gaa gaa       960
Tyr Pro Gln Lys Ile Asp Gly Lys Cys Cys Lys Val Cys Pro Glu Glu
305                 310                 315                 320 ctt cca ggc caa agc ttt gac aat aaa ggc tac ttc tgc ggg gaa gaa      1008
Leu Pro Gly Gln Ser Phe Asp Asn Lys Gly Tyr Phe Cys Gly Glu Glu
                325                 330                 335 acg atg cct gtg tat gag tct gta ttc atg gag gat ggg gag aca acc      1056
Thr Met Pro Val Tyr Glu Ser Val Phe Met Glu Asp Gly Glu Thr Thr
            340                 345                 350 aga aaa ata gca ctg gag act gag aga cca cct cag gta gag gtc cac      1104
Arg Lys Ile Ala Leu Glu Thr Glu Arg Pro Pro Gln Val Glu Val His
        355                 360                 365 gtt tgg act att cga aag ggc att ctc cag cac ttc cat att gag aag      1152
Val Trp Thr Ile Arg Lys Gly Ile Leu Gln His Phe His Ile Glu Lys
    370                 375                 380 atc tcc aag agg atg ttt gag gag ctt cct cac ttc aag ctg gtg acc      1200
Ile Ser Lys Arg Met Phe Glu Glu Leu Pro His Phe Lys Leu Val Thr
385                 390                 395                 400 aga aca acc ctg agc cag tgg aag atc ttc acc gaa gga gaa gct cag      1248
Arg Thr Thr Leu Ser Gln Trp Lys Ile Phe Thr Glu Gly Glu Ala Gln
                405                 410                 415 atc agc cag atg tgt tca agt cgt gta tgc aga aca gag ctt gaa gat      1296
Ile Ser Gln Met Cys Ser Ser Arg Val Cys Arg Thr Glu Leu Glu Asp
            420                 425                 430 tta gtc aag gtt ttg tac ctg gag aga tct gaa aag ggc cac tgt          1341
Leu Val Lys Val Leu Tyr Leu Glu Arg Ser Glu Lys Gly His Cys
        435                 440                 445

<210> SEQ ID NO 12
<211> LENGTH: 447
<212> TYPE: PRT
<213> ORGANISM: Homo sapiens

<400> SEQUENCE: 12

Met Gly Gly Met Lys Tyr Ile Phe Ser Leu Leu Phe Phe Leu Leu Leu
 1               5                  10                  15

Glu Gly Gly Lys Thr Glu Gln Val Lys His Ser Glu Thr Tyr Cys Met
            20                  25                  30

Phe Gln Asp Lys Lys Tyr Arg Val Gly Glu Arg Trp His Pro Tyr Leu
        35                  40                  45

Glu Pro Tyr Gly Leu Val Tyr Cys Val Asn Cys Ile Cys Ser Glu Asn
    50                  55                  60

Gly Asn Val Leu Cys Ser Arg Val Arg Cys Pro Asn Val His Cys Leu
65                  70                  75                  80

Ser Pro Val His Ile Pro His Leu Cys Cys Pro Arg Cys Pro Glu Asp
                85                  90                  95

Ser Leu Pro Pro Val Asn Asn Lys Val Thr Ser Lys Ser Cys Glu Tyr
            100                 105                 110

Asn Gly Thr Thr Tyr Gln His Gly Glu Leu Phe Val Ala Glu Gly Leu
        115                 120                 125

Phe Gln Asn Arg Gln Pro Asn Gln Cys Thr Gln Cys Ser Cys Ser Glu
    130                 135                 140

Gly Asn Val Tyr Cys Gly Leu Lys Thr Cys Pro Lys Leu Thr Cys Ala
```

```
                145                 150                 155                 160
Phe Pro Val Ser Val Pro Asp Ser Cys Cys Arg Val Cys Arg Gly Asp
                    165                 170                 175

Gly Glu Leu Ser Trp Glu His Ser Asp Gly Asp Ile Phe Arg Gln Pro
                180                 185                 190

Ala Asn Arg Glu Ala Arg His Ser Tyr His Arg Ser His Tyr Asp Pro
            195                 200                 205

Pro Pro Ser Arg Gln Ala Gly Gly Leu Ser Arg Phe Pro Gly Ala Arg
        210                 215                 220

Ser His Arg Gly Ala Leu Met Asp Ser Gln Gln Ala Ser Gly Thr Ile
225                 230                 235                 240

Val Gln Ile Val Ile Asn Asn Lys His Lys His Gly Gln Val Cys Val
                245                 250                 255

Ser Asn Gly Lys Thr Tyr Ser His Gly Glu Ser Trp His Pro Asn Leu
                260                 265                 270

Arg Ala Phe Gly Ile Val Glu Cys Val Leu Cys Thr Cys Asn Val Thr
                275                 280                 285

Lys Gln Glu Cys Lys Lys Ile His Cys Pro Asn Arg Tyr Pro Cys Lys
            290                 295                 300

Tyr Pro Gln Lys Ile Asp Gly Lys Cys Cys Lys Val Cys Pro Glu Glu
305                 310                 315                 320

Leu Pro Gly Gln Ser Phe Asp Asn Lys Gly Tyr Phe Cys Gly Glu Glu
                325                 330                 335

Thr Met Pro Val Tyr Glu Ser Val Phe Met Glu Asp Gly Glu Thr Thr
                340                 345                 350

Arg Lys Ile Ala Leu Glu Thr Glu Arg Pro Pro Gln Val Glu Val His
            355                 360                 365

Val Trp Thr Ile Arg Lys Gly Ile Leu Gln His Phe His Ile Glu Lys
        370                 375                 380

Ile Ser Lys Arg Met Phe Glu Glu Leu Pro His Phe Lys Leu Val Thr
385                 390                 395                 400

Arg Thr Thr Leu Ser Gln Trp Lys Ile Phe Thr Glu Gly Glu Ala Gln
                405                 410                 415

Ile Ser Gln Met Cys Ser Ser Arg Val Cys Arg Thr Glu Leu Glu Asp
                420                 425                 430

Leu Val Lys Val Leu Tyr Leu Glu Arg Ser Glu Lys Gly His Cys
                435                 440                 445

<210> SEQ ID NO 13
<211> LENGTH: 429
<212> TYPE: PRT
<213> ORGANISM: Homo sapiens

<400> SEQUENCE: 13

Gly Lys Thr Glu Gln Val Lys His Ser Glu Thr Tyr Cys Met Phe Gln
  1               5                  10                  15

Asp Lys Lys Tyr Arg Val Gly Glu Arg Trp His Pro Tyr Leu Glu Pro
                 20                  25                  30

Tyr Gly Leu Val Tyr Cys Val Asn Cys Ile Cys Ser Glu Asn Gly Asn
             35                  40                  45

Val Leu Cys Ser Arg Val Arg Cys Pro Asn Val His Cys Leu Ser Pro
         50                  55                  60

Val His Ile Pro His Leu Cys Cys Pro Arg Cys Pro Glu Asp Ser Leu
 65                  70                  75                  80
```

-continued

```
Pro Pro Val Asn Asn Lys Val Thr Ser Lys Ser Cys Glu Tyr Asn Gly
                 85                  90                  95

Thr Thr Tyr Gln His Gly Glu Leu Phe Val Ala Glu Gly Leu Phe Gln
            100                 105                 110

Asn Arg Gln Pro Asn Gln Cys Thr Gln Cys Ser Cys Ser Glu Gly Asn
        115                 120                 125

Val Tyr Cys Gly Leu Lys Thr Cys Pro Lys Leu Thr Cys Ala Phe Pro
    130                 135                 140

Val Ser Val Pro Asp Ser Cys Cys Arg Val Cys Arg Gly Asp Gly Glu
145                 150                 155                 160

Leu Ser Trp Glu His Ser Asp Gly Asp Ile Phe Arg Gln Pro Ala Asn
                165                 170                 175

Arg Glu Ala Arg His Ser Tyr His Arg Ser His Tyr Asp Pro Pro Pro
            180                 185                 190

Ser Arg Gln Ala Gly Gly Leu Ser Arg Phe Pro Gly Ala Arg Ser His
        195                 200                 205

Arg Gly Ala Leu Met Asp Ser Gln Gln Ala Ser Gly Thr Ile Val Gln
    210                 215                 220

Ile Val Ile Asn Asn Lys His Lys His Gly Gln Val Cys Val Ser Asn
225                 230                 235                 240

Gly Lys Thr Tyr Ser His Gly Glu Ser Trp His Pro Asn Leu Arg Ala
                245                 250                 255

Phe Gly Ile Val Glu Cys Val Leu Cys Thr Cys Asn Val Thr Lys Gln
            260                 265                 270

Glu Cys Lys Lys Ile His Cys Pro Asn Arg Tyr Pro Cys Lys Tyr Pro
        275                 280                 285

Gln Lys Ile Asp Gly Lys Cys Cys Lys Val Cys Pro Glu Glu Leu Pro
    290                 295                 300

Gly Gln Ser Phe Asp Asn Lys Gly Tyr Phe Cys Gly Glu Glu Thr Met
305                 310                 315                 320

Pro Val Tyr Glu Ser Val Phe Met Glu Asp Gly Glu Thr Thr Arg Lys
                325                 330                 335

Ile Ala Leu Glu Thr Glu Arg Pro Pro Gln Val Glu Val His Val Trp
            340                 345                 350

Thr Ile Arg Lys Gly Ile Leu Gln His Phe His Ile Glu Lys Ile Ser
        355                 360                 365

Lys Arg Met Phe Glu Glu Leu Pro His Phe Lys Leu Val Thr Arg Thr
    370                 375                 380

Thr Leu Ser Gln Trp Lys Ile Phe Thr Glu Gly Ala Gln Ile Ser
385                 390                 395                 400

Gln Met Cys Ser Ser Arg Val Cys Arg Thr Leu Glu Asp Leu Val
                405                 410                 415

Lys Val Leu Tyr Leu Glu Arg Ser Glu Lys Gly His Cys
            420                 425

<210> SEQ ID NO 14
<211> LENGTH: 426
<212> TYPE: PRT
<213> ORGANISM: Homo sapiens

<400> SEQUENCE: 14

Glu Gln Val Lys His Ser Glu Thr Tyr Cys Met Phe Gln Asp Lys Lys
  1               5                  10                  15

Tyr Arg Val Gly Glu Arg Trp His Pro Tyr Leu Glu Pro Tyr Gly Leu
             20                  25                  30
```

Val Tyr Cys Val Asn Cys Ile Cys Ser Glu Asn Gly Asn Val Leu Cys
    35                  40                  45

Ser Arg Val Arg Cys Pro Asn Val His Cys Leu Ser Pro Val His Ile
    50                  55                  60

Pro His Leu Cys Cys Pro Arg Cys Pro Glu Asp Ser Leu Pro Pro Val
65                  70                  75                  80

Asn Asn Lys Val Thr Ser Lys Ser Cys Glu Tyr Asn Gly Thr Thr Tyr
                85                  90                  95

Gln His Gly Glu Leu Phe Val Ala Glu Gly Leu Phe Gln Asn Arg Gln
            100                 105                 110

Pro Asn Gln Cys Thr Gln Cys Ser Cys Ser Glu Gly Asn Val Tyr Cys
        115                 120                 125

Gly Leu Lys Thr Cys Pro Lys Leu Thr Cys Ala Phe Pro Val Ser Val
    130                 135                 140

Pro Asp Ser Cys Cys Arg Val Cys Arg Gly Asp Gly Glu Leu Ser Trp
145                 150                 155                 160

Glu His Ser Asp Gly Asp Ile Phe Arg Gln Pro Ala Asn Arg Glu Ala
                165                 170                 175

Arg His Ser Tyr His Arg Ser His Tyr Asp Pro Pro Ser Arg Gln
            180                 185                 190

Ala Gly Gly Leu Ser Arg Phe Pro Gly Ala Arg Ser His Arg Gly Ala
        195                 200                 205

Leu Met Asp Ser Gln Gln Ala Ser Gly Thr Ile Val Gln Ile Val Ile
    210                 215                 220

Asn Asn Lys His Lys His Gly Gln Val Cys Val Ser Asn Gly Lys Thr
225                 230                 235                 240

Tyr Ser His Gly Glu Ser Trp His Pro Asn Leu Arg Ala Phe Gly Ile
                245                 250                 255

Val Glu Cys Val Leu Cys Thr Cys Asn Val Thr Lys Gln Glu Cys Lys
            260                 265                 270

Lys Ile His Cys Pro Asn Arg Tyr Pro Cys Lys Tyr Pro Gln Lys Ile
        275                 280                 285

Asp Gly Lys Cys Cys Lys Val Cys Pro Glu Glu Leu Pro Gly Gln Ser
    290                 295                 300

Phe Asp Asn Lys Gly Tyr Phe Cys Gly Glu Glu Thr Met Pro Val Tyr
305                 310                 315                 320

Glu Ser Val Phe Met Glu Asp Gly Glu Thr Thr Arg Lys Ile Ala Leu
                325                 330                 335

Glu Thr Glu Arg Pro Pro Gln Val Glu Val His Val Trp Thr Ile Arg
            340                 345                 350

Lys Gly Ile Leu Gln His Phe His Ile Glu Lys Ile Ser Lys Arg Met
        355                 360                 365

Phe Glu Glu Leu Pro His Phe Lys Leu Val Thr Arg Thr Thr Leu Ser
    370                 375                 380

Gln Trp Lys Ile Phe Thr Glu Gly Glu Ala Gln Ile Ser Gln Met Cys
385                 390                 395                 400

Ser Ser Arg Val Cys Arg Thr Glu Leu Glu Asp Leu Val Lys Val Leu
                405                 410                 415

Tyr Leu Glu Arg Ser Glu Lys Gly His Cys
            420                 425

<210> SEQ ID NO 15
<211> LENGTH: 948

```
<212> TYPE: PRT
<213> ORGANISM: Mus musculus

<400> SEQUENCE: 15

Met Pro Ser Leu Pro Ala Pro Ala Pro Arg Leu Leu Gly Leu
  1               5                  10                  15

Leu Leu Leu Gly Ser Arg Pro Ala Ser Gly Thr Gly Pro Glu Pro Pro
            20                  25                  30

Ala Leu Pro Ile Arg Ser Glu Lys Glu Pro Leu Pro Val Arg Gly Ala
            35                  40                  45

Ala Gly Cys Ser Phe Gly Gly Lys Val Tyr Ala Leu Asp Glu Thr Trp
 50                  55                  60

His Pro Asp Leu Gly Glu Pro Phe Gly Val Met Arg Cys Val Leu Cys
 65                  70                  75                  80

Ala Cys Glu Ala Pro Gln Trp Ala Arg Arg Gly Arg Gly Pro Gly Arg
                85                  90                  95

Val Ser Cys Lys Asn Ile Lys Pro Gln Cys Pro Thr Leu Ala Cys Arg
                100                 105                 110

Gln Pro Arg Gln Leu Pro Gly His Cys Cys Gln Thr Cys Pro Gln Glu
            115                 120                 125

Arg Ser Asn Leu Asp Pro Gln Pro Ala Gly Leu Val Phe Glu Tyr Pro
130                 135                 140

Arg Asp Pro Glu His Arg Ser Tyr Ser Asp Arg Gly Glu Pro Gly Val
145                 150                 155                 160

Gly Glu Arg Thr Arg Ala Asp Gly His Thr Asp Phe Val Ala Leu Leu
                165                 170                 175

Thr Gly Pro Arg Ser Gln Ala Val Ala Arg Ala Arg Val Ser Leu Leu
            180                 185                 190

Arg Ser Ser Leu Arg Phe Ser Val Ser Tyr Gln Arg Leu Asp Arg Pro
            195                 200                 205

Ser Arg Val Arg Phe Thr Asp Pro Thr Gly Asn Ile Leu Phe Glu His
210                 215                 220

Pro Ala Thr Pro Thr Gln Asp Gly Leu Val Cys Gly Val Trp Arg Ala
225                 230                 235                 240

Val Pro Arg Leu Ser Val Arg Leu Leu Arg Ala Glu Gln Leu Arg Val
                245                 250                 255

Ala Leu Val Thr Ser Thr His Pro Ser Gly Glu Val Trp Gly Pro Leu
            260                 265                 270

Ile Trp Gln Gly Ala Leu Ala Ala Glu Thr Phe Ser Ala Ile Leu Thr
            275                 280                 285

Leu Glu Asp Pro Leu Gln Arg Gly Val Gly Gly Ile Ala Leu Leu Thr
            290                 295                 300

Leu Ser Asp Thr Glu Asp Ser Leu His Phe Leu Leu Phe Arg Gly
305                 310                 315                 320

Leu Leu Gly Gly Leu Ala Gln Ala Pro Leu Lys Leu Gln Ile Leu His
                325                 330                 335

Gln Gly Gln Leu Leu Arg Glu Leu Gln Ala Asn Thr Ser Ala Gln Glu
            340                 345                 350

Pro Gly Phe Ala Glu Val Leu Pro Ser Leu Thr Asp Gln Glu Met Asp
            355                 360                 365

Trp Leu Glu Leu Gly Glu Leu Gln Met Val Leu Glu Lys Ala Gly Gly
            370                 375                 380

Pro Glu Leu Arg Ile Ser Gly Tyr Ile Thr Thr Arg Gln Ser Cys Asp
385                 390                 395                 400
```

-continued

```
Val Leu Gln Ser Val Leu Cys Gly Ala Asp Ala Leu Ile Pro Val Gln
            405                 410                 415
Thr Gly Ala Ala Gly Ser Ala Ser Phe Ile Leu Leu Gly Asn Gly Ser
        420                 425                 430
Leu Ile Tyr Gln Val Gln Val Gly Thr Gly Ser Glu Val Val Ala
        435                 440                 445
Met Thr Leu Glu Thr Lys Pro Gln Arg Lys Asn Gln Arg Thr Val Leu
    450                 455                 460
Cys His Met Ala Gly Leu Gln Pro Gly His Met Ala Val Gly Met
465                 470                 475                 480
Cys Ser Gly Leu Gly Ala Arg Gly Ala His Met Leu Leu Gln Asn Glu
                485                 490                 495
Leu Phe Leu Asn Val Gly Thr Lys Asp Phe Pro Asp Gly Glu Leu Arg
            500                 505                 510
Gly His Val Thr Ala Leu Cys Tyr Ser Gly His Ser Ala Arg Tyr Asp
        515                 520                 525
Arg Leu Pro Val Pro Leu Ala Gly Ala Leu Val Leu Pro Pro Val Arg
    530                 535                 540
Ser Gln Ala Ala Gly His Ala Trp Leu Ser Leu Asp Thr His Cys His
545                 550                 555                 560
Leu His Tyr Glu Val Leu Leu Ala Gly Leu Gly Gly Ser Glu Gln Gly
                565                 570                 575
Thr Val Thr Ala His Leu Leu Gly Pro Pro Gly Met Pro Gly Pro Gln
            580                 585                 590
Arg Leu Leu Lys Gly Phe Tyr Gly Ser Glu Ala Gln Gly Val Val Lys
        595                 600                 605
Asp Leu Glu Pro Val Leu Leu Arg His Leu Ala Gln Gly Thr Ala Ser
    610                 615                 620
Leu Leu Ile Thr Thr Lys Ser Ser Pro Arg Gly Glu Leu Arg Gly Gln
625                 630                 635                 640
Val His Ile Ala Ser Gln Cys Glu Ala Gly Gly Leu Arg Leu Ala Ser
                645                 650                 655
Glu Gly Val Gln Met Pro Leu Ala Pro Asn Gly Glu Ala Ala Thr Ser
            660                 665                 670
Pro Met Leu Pro Ala Gly Pro Gly Pro Glu Ala Pro Val Pro Ala Lys
        675                 680                 685
His Gly Ser Pro Gly Arg Pro Arg Asp Pro Asn Thr Cys Phe Phe Glu
    690                 695                 700
Gly Gln Gln Arg Pro His Gly Ala Arg Trp Ala Pro Asn Tyr Asp Pro
705                 710                 715                 720
Leu Cys Ser Leu Cys Ile Cys Gln Arg Arg Thr Val Ile Cys Asp Pro
                725                 730                 735
Val Val Cys Pro Pro Pro Ser Cys Pro His Pro Val Gln Ala Leu Asp
            740                 745                 750
Gln Cys Cys Pro Val Cys Pro Glu Lys Gln Arg Ser Arg Asp Leu Pro
        755                 760                 765
Ser Leu Pro Asn Leu Glu Pro Gly Glu Gly Cys Tyr Phe Asp Gly Asp
    770                 775                 780
Arg Ser Trp Arg Ala Ala Gly Thr Arg Trp His Pro Val Val Pro Pro
785                 790                 795                 800
Phe Gly Leu Ile Lys Cys Ala Val Cys Thr Cys Lys Gly Ala Thr Gly
                805                 810                 815
```

Glu Val His Cys Glu Lys Val Gln Cys Pro Arg Leu Ala Cys Ala Gln
            820                 825                 830

Pro Val Arg Ala Asn Pro Thr Asp Cys Cys Lys Gln Cys Pro Val Gly
            835                 840                 845

Ser Gly Thr Asn Ala Lys Leu Gly Asp Pro Met Gln Ala Asp Gly Pro
850                 855                 860

Arg Gly Cys Arg Phe Ala Gly Gln Trp Phe Pro Glu Asn Gln Ser Trp
865                 870                 875                 880

His Pro Ser Val Pro Pro Phe Gly Glu Met Ser Cys Ile Thr Cys Arg
            885                 890                 895

Cys Gly Ala Gly Val Pro His Cys Glu Arg Asp Asp Cys Ser Pro Pro
            900                 905                 910

Leu Ser Cys Gly Ser Gly Lys Glu Ser Arg Cys Cys Ser His Cys Thr
            915                 920                 925

Ala Gln Arg Ser Ser Glu Thr Arg Thr Leu Pro Glu Leu Glu Lys Glu
            930                 935                 940

Ala Glu His Ser
945

<210> SEQ ID NO 16
<211> LENGTH: 176
<212> TYPE: PRT
<213> ORGANISM: Rattus norvegicus

<400> SEQUENCE: 16

Gly Gly Leu Arg Leu Ala Ser Glu Gly Val Arg Met Ser Leu Ala Pro
1               5                   10                  15

Asn Gly Glu Ala Ala Thr Ser Pro Met Leu Pro Ala Gly Pro Gly Pro
            20                  25                  30

Glu Ala Pro Val Pro Ala Lys His Gly Ser Ser Gly Arg Pro Arg Asp
        35                  40                  45

Pro Asn Thr Cys Phe Phe Glu Gly Gln Gln Arg Pro His Gly Ala Arg
    50                  55                  60

Trp Ala Pro Asn Tyr Asp Pro Leu Cys Ser Leu Cys Thr Cys Gln Arg
65                  70                  75                  80

Arg Thr Val Ile Cys Asp Pro Val Val Cys Pro Pro Arg Cys Ser
            85                  90                  95

Gln Pro Val Gln Ala Leu Asp Gln Trp Cys Pro Val Cys Ser Glu Lys
            100                 105                 110

Gln Arg Ser Arg Asp Leu Ser Ser Leu Pro Asn Leu Glu Pro Gly Glu
            115                 120                 125

Gly Cys Tyr Phe Asp Gly Asp Arg Ser Trp Arg Ala Ala Gly Thr Arg
        130                 135                 140

Trp His Pro Val Val Pro Pro Phe Gly Leu Ile Lys Cys Gly Val Cys
145                 150                 155                 160

Thr Cys Lys Gly Val Asn Gly Glu Val His Ser Glu Lys Val Gln Cys
            165                 170                 175

<210> SEQ ID NO 17
<211> LENGTH: 801
<212> TYPE: PRT
<213> ORGANISM: Homo sapiens

<400> SEQUENCE: 17

Gln Val Ala Ala Gly His Cys Cys Gln Thr Cys Pro Gln Glu Arg Ser
1               5                   10                  15

```
Ser Ser Glu Arg Gln Pro Ser Gly Leu Ser Phe Glu Tyr Pro Arg Asp
         20                  25                  30

Pro Glu His Arg Ser Tyr Ser Asp Arg Gly Glu Pro Gly Ala Glu Glu
             35                  40                  45

Arg Ala Arg Gly Asp Gly His Thr Asp Phe Val Ala Leu Leu Thr Gly
 50                  55                  60

Pro Arg Ser Gln Ala Val Ala Arg Ala Arg Ala Ser Leu Leu Arg Ser
 65                  70                  75                  80

Ser Leu Arg Phe Ser Ile Ser Tyr Arg Leu Asp Arg Pro Thr Arg
                 85                  90                  95

Ile Arg Phe Ser Asp Pro Asn Gly Ser Val Leu Phe Glu His Pro Ala
                 100                 105                 110

Ala Pro Thr Gln Asp Gly Leu Val Cys Gly Val Trp Arg Ala Val Pro
             115                 120                 125

Arg Leu Ser Leu Arg Leu Leu Arg Ala Glu Gln Leu His Val Ala Leu
 130                 135                 140

Val Thr Leu Thr His Pro Ser Gly Glu Val Trp Gly Pro Leu Ile Arg
145                 150                 155                 160

His Arg Ala Leu Ala Ala Glu Thr Phe Ser Ala Ile Leu Thr Leu Glu
                 165                 170                 175

Gly Pro Pro Gln Gln Gly Val Gly Gly Ile Thr Leu Leu Thr Leu Ser
             180                 185                 190

Asp Thr Glu Asp Ser Leu His Phe Leu Leu Leu Phe Arg Gly Leu Leu
             195                 200                 205

Glu Pro Arg Ser Gly Gly Leu Thr Gln Val Pro Leu Arg Leu Gln Ile
         210                 215                 220

Leu His Gln Gly Gln Leu Leu Arg Glu Leu Gln Ala Asn Val Ser Ala
225                 230                 235                 240

Gln Glu Pro Gly Phe Ala Glu Val Leu Pro Asn Leu Thr Val Gln Glu
                 245                 250                 255

Met Asp Trp Leu Val Leu Gly Glu Leu Gln Met Ala Leu Glu Trp Ala
             260                 265                 270

Gly Arg Pro Gly Leu Arg Ile Ser Gly His Ile Ala Ala Arg Lys Ser
         275                 280                 285

Cys Asp Val Leu Gln Ser Val Leu Cys Gly Ala Asp Ala Leu Ile Pro
290                 295                 300

Val Gln Thr Gly Ala Ala Gly Ser Ala Ser Leu Thr Leu Leu Gly Asn
305                 310                 315                 320

Gly Ser Leu Ile Tyr Gln Ala Val Gly Ile Cys Pro Gly Leu Gly Ala
                 325                 330                 335

Arg Gly Ala His Met Leu Leu Gln Asn Glu Leu Phe Leu Asn Val Gly
             340                 345                 350

Thr Lys Asp Phe Pro Asp Gly Glu Leu Arg Gly His Val Ala Ala Leu
             355                 360                 365

Pro Tyr Cys Gly His Ser Ala Arg His Asp Thr Leu Pro Val Pro Leu
 370                 375                 380

Ala Gly Ala Leu Val Leu Pro Pro Val Lys Ser Gln Ala Ala Gly His
385                 390                 395                 400

Ala Trp Leu Ser Leu Asp Thr His Cys His Leu His Tyr Glu Val Leu
                 405                 410                 415

Leu Ala Gly Leu Gly Gly Ser Glu Gln Gly Thr Val Thr Ala His Leu
             420                 425                 430

Leu Gly Pro Pro Gly Thr Pro Gly Pro Arg Arg Leu Leu Lys Gly Phe
```

```
                    435                 440                 445
Tyr Gly Ser Glu Ala Gln Gly Val Val Lys Asp Leu Glu Pro Glu Leu
                450                 455                 460

Leu Arg His Leu Ala Lys Gly Met Ala Ser Leu Leu Ile Thr Thr Lys
465                 470                 475                 480

Gly Ser Pro Arg Gly Glu Leu Arg Gly Gln Val His Ile Ala Asn Gln
                485                 490                 495

Cys Glu Val Gly Gly Leu Arg Leu Glu Ala Gly Ala Glu Gly Val
                500                 505                 510

Arg Ala Leu Gly Ala Pro Asp Pro Ala Ser Ala Ala Pro Pro Val Val
                515                 520                 525

Pro Gly Leu Pro Ala Leu Ala Pro Ala Lys Pro Gly Gly Pro Gly Arg
530                 535                 540

Pro Arg Asp Pro Asn Thr Cys Phe Phe Glu Gly Gln Gln Arg Pro His
545                 550                 555                 560

Gly Ala Arg Trp Ala Pro Asn Tyr Asp Pro Leu Cys Ser Leu Cys Thr
                565                 570                 575

Cys Gln Arg Arg Thr Val Ile Cys Asp Pro Val Val Cys Pro Pro Pro
                580                 585                 590

Ser Cys Pro His Pro Val Gln Ala Pro Asp Gln Cys Cys Pro Val Cys
                595                 600                 605

Pro Glu Lys Gln Asp Val Arg Asp Leu Pro Gly Leu Pro Arg Ser Arg
610                 615                 620

Asp Pro Gly Glu Gly Cys Tyr Phe Asp Gly Asp Arg Ser Trp Arg Ala
625                 630                 635                 640

Ala Gly Thr Arg Trp His Pro Val Val Pro Pro Phe Gly Leu Ile Lys
                645                 650                 655

Cys Ala Val Cys Thr Cys Lys Gly Gly Thr Gly Glu Val His Cys Glu
                660                 665                 670

Lys Val Gln Cys Pro Arg Leu Ala Cys Ala Gln Pro Val Arg Val Asn
                675                 680                 685

Pro Thr Asp Cys Cys Lys Gln Cys Pro Val Gly Ser Gly Ala His Pro
690                 695                 700

Gln Leu Gly Asp Pro Met Gln Ala Asp Gly Pro Arg Gly Cys Arg Phe
705                 710                 715                 720

Ala Gly Gln Trp Phe Pro Glu Ser Gln Ser Trp His Pro Ser Val Pro
                725                 730                 735

Pro Phe Gly Glu Met Ser Cys Ile Thr Cys Arg Cys Gly Ala Gly Val
                740                 745                 750

Pro His Cys Glu Arg Asp Asp Cys Ser Leu Pro Leu Ser Cys Gly Ser
                755                 760                 765

Gly Lys Glu Ser Arg Cys Cys Ser Arg Cys Thr Ala His Arg Arg Pro
770                 775                 780

Ala Pro Glu Thr Arg Thr Asp Pro Glu Leu Lys Glu Ala Glu Gly
785                 790                 795                 800

Ser

<210> SEQ ID NO 18
<211> LENGTH: 11
<212> TYPE: PRT
<213> ORGANISM: Human immunodeficiency virus type 1

<400> SEQUENCE: 18

Tyr Gly Arg Lys Lys Arg Arg Gln Arg Arg Arg
```

-continued

```
<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence:
      Internalizing domain derived from HIV tat protein

<400> SEQUENCE: 19

Gly Gly Gly Gly Tyr Gly Arg Lys Lys Arg Arg Gln Arg Arg Arg
 1               5                  10                  15

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: PCR primer
      2125-05

<400> SEQUENCE: 20
agtgcccagc tttagtccac                                             20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: PCR primer
      2125-06

<400> SEQUENCE: 21
gagatgagga atatgcacgg                                             20

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: PCR primer
      2127-58

<400> SEQUENCE: 22
gacatctgac tcggctgc                                               18

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: PCR primer
      2212-48

<400> SEQUENCE: 23
tcacgcagta aaccaac                                                17

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: PCR primer
      2235-53

<400> SEQUENCE: 24
```

-continued

```
cggaattcgc caccatggga ggcatgaaat acatcttt                                    38
```

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: PCR primer
      2235-54

<400> SEQUENCE: 25

```
cgcggatcca cagtggccct tttcagatct ctc                                         33
```

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 26

```
ttaccaccag tgaacaataa gg                                                     22
```

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 27

```
cttgagacca cagtatacat tc                                                     22
```

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 28

```
agtgcccagc tttagtccac                                                        20
```

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 29

```
gttctgtttt gcttccttct ag                                                     22
```

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: PCR primer
      2149-76

<400> SEQUENCE: 30

```
gctagcggcc gcgccaccat ggatggcatg aaatacatca tttc                             44
```

<210> SEQ ID NO 31
<211> LENGTH: 33

```
<212> TYPE: DNA
<213> ORGANISM: Artificial Sequence
<220> FEATURE:
<223> OTHER INFORMATION: Description of Artificial Sequence: PCR primer
      2149-77

<400> SEQUENCE: 31
ggtaccggat ccaccaaagg cagggcctcc agc                                   33

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: PCR primer
      2170-06

<400> SEQUENCE: 32
gctagcggcc gcgccaccat gccgagcctc ccggccccg                             39

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: PCR primer
      2170-07

<400> SEQUENCE: 33
ggatccgtcg acggagtgct ccgcttcttt ctccag                                36

<210> SEQ ID NO 34
<211> LENGTH: 345
<212> TYPE: PRT
<213> ORGANISM: Artificial Sequence
<220> FEATURE:
<223> OTHER INFORMATION: Description of Artificial Sequence: Murine
      CHL-FLAG
<220> FEATURE:
<221> NAME/KEY: SIGNAL
<222> LOCATION: (1)..(22)
<220> FEATURE:
<221> NAME/KEY: SITE
<222> LOCATION: (334)..(345)
<223> OTHER INFORMATION: FLAG domain

<400> SEQUENCE: 34

Met Asp Gly Met Lys Tyr Ile Ile Ser Leu Phe Phe Ile Phe Val Phe
  1               5                  10                  15

Leu Glu Gly Ser Lys Thr Glu Gln Val Lys His Ser Asp Thr Tyr Cys
                 20                  25                  30

Val Phe Gln Asp Lys Lys Tyr Arg Val Gly Glu Lys Trp His Pro Tyr
             35                  40                  45

Leu Glu Pro Tyr Gly Leu Val Tyr Cys Val Asn Cys Ile Cys Ser Glu
         50                  55                  60

Asn Gly Asn Val Leu Cys Ser Arg Val Arg Cys Pro Ser Leu His Cys
 65                  70                  75                  80

Leu Ser Pro Val His Ile Pro His Leu Cys Cys Pro Arg Cys Pro Asp
                 85                  90                  95

Ser Leu Pro Pro Val Asn Asn Lys Val Thr Ser Lys Ser Cys Glu Tyr
            100                 105                 110

Asn Gly Thr Thr Tyr Gln His Gly Glu Leu Phe Ile Ala Glu Gly Leu
        115                 120                 125

Phe Gln Asn Arg Gln Pro Asn Gln Cys Ser Gln Cys Ser Cys Ser Glu
```

-continued

```
                130                 135                 140
Gly Asn Val Tyr Cys Gly Leu Lys Thr Cys Pro Lys Leu Thr Cys Ala
145                 150                 155                 160

Phe Pro Val Ser Val Pro Asp Ser Cys Cys Arg Val Cys Arg Gly Asp
                165                 170                 175

Ala Glu Leu Ser Trp Glu His Ala Asp Gly Asp Ile Phe Arg Gln Pro
                180                 185                 190

Ala Asn Arg Glu Ala Arg His Ser Tyr Leu Arg Ser Pro Tyr Asp Pro
                195                 200                 205

Pro Pro Asn Arg Gln Ala Gly Gly Leu Pro Arg Phe Pro Gly Ser Arg
210                 215                 220

Ser His Arg Gly Ala Val Ile Asp Ser Gln Gln Ala Ser Gly Thr Ile
225                 230                 235                 240

Val Gln Ile Val Ile Asn Asn Lys His Lys His Gly Gln Val Cys Val
                245                 250                 255

Ser Asn Gly Lys Thr Tyr Ser His Gly Glu Ser Trp His Pro Asn Leu
                260                 265                 270

Arg Ala Phe Gly Ile Val Glu Cys Val Leu Cys Thr Cys Asn Val Thr
                275                 280                 285

Lys Gln Glu Cys Lys Lys Ile His Cys Pro Asn Arg Tyr Pro Cys Lys
290                 295                 300

Tyr Pro Gln Lys Ile Asp Gly Lys Cys Cys Lys Val Cys Pro Gly Lys
305                 310                 315                 320

Lys Ala Lys Gly Ala Leu Ala Gly Gly Pro Ala Phe Gly Gly Ser Gly
                325                 330                 335

Thr Asp Tyr Lys Asp Asp Asp Lys
                340                 345
```

<210> SEQ ID NO 35
<211> LENGTH: 323
<212> TYPE: PRT
<213> ORGANISM: Artificial Sequence
<220> FEATURE:
<223> OTHER INFORMATION: Description of Artificial Sequence: Murine
      CHL-FLAG
<220> FEATURE:
<221> NAME/KEY: SITE
<222> LOCATION: (312)..(323)
<223> OTHER INFORMATION: FLAG domain

<400> SEQUENCE: 35

```
Glu Gln Val Lys His Ser Asp Thr Tyr Cys Val Phe Gln Asp Lys Lys
  1               5                  10                  15

Tyr Arg Val Gly Glu Lys Trp His Pro Tyr Leu Glu Pro Tyr Gly Leu
                 20                  25                  30

Val Tyr Cys Val Asn Cys Ile Cys Ser Glu Asn Gly Asn Val Leu Cys
             35                  40                  45

Ser Arg Val Arg Cys Pro Ser Leu His Cys Leu Ser Pro Val His Ile
         50                  55                  60

Pro His Leu Cys Cys Pro Arg Cys Pro Asp Ser Leu Pro Pro Val Asn
 65                  70                  75                  80

Asn Lys Val Thr Ser Lys Ser Cys Glu Tyr Asn Gly Thr Thr Tyr Gln
                 85                  90                  95

His Gly Glu Leu Phe Ile Ala Glu Gly Leu Phe Gln Asn Arg Gln Pro
             100                 105                 110

Asn Gln Cys Ser Gln Cys Ser Cys Ser Glu Gly Asn Val Tyr Cys Gly
         115                 120                 125
```

```
Leu Lys Thr Cys Pro Lys Leu Thr Cys Ala Phe Pro Val Ser Val Pro
    130                 135                 140

Asp Ser Cys Cys Arg Val Cys Arg Gly Asp Ala Glu Leu Ser Trp Glu
145                 150                 155                 160

His Ala Asp Gly Asp Ile Phe Arg Gln Pro Ala Asn Arg Glu Ala Arg
                165                 170                 175

His Ser Tyr Leu Arg Ser Pro Tyr Asp Pro Pro Asn Arg Gln Ala
            180                 185                 190

Gly Gly Leu Pro Arg Phe Pro Gly Ser Arg Ser His Arg Gly Ala Val
                195                 200                 205

Ile Asp Ser Gln Gln Ala Ser Gly Thr Ile Val Gln Ile Val Ile Asn
    210                 215                 220

Asn Lys His Lys His Gly Gln Val Cys Val Ser Asn Gly Lys Thr Tyr
225                 230                 235                 240

Ser His Gly Glu Ser Trp His Pro Asn Leu Arg Ala Phe Gly Ile Val
                245                 250                 255

Glu Cys Val Leu Cys Thr Cys Asn Val Thr Lys Gln Glu Cys Lys Lys
                260                 265                 270

Ile His Cys Pro Asn Arg Tyr Pro Cys Lys Tyr Pro Gln Lys Ile Asp
            275                 280                 285

Gly Lys Cys Cys Lys Val Cys Pro Gly Lys Lys Ala Lys Gly Ala Leu
            290                 295                 300

Ala Gly Gly Pro Ala Phe Gly Gly Ser Gly Thr Asp Tyr Lys Asp Asp
305                 310                 315                 320

Asp Asp Lys

<210> SEQ ID NO 36
<211> LENGTH: 962
<212> TYPE: PRT
<213> ORGANISM: Artificial Sequence
<220> FEATURE:
<223> OTHER INFORMATION: Description of Artificial Sequence: Murine
      CHD-FLAG
<220> FEATURE:
<221> NAME/KEY: SIGNAL
<222> LOCATION: (1)..(26)
<220> FEATURE:
<221> NAME/KEY: SITE
<222> LOCATION: (951)..(962)
<223> OTHER INFORMATION: FLAG domain

<400> SEQUENCE: 36

Met Pro Ser Leu Pro Ala Pro Pro Ala Pro Arg Leu Leu Leu Gly Leu
1               5                   10                  15

Leu Leu Leu Gly Ser Arg Pro Ala Ser Gly Thr Gly Pro Glu Pro Pro
                20                  25                  30

Ala Leu Pro Ile Arg Ser Glu Lys Glu Pro Leu Pro Val Arg Gly Ala
            35                  40                  45

Ala Gly Cys Ser Phe Gly Gly Lys Val Tyr Ala Leu Asp Glu Thr Trp
        50                  55                  60

His Pro Asp Leu Gly Glu Pro Phe Gly Val Met Arg Cys Val Leu Cys
65                  70                  75                  80

Ala Cys Glu Ala Pro Gln Trp Ala Arg Arg Gly Arg Gly Pro Gly Arg
                85                  90                  95

Val Ser Cys Lys Asn Ile Lys Pro Gln Cys Pro Thr Leu Ala Cys Arg
            100                 105                 110

Gln Pro Arg Gln Leu Pro Gly His Cys Cys Gln Thr Cys Pro Gln Glu
```

```
            115                 120                 125
Arg Ser Asn Leu Asp Pro Gln Pro Ala Gly Leu Val Phe Glu Tyr Pro
    130                 135                 140

Arg Asp Pro Glu His Arg Ser Tyr Ser Asp Arg Gly Glu Pro Gly Val
145                 150                 155                 160

Gly Glu Arg Thr Arg Ala Asp Gly His Thr Asp Phe Val Ala Leu Leu
                165                 170                 175

Thr Gly Pro Arg Ser Gln Ala Val Ala Arg Ala Arg Val Ser Leu Leu
            180                 185                 190

Arg Ser Ser Leu Arg Phe Ser Val Ser Tyr Gln Arg Leu Asp Arg Pro
        195                 200                 205

Ser Arg Val Arg Phe Thr Asp Pro Thr Gly Asn Ile Leu Phe Glu His
    210                 215                 220

Pro Ala Thr Pro Thr Gln Asp Gly Leu Val Cys Gly Val Trp Arg Ala
225                 230                 235                 240

Val Pro Arg Leu Ser Val Arg Leu Leu Arg Ala Glu Gln Leu Arg Val
                245                 250                 255

Ala Leu Val Thr Ser Thr His Pro Ser Gly Glu Val Trp Gly Pro Leu
            260                 265                 270

Ile Trp Gln Gly Ala Leu Ala Ala Glu Thr Phe Ser Ala Ile Leu Thr
        275                 280                 285

Leu Glu Asp Pro Leu Gln Arg Gly Val Gly Gly Ile Ala Leu Leu Thr
    290                 295                 300

Leu Ser Asp Thr Glu Asp Ser Leu His Phe Leu Leu Phe Arg Gly
305                 310                 315                 320

Leu Leu Gly Gly Leu Ala Gln Ala Pro Leu Lys Leu Gln Ile Leu His
                325                 330                 335

Gln Gly Gln Leu Leu Arg Glu Leu Gln Ala Asn Thr Ser Ala Gln Glu
            340                 345                 350

Pro Gly Phe Ala Glu Val Leu Pro Ser Leu Thr Asp Gln Glu Met Asp
        355                 360                 365

Trp Leu Glu Leu Gly Glu Leu Gln Met Val Leu Glu Lys Ala Gly Gly
    370                 375                 380

Pro Glu Leu Arg Ile Ser Gly Tyr Ile Thr Thr Arg Gln Ser Cys Asp
385                 390                 395                 400

Val Leu Gln Ser Val Leu Cys Gly Ala Asp Ala Leu Ile Pro Val Gln
                405                 410                 415

Thr Gly Ala Ala Gly Ser Ala Ser Phe Ile Leu Leu Gly Asn Gly Ser
            420                 425                 430

Leu Ile Tyr Gln Val Gln Val Val Gly Thr Gly Ser Glu Val Val Ala
        435                 440                 445

Met Thr Leu Glu Thr Lys Pro Gln Arg Lys Asn Gln Arg Thr Val Leu
    450                 455                 460

Cys His Met Ala Gly Leu Gln Pro Gly Gly His Met Ala Val Gly Met
465                 470                 475                 480

Cys Ser Gly Leu Gly Ala Arg Gly Ala His Met Leu Leu Gln Asn Glu
                485                 490                 495

Leu Phe Leu Asn Val Gly Thr Lys Asp Phe Pro Asp Gly Glu Leu Arg
            500                 505                 510

Gly His Val Thr Ala Leu Cys Tyr Ser Gly His Ser Ala Arg Tyr Asp
        515                 520                 525

Arg Leu Pro Val Pro Leu Ala Gly Ala Leu Val Leu Pro Pro Val Arg
    530                 535                 540
```

```
Ser Gln Ala Ala Gly His Ala Trp Leu Ser Leu Asp Thr His Cys His
545                 550                 555                 560

Leu His Tyr Glu Val Leu Leu Ala Gly Leu Gly Gly Ser Glu Gln Gly
                565                 570                 575

Thr Val Thr Ala His Leu Leu Gly Pro Pro Gly Met Pro Gly Pro Gln
                580                 585                 590

Arg Leu Leu Lys Gly Phe Tyr Gly Ser Glu Ala Gln Gly Val Val Lys
                595                 600                 605

Asp Leu Glu Pro Val Leu Leu Arg His Leu Ala Gln Gly Thr Ala Ser
                610                 615                 620

Leu Leu Ile Thr Thr Lys Ser Ser Pro Arg Gly Glu Leu Arg Gly Gln
625                 630                 635                 640

Val His Ile Ala Ser Gln Cys Glu Ala Gly Gly Leu Arg Leu Ala Ser
                645                 650                 655

Glu Gly Val Gln Met Pro Leu Ala Pro Asn Gly Glu Ala Ala Thr Ser
                660                 665                 670

Pro Met Leu Pro Ala Gly Pro Gly Pro Glu Ala Pro Val Pro Ala Lys
                675                 680                 685

His Gly Ser Pro Gly Arg Pro Arg Asp Pro Asn Thr Cys Phe Phe Glu
                690                 695                 700

Gly Gln Gln Arg Pro His Gly Ala Arg Trp Ala Pro Asn Tyr Asp Pro
705                 710                 715                 720

Leu Cys Ser Leu Cys Ile Cys Gln Arg Arg Thr Val Ile Cys Asp Pro
                725                 730                 735

Val Val Cys Pro Pro Pro Ser Cys Pro His Pro Val Gln Ala Leu Asp
                740                 745                 750

Gln Cys Cys Pro Val Cys Pro Glu Lys Gln Arg Ser Arg Asp Leu Pro
                755                 760                 765

Ser Leu Pro Asn Leu Glu Pro Gly Glu Gly Cys Tyr Phe Asp Gly Asp
                770                 775                 780

Arg Ser Trp Arg Ala Ala Gly Thr Arg Trp His Pro Val Val Pro Pro
785                 790                 795                 800

Phe Gly Leu Ile Lys Cys Ala Val Cys Thr Cys Lys Gly Ala Thr Gly
                805                 810                 815

Glu Val His Cys Glu Lys Val Gln Cys Pro Arg Leu Ala Cys Ala Gln
                820                 825                 830

Pro Val Arg Ala Asn Pro Thr Asp Cys Cys Lys Gln Cys Pro Val Gly
                835                 840                 845

Ser Gly Thr Asn Ala Lys Leu Gly Asp Pro Met Gln Ala Asp Gly Pro
850                 855                 860

Arg Gly Cys Arg Phe Ala Gly Gln Trp Phe Pro Glu Asn Gln Ser Trp
865                 870                 875                 880

His Pro Ser Val Pro Pro Phe Gly Glu Met Ser Cys Ile Thr Cys Arg
                885                 890                 895

Cys Gly Ala Gly Val Pro His Cys Glu Arg Asp Asp Cys Ser Pro Pro
                900                 905                 910

Leu Ser Cys Gly Ser Gly Lys Glu Ser Arg Cys Cys Ser His Cys Thr
                915                 920                 925

Ala Gln Arg Ser Ser Glu Thr Arg Thr Leu Pro Glu Leu Glu Lys Glu
                930                 935                 940

Ala Glu His Ser Val Asp Gly Ser Gly Thr Asp Tyr Lys Asp Asp Asp
945                 950                 955                 960
```

Asp Lys

<210> SEQ ID NO 37
<211> LENGTH: 936
<212> TYPE: PRT
<213> ORGANISM: Artificial Sequence
<220> FEATURE:
<223> OTHER INFORMATION: Description of Artificial Sequence: Murine
      CHD-FLAG
<220> FEATURE:
<221> NAME/KEY: SITE
<222> LOCATION: (925)..(936)
<223> OTHER INFORMATION: FLAG domain

<400> SEQUENCE: 37

```
Thr Gly Pro Glu Pro Ala Leu Pro Ile Arg Ser Glu Lys Glu Pro
  1               5                  10                  15

Leu Pro Val Arg Gly Ala Ala Gly Cys Ser Phe Gly Gly Lys Val Tyr
                 20                  25                  30

Ala Leu Asp Glu Thr Trp His Pro Asp Leu Gly Glu Pro Phe Gly Val
             35                  40                  45

Met Arg Cys Val Leu Cys Ala Cys Glu Ala Pro Gln Trp Ala Arg Arg
     50                  55                  60

Gly Arg Gly Pro Gly Arg Val Ser Cys Lys Asn Ile Lys Pro Gln Cys
 65                  70                  75                  80

Pro Thr Leu Ala Cys Arg Gln Pro Arg Gln Leu Pro Gly His Cys Cys
                 85                  90                  95

Gln Thr Cys Pro Gln Glu Arg Ser Asn Leu Asp Pro Gln Pro Ala Gly
                100                 105                 110

Leu Val Phe Glu Tyr Pro Arg Asp Pro Glu His Arg Ser Tyr Ser Asp
            115                 120                 125

Arg Gly Glu Pro Gly Val Gly Glu Arg Thr Arg Ala Asp Gly His Thr
130                 135                 140

Asp Phe Val Ala Leu Leu Thr Gly Pro Arg Ser Gln Ala Val Ala Arg
145                 150                 155                 160

Ala Arg Val Ser Leu Leu Arg Ser Ser Leu Arg Phe Ser Val Ser Tyr
                165                 170                 175

Gln Arg Leu Asp Arg Pro Ser Arg Val Arg Phe Thr Asp Pro Thr Gly
            180                 185                 190

Asn Ile Leu Phe Glu His Pro Ala Thr Pro Thr Gln Asp Gly Leu Val
        195                 200                 205

Cys Gly Val Trp Arg Ala Val Pro Arg Leu Ser Val Arg Leu Leu Arg
    210                 215                 220

Ala Glu Gln Leu Arg Val Ala Leu Val Thr Ser Thr His Pro Ser Gly
225                 230                 235                 240

Glu Val Trp Gly Pro Leu Ile Trp Gln Gly Ala Leu Ala Ala Glu Thr
                245                 250                 255

Phe Ser Ala Ile Leu Thr Leu Glu Asp Pro Leu Gln Arg Gly Val Gly
            260                 265                 270

Gly Ile Ala Leu Leu Thr Leu Ser Asp Thr Glu Asp Ser Leu His Phe
        275                 280                 285

Leu Leu Leu Phe Arg Gly Leu Leu Gly Gly Leu Ala Gln Ala Pro Leu
    290                 295                 300

Lys Leu Gln Ile Leu His Gln Gly Gln Leu Leu Arg Glu Leu Gln Ala
305                 310                 315                 320

Asn Thr Ser Ala Gln Glu Pro Gly Phe Ala Glu Val Leu Pro Ser Leu
                325                 330                 335
```

```
Thr Asp Gln Glu Met Asp Trp Leu Glu Leu Gly Glu Leu Gln Met Val
            340                 345                 350
Leu Glu Lys Ala Gly Gly Pro Glu Leu Arg Ile Ser Gly Tyr Ile Thr
            355                 360                 365
Thr Arg Gln Ser Cys Asp Val Leu Gln Ser Val Leu Cys Gly Ala Asp
            370                 375                 380
Ala Leu Ile Pro Val Gln Thr Gly Ala Ala Gly Ser Ala Ser Phe Ile
385                 390                 395                 400
Leu Leu Gly Asn Gly Ser Leu Ile Tyr Gln Val Gln Val Val Gly Thr
            405                 410                 415
Gly Ser Glu Val Val Ala Met Thr Leu Glu Thr Lys Pro Gln Arg Lys
            420                 425                 430
Asn Gln Arg Thr Val Leu Cys His Met Ala Gly Leu Gln Pro Gly Gly
            435                 440                 445
His Met Ala Val Gly Met Cys Ser Gly Leu Gly Ala Arg Gly Ala His
            450                 455                 460
Met Leu Leu Gln Asn Glu Leu Phe Leu Asn Val Gly Thr Lys Asp Phe
465                 470                 475                 480
Pro Asp Gly Glu Leu Arg Gly His Val Thr Ala Leu Cys Tyr Ser Gly
            485                 490                 495
His Ser Ala Arg Tyr Asp Arg Leu Pro Val Pro Leu Ala Gly Ala Leu
            500                 505                 510
Val Leu Pro Pro Val Arg Ser Gln Ala Ala Gly His Ala Trp Leu Ser
            515                 520                 525
Leu Asp Thr His Cys His Leu His Tyr Glu Val Leu Leu Ala Gly Leu
            530                 535                 540
Gly Gly Ser Glu Gln Gly Thr Val Thr Ala His Leu Leu Gly Pro Pro
545                 550                 555                 560
Gly Met Pro Gly Pro Gln Arg Leu Leu Lys Gly Phe Tyr Gly Ser Glu
            565                 570                 575
Ala Gln Gly Val Val Lys Asp Leu Glu Pro Val Leu Leu Arg His Leu
            580                 585                 590
Ala Gln Gly Thr Ala Ser Leu Leu Ile Thr Thr Lys Ser Ser Pro Arg
            595                 600                 605
Gly Glu Leu Arg Gly Gln Val His Ile Ala Ser Gln Cys Glu Ala Gly
            610                 615                 620
Gly Leu Arg Leu Ala Ser Glu Gly Val Gln Met Pro Leu Ala Pro Asn
625                 630                 635                 640
Gly Glu Ala Ala Thr Ser Pro Met Leu Pro Ala Gly Pro Gly Pro Glu
            645                 650                 655
Ala Pro Val Pro Ala Lys His Gly Ser Pro Gly Arg Pro Arg Asp Pro
            660                 665                 670
Asn Thr Cys Phe Phe Glu Gly Gln Gln Arg Pro His Gly Ala Arg Trp
            675                 680                 685
Ala Pro Asn Tyr Asp Pro Leu Cys Ser Leu Cys Ile Cys Gln Arg Arg
            690                 695                 700
Thr Val Ile Cys Asp Pro Val Val Cys Pro Pro Ser Cys Pro His His
705                 710                 715                 720
Pro Val Gln Ala Leu Asp Gln Cys Cys Pro Val Cys Pro Glu Lys Gln
            725                 730                 735
Arg Ser Arg Asp Leu Pro Ser Leu Pro Asn Leu Glu Pro Gly Glu Gly
            740                 745                 750
```

```
Cys Tyr Phe Asp Gly Asp Arg Ser Trp Arg Ala Ala Gly Thr Arg Trp
        755                 760                 765

His Pro Val Val Pro Pro Phe Gly Leu Ile Lys Cys Ala Val Cys Thr
    770                 775                 780

Cys Lys Gly Ala Thr Gly Glu Val His Cys Glu Lys Val Gln Cys Pro
785                 790                 795                 800

Arg Leu Ala Cys Ala Gln Pro Val Arg Ala Asn Pro Thr Asp Cys Cys
                805                 810                 815

Lys Gln Cys Pro Val Gly Ser Gly Thr Asn Ala Lys Leu Gly Asp Pro
                820                 825                 830

Met Gln Ala Asp Gly Pro Arg Gly Cys Arg Phe Ala Gly Gln Trp Phe
        835                 840                 845

Pro Glu Asn Gln Ser Trp His Pro Ser Val Pro Pro Phe Gly Glu Met
    850                 855                 860

Ser Cys Ile Thr Cys Arg Cys Gly Ala Gly Val Pro His Cys Glu Arg
865                 870                 875                 880

Asp Asp Cys Ser Pro Pro Leu Ser Cys Gly Ser Gly Lys Glu Ser Arg
                885                 890                 895

Cys Cys Ser His Cys Thr Ala Gln Arg Ser Ser Glu Thr Arg Thr Leu
            900                 905                 910

Pro Glu Leu Glu Lys Glu Ala Glu His Ser Val Asp Gly Ser Gly Thr
        915                 920                 925

Asp Tyr Lys Asp Asp Asp Lys
930                 935
```

CHORDIN-LIKE MOLECULES AND USES THEREOF

CROSS-REFERENCE TO RELATED APPLICATIONS

This application is a divisional of U.S. patent application Ser. No. 09/724,915, filed Nov. 28, 2000, now allowed, which claims the benefit under 35 U.S.C. 119(e) of U.S. Provisional Application Ser. No. 60/169,494, filed Dec. 7, 1999, all of which are incorporated in their entirety by reference herein.

FIELD OF THE INVENTION

The present invention relates to Chordin-Like (CHL) polypeptides and nucleic acid molecules encoding the same. The invention also relates to selective binding agents, vectors, host cells, and methods for producing CHL polypeptides. The invention further relates to pharmaceutical compositions and methods for the diagnosis, treatment, amelioration, and/or prevention of diseases, disorders, and conditions associated with CHL polypeptides.

BACKGROUND OF THE INVENTION

Technical advances in the identification, cloning, expression, and manipulation of nucleic acid molecules and the deciphering of the human genome have greatly accelerated the discovery of novel therapeutics. Rapid nucleic acid sequencing techniques can now generate sequence information at unprecedented rates and, coupled with computational analyses, allow the assembly of overlapping sequences into partial and entire genomes and the identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides may confer advantageous properties on a product for use as a therapeutic.

In spite of the significant technical advances in genome research over the past decade, the potential for the development of novel therapeutics based on the human genome is still largely unrealized. Many genes encoding potentially beneficial polypeptide therapeutics or those encoding polypeptides, which may act as "targets" for therapeutic molecules, have still not been identified. Accordingly, it is an object of the invention to identify novel polypeptides, and nucleic acid molecules encoding the same, which have diagnostic or therapeutic benefit.

Bone morphogenetic protein (BMP) is a member of the transforming growth factor-beta family, which was originally identified as a factor promoting bone formation from a cartridge implant (Wozney et al, 1988, *Science* 242:1528-34; Celeste et al., 1990, *Proc. Nat. Acad. Sci. USA* 87:9843-47). BMP is also known to play an essential role during the early embryogenesis of the frog, the fly, and in mammals. The precise concentration of active BMP seems to be important for the specification of particular cell types (Dale et al., 1992, *Development* 115:573-85; Dosch et al., 1997, *Development* 124:2325-34). An activity gradient of BMP2/4 is observed in, for example, *Xenopus* embryos in which the lowest expression is detected at the dorsal tip and the highest expression at the ventral tip—establishing the dorsoventral axis determination in the embryo. In another example, the control of BMP concentration at specific sites of tissue development suggests a role for BMP in organogenesis. Control of BMP expression is achieved by either localized expression of the BMP gene products or through the influence of the BMP inhibitor chordin (CHD) (Sasai et al., 1994, *Cell* 79:779-90)—or short gastrulation (SOG) (Francois et al., 1994, *Genes Dev.* 8:2602-16).

CHD/SOG is a large secreted protein produced from the Spemann's organizer, the master-controlling region for the dorsoventral axis specification at the gastrulation stage of *Xenopus* embryogenesis. CHD/SOG functions as a dorsalization factor, as does Noggin (Smith and Harland, 1992, *Cell* 70:82940), which is also secreted from the organizer. The *Drosophila* SOG has a transmembrane domain at its amino-terminus, suggesting that it may be a type II transmembrane protein (Francois et al., 1994, *Genes Dev.* 8:2602-16). It has been proposed that the carboxyl-terminal side (extracellular domain) of the *Drosophila* SOG is cleaved off. However, *Xenopus* CHD (Sasai et al., 1994, *Cell* 79:779-90), Zebrafish CHD (Schulte-Merker et al., 1997, *Nature* 387:862-63), and murine CHD (Pappano et al., 1998, *Genomics* 52:236-39) do not contain the transmembrane domain. Instead, these proteins have a signal peptide, and are secreted directly. The CHD/SOG polypeptide contains four repeats of the cysteine-rich domain (CR1-4) that is also found in a variety of extracellular matrix proteins such as collagen and thrombospondin.

CHD/SOG is known to bind to one of the ventralizing factors, BMP4 (Piccolo et al., 1996, *Cell* 86:589-98). BMP4 has been shown to be essential for embryonic development of posterior-ventral mesoderm in mice (Winnier et al., 1995, *Genes Dev.* 9:2105-16). The binding of CHD/SOG to BMP4 inhibits BMP4 activity by preventing BMP4 from binding to its receptor (Piccolo et al., 1996, *Cell* 86:589-98). In this respect, the functional relationship between CHD/SOG and BMP4 resembles that between OPG and OPGL, although CHD/SOG is not structurally related to the BMP receptors. The binding affinity of CHD/SOG to BMP4 is specific and tight (Kd=$3 \times 10^{-10}$ M (Piccolo et al., 1996, *Cell* 86:589-98), and seems to require proteolysis in order to effectuate the release of bound BMP4. This proteolysis is achieved by a specific metalloprotease—Tolloid (TLD) or BMP 1—that cleaves CHD/SOG to liberate either, or both, the first (CR1) and last (CR4) CR motifs (Piccolo et al., 1997, *Cell* 91: 407-16). Whether or not CHD/SOG has other functions or an independent function through its own receptor remains to be determined.

One of the most important roles of CHD/SOG is to establish a BMP4 morphogen gradient (Jones and Smith, 1998, *Dev. Biol.* 194:12-17). BMP4 itself only migrates a short distance and seems to act essentially on the cell autonomously (Jones et al., 1996, *Curr. Biol.* 6:1468-75). In contrast, the BMP4 inhibitors Noggin and CHD/SOG appear to exert a long-range effect, thereby forming an activity gradient of BMP4.

BMPs also play important roles outside of early embryogenesis, for example in the organogenesis of lung, gut, kidney, skin, heart and teeth, as well as in the later stages of embryogenesis (Hogan, 1996, *Genes Dev.* 10:1580-94). Some BMPs are expressed in a very localized fashion while others are expressed widely in a tissue. The importance of the localized action of BMP for organogenesis has been supported by transgenic mouse experiments using constructs by which BMP concentration is artificially elevated throughout the target tissue. In the case of lung, BMP4 is expressed in the distal tips of epithelium in the developing lung, and when overexpressed with the surfactant protein C promoter, the development of a small lung in which the structural organization (i.e., branching) has been severely disrupted is observed (Bellusci et al., 1996, *Development* 122:1693-702). Since the putative BMP-activity gradient could also be disrupted by the transgene expression, BMPs expressed widely in the tissue could also play a role in the determination of the structural organization of a tissue.

Noggin is another BMP2/4 inhibitor secreted from Spemann's organizer (Zimmerman et al., 1996, *Cell* 86:599-606). The biological role of Noggin and its mode of action are similar to CHD/SOG in *Xenopus*. Although the most notable function of Noggin is, like CHD/SOG, dorsalization, Noggin null-mutant mice have shown a bone phenotype (hyperplasia of chondrocytes) instead of an early embryonic phenotype (McMahon et al., 1998, *Genes Dev.* 12:1438-52; Brunet et al., 1998, *Science* 280:1455-57). This suggests that CHL or even CHD might have a non-dispensable function in the later stage of embryogenesis.

SUMMARY OF THE INVENTION

The present invention relates to novel CHL nucleic acid molecules and encoded polypeptides.

The invention provides for an isolated nucleic acid molecule comprising a nucleotide sequence selected from the group consisting of:

(a) the nucleotide sequence as set forth in any of SEQ ID NO: 1, SEQ ID NO: 4, SEQ ID NO: 7, or SEQ ID NO: 11;

(b) the nucleotide sequence of the DNA insert in any of ATCC Deposit Nos. PTA-961, PTA-962, PTA-963, or PTA-964;

(c) a nucleotide sequence encoding the polypeptide as set forth in any of SEQ ID NO: 2, SEQ ID NO: 5, SEQ ID NO: 8, or SEQ ID NO: 12;

(d) a nucleotide sequence which hybridizes under moderately or highly stringent conditions to the complement of any of (a)-(c); and (e) a nucleotide sequence complementary to any of (a)-(c).

The invention also provides for an isolated nucleic acid molecule comprising a nucleotide sequence selected from the group consisting of:

(a) a nucleotide sequence encoding a polypeptide which is at least about 70 percent identical to the polypeptide as set forth in any of SEQ ID NO: 2, SEQ ID NO: 5, SEQ ID NO: 8, or SEQ ID NO: 12, wherein the encoded polypeptide has an activity of the polypeptide set forth in any of SEQ ID NO: 2, SEQ ID NO: 5, SEQ ID NO: 8, or SEQ ID NO: 12;

(b) a nucleotide sequence encoding an allelic variant or splice variant of the nucleotide sequence as set forth in any of SEQ ID NO: 1, SEQ ID NO: 4, SEQ ID NO: 7, or SEQ ID NO: 11, the nucleotide sequence of the DNA insert in any of ATCC Deposit Nos. PTA-961, PTA-962, PTA-963, or PTA-964, or (a);

(c) a region of the nucleotide sequence of any of SEQ ID NO: 1, SEQ ID NO: 4, SEQ ID NO: 7, or SEQ ID NO: 11, the DNA insert in any of ATCC Deposit Nos. PTA-961, PTA-962, PTA-963, or PTA-964, (a), or (b) encoding a polypeptide fragment of at least about 25 amino acid residues, wherein the polypeptide fragment has an activity of the polypeptide set forth in any of SEQ ID NO: 2, SEQ ID NO: 5, SEQ ID NO: 8, or SEQ ID NO: 12, or is antigenic;

(d) a region of the nucleotide sequence of any of SEQ ID NO: 1, SEQ ID NO: 4, SEQ ID NO: 7, or SEQ ID NO: 11, the DNA insert in any of ATCC Deposit Nos. PTA-961, PTA-962, PTA-963, or PTA-964, or any of (a)-(c) comprising a fragment of at least about 16 nucleotides;

(e) a nucleotide sequence which hybridizes under moderately or highly stringent conditions to the complement of any of (a)-(d); and (f) a nucleotide sequence complementary to any of (a)-(d).

The invention further provides for an isolated nucleic acid molecule comprising a nucleotide sequence selected from the group consisting of:

(a) a nucleotide sequence encoding a polypeptide as set forth in any of SEQ ID NO: 2, SEQ ID NO: 5, SEQ ID NO: 8, or SEQ ID NO: 12 with at least one conservative amino acid substitution, wherein the encoded polypeptide has an activity of the polypeptide set forth in any of SEQ ID NO: 2, SEQ ID NO: 5, SEQ ID NO: 8, or SEQ ID NO: 12;

(b) a nucleotide sequence encoding a polypeptide as set forth in any of SEQ ID NO: 2, SEQ ID NO: 5, SEQ ID NO: 8, or SEQ ID NO: 12 with at least one amino acid insertion, wherein the encoded polypeptide has an activity of the polypeptide set forth in any of SEQ ID NO: 2, SEQ ID NO: 5, SEQ ID NO: 8, or SEQ ID NO: 12;

(c) a nucleotide sequence encoding a polypeptide as set forth in any of SEQ ID NO: 2, SEQ ID NO: 5, SEQ ID NO: 8, or SEQ ID NO: 12 with at least one amino acid deletion, wherein the encoded polypeptide has an activity of the polypeptide set forth in any of SEQ ID NO: 2, SEQ ID NO: 5, SEQ ID NO: 8, or SEQ ID NO: 12;

(d) a nucleotide sequence encoding a polypeptide as set forth in any of SEQ ID NO: 2, SEQ ID NO: 5, SEQ ID NO: 8, or SEQ ID NO: 12 which has a C- and/or N-terminal truncation, wherein the encoded polypeptide has an activity of the polypeptide set forth in any of SEQ ID NO: 2, SEQ ID NO: 5, SEQ ID NO: 8, or SEQ ID NO: 12;

(e) a nucleotide sequence encoding a polypeptide as set forth in any of SEQ ID NO: 2, SEQ ID NO: 5, SEQ ID NO: 8, or SEQ ID NO: 12 with at least one modification selected from the group consisting of amino acid substitutions, amino acid insertions, amino acid deletions, C-terminal truncation, and N-terminal truncation, wherein the encoded polypeptide has an activity of the polypeptide set forth in any of SEQ ID NO: 2, SEQ ID NO: 5, SEQ ID NO: 8, or SEQ ID NO: 12;

(f) a nucleotide sequence of any of (a)-(e) comprising a fragment of at least about 16 nucleotides;

(g) a nucleotide sequence which hybridizes under moderately or highly stringent conditions to the complement of any of (a)-(f); and (h) a nucleotide sequence complementary to any of (a)-(e).

The present invention provides for an isolated polypeptide comprising an amino acid sequence selected from the group consisting of:

(a) the amino acid sequence as set forth in any of SEQ ID NO: 2, SEQ ID NO: 5, SEQ ID NO: 8, or SEQ ID NO: 12; and (b) the amino acid sequence encoded by the DNA insert in any of ATCC Deposit Nos. PTA-961, PTA-962, PTA-963, or PTA-964.

The invention also provides for an isolated polypeptide comprising the amino acid sequence selected from the group consisting of:

(a) the amino acid sequence as set forth in any of SEQ ID NO: 3, SEQ ID NO: 6, SEQ ID NO: 9, SEQ ID NO: 10, SEQ ID NO: 13, or SEQ ID NO: 14 optionally further comprising an amino-terminal methionine;

(b) an amino acid sequence for an ortholog of any of SEQ ID NO: 2, SEQ ID NO: 5, SEQ ID NO: 8, or SEQ ID NO: 12;

(c) an amino acid sequence which is at least about 70 percent identical to the amino acid sequence of any of SEQ ID NO: 2, SEQ ID NO: 5, SEQ ID NO: 8, or SEQ ID NO: 12, wherein the polypeptide has an activity of the polypeptide set forth in any of SEQ ID NO: 2, SEQ ID NO: 5, SEQ ID NO: 8, or SEQ ID NO: 12;

(d) a fragment of the amino acid sequence set forth in any of SEQ ID NO: 2, SEQ ID NO: 5, SEQ ID NO: 8, or SEQ ID NO: 12 comprising at least about 25 amino acid residues, wherein the fragment has an activity of the polypeptide set forth in any of SEQ ID NO: 2, SEQ ID NO: 5, SEQ ID NO: 8, or SEQ ID NO: 12, or is antigenic; and (e) an amino acid sequence for an allelic variant or splice variant of the amino acid sequence as set forth in any of SEQ ID NO: 2, SEQ ID NO: 5, SEQ ID NO: 8, or SEQ ID NO: 12, the amino acid sequence encoded by the DNA insert in any of ATCC Deposit Nos. PTA-961, PTA-962, PTA-963, or PTA-964, or any of (a)-(c).

The invention further provides for an isolated polypeptide comprising the amino acid sequence selected from the group consisting of:

(a) the amino acid sequence as set forth in any of SEQ ID NO: 2, SEQ ID NO: 5, SEQ ID NO: 8, or SEQ ID NO: 12 with at least one conservative amino acid substitution, wherein the polypeptide has an activity of the polypeptide set forth in any of SEQ ID NO: 2, SEQ ID NO: 5, SEQ ID NO: 8, or SEQ ID NO: 12;

(b) the amino acid sequence as set forth in any of SEQ ID NO: 2, SEQ ID NO: 5, SEQ ID NO: 8, or SEQ ID NO: 12 with at least one amino acid insertion, wherein the polypeptide has an activity of the polypeptide set forth in any of SEQ ID NO: 2, SEQ ID NO: 5, SEQ ID NO: 8, or SEQ ID NO: 12;

(c) the amino acid sequence as set forth in any of SEQ ID NO: 2, SEQ ID NO: 5, SEQ ID NO: 8, or SEQ ID NO: 12 with at least one amino acid deletion, wherein the polypeptide has an activity of the polypeptide set forth in any of SEQ ID NO: 2, SEQ ID NO: 5, SEQ ID NO: 8, or SEQ ID NO: 12;

(d) the amino acid sequence as set forth in any of SEQ ID NO: 2, SEQ ID NO: 5, SEQ ID NO: 8, or SEQ ID NO: 12 which has a C- and/or N-terminal truncation, wherein the polypeptide has an activity of the polypeptide set forth in any of SEQ ID NO: 2, SEQ ID NO: 5, SEQ ID NO: 8, or SEQ ID NO: 12; and (e) the amino acid sequence as set forth in any of SEQ ID NO: 2, SEQ ID NO: 5, SEQ ID NO: 8, or SEQ ID NO: 12 with at least one modification selected from the group consisting of amino acid substitutions, amino acid insertions, amino acid deletions, C-terminal truncation, and N-terminal truncation, wherein the polypeptide has an activity of the polypeptide set forth in any of SEQ ID NO: 2, SEQ ID NO: 5, SEQ ID NO: 8, or SEQ ID NO: 12.

Also provided are fusion polypeptides comprising CHL amino acid sequences.

The present invention also provides for an expression vector comprising the isolated nucleic acid molecules as set forth herein, recombinant host cells comprising the recombinant nucleic acid molecules as set forth herein, and a method of producing a CHL polypeptide comprising culturing the host cells and optionally isolating the polypeptide so produced.

A transgenic non-human animal comprising a nucleic acid molecule encoding a CHL polypeptide is also encompassed by the invention. The CHL nucleic acid molecules are introduced into the animal in a manner that allows expression and increased levels of a CHL polypeptide, which may include increased circulating levels. Alternatively, the CHL nucleic acid molecules are introduced into the animal in a manner that prevents expression of endogenous CHL polypeptide (i.e., generates a transgenic animal possessing a CHL polypeptide gene knockout). The transgenic non-human animal is preferably a mammal, and more preferably a rodent, such as a rat or a mouse.

Also provided are derivatives of the CHL polypeptides of the present invention.

Additionally provided are selective binding agents such as antibodies and peptides capable of specifically binding the CHL polypeptides of the invention. Such antibodies and peptides may be agonistic or antagonistic.

Pharmaceutical compositions comprising the nucleotides, polypeptides, or selective binding agents of the invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents.

The CHL polypeptides and nucleic acid molecules of the present invention may be used to treat, prevent, ameliorate, and/or detect diseases and disorders, including those recited herein.

The present invention also provides a method of assaying test molecules to identify a test molecule that binds to a CHL polypeptide. The method comprises contacting a CHL polypeptide with a test molecule to determine the extent of binding of the test molecule to the polypeptide. The method further comprises determining whether such test molecules are agonists or antagonists of a CHL polypeptide. The present invention further provides a method of testing the impact of molecules on the expression of CHL polypeptide or on the activity of CHL polypeptide.

Methods of regulating expression and modulating (i.e., increasing or decreasing) levels of a CHL polypeptide are also encompassed by the invention. One method comprises administering to an animal a nucleic acid molecule encoding a CHL polypeptide. In another method, a nucleic acid molecule comprising elements that regulate or modulate the expression of a CHL polypeptide may be administered. Examples of these methods include gene therapy, cell therapy, and anti-sense therapy as further described herein.

In another aspect of the present invention, the CHL polypeptides may be used for identifying receptors thereof ("CHL polypeptide receptors"). Various forms of "expression cloning" have been extensively used to clone receptors for protein ligands. See, e.g., Simonsen and Lodish, 1994, *Trends Pharmacol. Sci.* 15:43741 and Tartaglia et al., 1995, *Cell* 83:1263-71. The isolation of a CHL polypeptide receptor is useful for identifying or developing novel agonists and antagonists of the CHL polypeptide signaling pathway. Such agonists and antagonists include soluble CHL polypeptide receptors, anti-CHL polypeptide receptor-selective binding agents (such as antibodies and derivatives thereof), small molecules, and antisense oligonucleotides, any of which can be used for treating one or more disease or disorder, including those disclosed herein.

BRIEF DESCRIPTION OF THE FIGURES

FIGS. 1A-1C illustrate the nucleotide sequence of the murine CHL gene (SEQ ID NO: 1) and the deduced amino acid sequence of murine CHL polypeptide (SEQ ID NO: 2). The predicted signal peptide is indicated (underlined);

FIGS. 2A-2D illustrate the nucleotide sequence of the rat CHL gene (SEQ ID NO: 4) and the deduced amino acid sequence of rat CHL polypeptide (SEQ ID NO: 5). The predicted signal peptide is indicated (underlined);

FIGS. 3A-3C illustrate the nucleotide sequence of the human CHL gene (SEQ ID NO: 7) and the deduced amino acid sequence of human CHL polypeptide (SEQ ID NO: 8). The predicted signal peptide is indicated (underlined and/or double-underlined);

FIGS. 4A-4C illustrate the nucleotide sequence of the human CHLd5 gene (SEQ ID NO: 11) and the deduced amino acid sequence of human CHL polypeptide (SEQ ID NO: 12). The predicted signal peptide is indicated (underlined and/or double-underlined);

FIGS. 6A-6E illustrate an amino acid sequence alignment of human CHL polypeptide (Hchl; SEQ ID NO: 8), human CHLd5 polypeptide (Hchld5; SEQ ID NO: 12), murine CHL polypeptide (Mchl; SEQ ID NO: 2), rat CHL polypeptide (Rchl; SEQ ID NO: 5), murine Chordin (Mchordin; SEQ ID NO: 15), rat Chordin (Rchordin; SEQ ID NO: 16), and human Chordin (Hchordin; SEQ ID NO: 17);

DETAILED DESCRIPTION OF THE INVENTION

Figure 5:
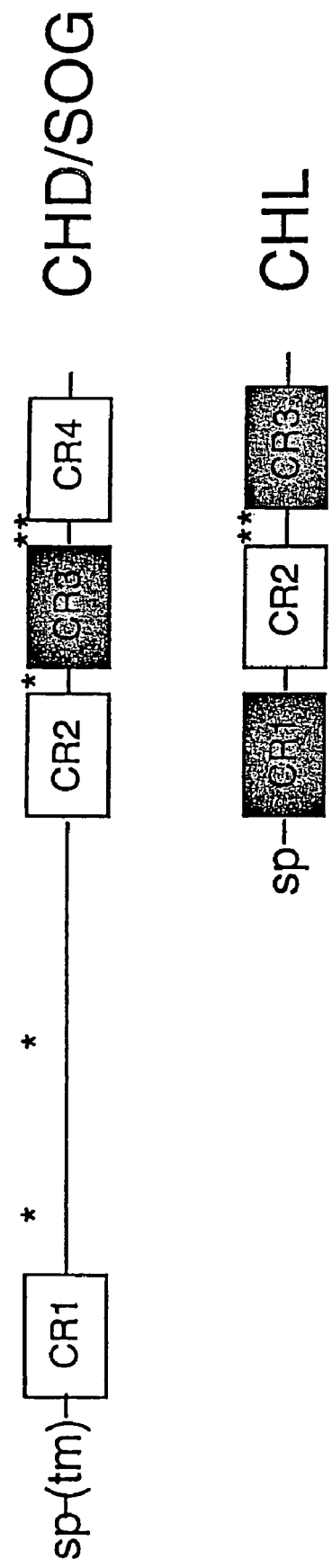
FIG. 5 illustrates the location of pro-collagen repeats (CR1-4) and possible BMP1 cleavage sites (*) in murine CHL polypeptide and CHD/SOG.

The section headings used herein are for organizational purposes only and are not to be construed as limiting the subject matter described. All references cited in this application are expressly incorporated by reference herein.

Definitions

The terms "CHL gene" or "CHL nucleic acid molecule" or "CHL polynucleotide" refer to a nucleic acid molecule comprising or consisting of a nucleotide sequence as set forth in any of SEQ ID NO: 1, SEQ ID NO: 4, SEQ ID NO: 7, or SEQ ID NO: 11, a nucleotide sequence encoding the polypeptide as set forth in any of SEQ ID NO: 2, SEQ ID NO: 5, SEQ ID NO: 8, or SEQ ID NO: 12, a nucleotide sequence of the DNA insert in any of ATCC Deposit Nos. PTA-961, PTA-962, PTA-963, or PTA-964, and nucleic acid molecules as defined herein.

The term "CHL polypeptide allelic variant" refers to one of several possible naturally occurring alternate forms of a gene occupying a given locus on a chromosome of an organism or a population of organisms.

The term "CHL polypeptide splice variant" refers to a nucleic acid molecule, usually RNA, which is generated by alternative processing of intron sequences in an RNA transcript of CHL polypeptide amino acid sequence as set forth in any of SEQ ID NO: 2, SEQ ID NO: 5, SEQ ID NO: 8, or SEQ ID NO: 12.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N-6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "CHL polypeptide" refers to a polypeptide comprising the amino acid sequence of any of SEQ ID NO: 2, SEQ ID NO: 5, SEQ ID NO: 8, or SEQ ID NO: 12 and related polypeptides. Related polypeptides include CHL polypeptide fragments, CHL polypeptide orthologs, CHL polypeptide variants, and CHL polypeptide derivatives, which possess at least one activity of the polypeptide as set forth in any of SEQ ID NO: 2, SEQ ID NO: 5, SEQ ID NO: 8, or SEQ ID NO: 12. CHL polypeptides may be mature polypeptides, as defined herein, and may or may not have an amino-terminal methionine residue, depending on the method by which they are prepared.

The term "CHL polypeptide fragment" refers to a polypeptide that comprises a truncation at the amino-terminus (with or without a leader sequence) and/or a truncation at the carboxyl-terminus of the polypeptide as set forth in any of SEQ ID NO: 2, SEQ ID NO: 5, SEQ ID NO: 8, or SEQ ID NO: 12. The term "CHL polypeptide fragment" also refers to amino-terminal and/or carboxyl-terminal truncations of CHL polypeptide orthologs, CHL polypeptide derivatives, or CHL polypeptide variants, or to amino-terminal and/or carboxyl-terminal truncations of the polypeptides encoded by CHL polypeptide allelic variants or CHL polypeptide splice variants. CHL polypeptide fragments may result from alternative RNA splicing or from in vivo protease activity. Membrane-bound forms of a CHL polypeptide are also contemplated by the present invention. In preferred embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such CHL polypeptide fragments may optionally comprise an amino-terminal methionine residue. It will be appreciated that such fragments can be used, for example, to generate antibodies to CHL polypeptides.

The term "CHL polypeptide ortholog" refers to a polypeptide from another species that corresponds to CHL polypeptide amino acid sequence as set forth in any of SEQ ID NO: 2, SEQ ID NO: 5, SEQ ID NO: 8, or SEQ ID NO: 12. For example, mouse and human CHL polypeptides are considered orthologs of each other.

The term "CHL polypeptide variants" refers to CHL polypeptides comprising amino acid sequences having one or more amino acid sequence substitutions, deletions (such as internal deletions and/or CHL polypeptide fragments), and/or additions (such as internal additions and/or CHL fusion polypeptides) as compared to the CHL polypeptide amino acid sequence set forth in any of SEQ ID NO: 2, SEQ ID NO: 5, SEQ ID NO: 8, or SEQ ID NO: 12 (with or without a leader sequence). Variants may be naturally occurring (e.g., CHL polypeptide allelic variants, CHL polypeptide orthologs, and CHL polypeptide splice variants) or artificially constructed. Such CHL polypeptide variants may be prepared from the corresponding nucleic acid molecules having a DNA sequence that varies accordingly from the DNA sequence as set forth in any of SEQ ID NO: 1, SEQ ID NO: 4, SEQ ID NO: 7, or SEQ ID NO: 11. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "CHL polypeptide derivatives" refers to the polypeptide as set forth in any of SEQ ID NO: 2, SEQ ID NO: 5, SEQ ID NO: 8, or SEQ ID NO: 12, CHL polypeptide fragments, CHL polypeptide orthologs, or CHL polypeptide variants, as defined herein, that have been chemically modified. The term "CHL polypeptide derivatives" also refers to the polypeptides encoded by CHL polypeptide allelic variants or CHL polypeptide splice variants, as defined herein, that have been chemically modified.

The term "mature CHL polypeptide" refers to a CHL polypeptide lacking a leader sequence. A mature CHL polypeptide may also include other modifications such as proteolytic processing of the amino-terminus (with or without a leader sequence) and/or the carboxyl-terminus, cleavage of a smaller polypeptide from a larger precursor, N-linked and/or O-linked glycosylation, and the like. Exemplary mature CHL polypeptides are depicted by the amino acid sequences of SEQ ID NO: 3, SEQ ID NO: 6, SEQ ID NO: 9, SEQ ID NO: 10, SEQ ID NO: 13, and SEQ ID NO: 14.

The term "CHL fusion polypeptide" refers to a fusion of one or more amino acids (such as a heterologous protein or peptide) at the amino- or carboxyl-terminus of the polypeptide as set forth in any of SEQ ID NO: 2, SEQ ID NO: 5, SEQ ID NO: 8, or SEQ ID NO: 12, CHL polypeptide fragments, CHL polypeptide orthologs, CHL polypeptide variants, or CHL derivatives, as defined herein. The term "CHL fusion polypeptide" also refers to a fusion of one or more amino acids at the amino- or carboxyl-terminus of the polypeptide encoded by CHL polypeptide allelic variants or CHL polypeptide splice variants, as defined herein.

The term "biologically active CHL polypeptides" refers to CHL polypeptides having at least one activity characteristic of the polypeptide comprising the amino acid sequence of any of SEQ ID NO: 2, SEQ ID NO: 5, SEQ ID NO: 8, or SEQ ID NO: 12. In addition, a CHL polypeptide may be active as an immunogen; that is, the CHL polypeptide contains at least one epitope to which antibodies may be raised.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The terms "effective amount" and "therapeutically effective amount" each refer to the amount of a CHL polypeptide or CHL nucleic acid molecule used to support an observable level of one or more biological activities of the CHL polypeptides as set forth herein.

The term "pharmaceutically acceptable carrier" or "physiologically acceptable carrier" as used herein refers to one or more formulation materials suitable for accomplishing or enhancing the delivery of the CHL polypeptide, CHL nucleic acid molecule, or CHL selective binding agent as a pharmaceutical composition.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "selective binding agent" refers to a molecule or molecules having specificity for a CHL polypeptide. As used herein, the terms, "specific" and "specificity" refer to the ability of the selective binding agents to bind to human CHL polypeptides and not to bind to human non-CHL polypeptides. It will be appreciated, however, that the selective binding agents may also bind orthologs of the polypeptide as set forth in any of SEQ ID NO: 2, SEQ ID NO: 5, SEQ ID NO: 8, or SEQ ID NO: 12, that is, interspecies versions thereof, such as mouse and rat CHL polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al, *Basic Methods in Molecular Biology* (Elsevier, 1986); and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

Relatedness Of Nucleic Acid Molecules and/or Polypeptides

It is understood that related nucleic acid molecules include allelic or splice variants of the nucleic acid molecule of any of SEQ ID NO: 1, SEQ ID NO: 4, SEQ ID NO: 7, or SEQ ID NO: 11, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide in any of SEQ ID NO: 2, SEQ ID NO: 5, SEQ ID NO: 8, or SEQ ID NO: 12. Such related CHL polypeptides may comprise, for example, an addition and/or a deletion of one or more N-linked or O-linked glycosylation sites or an addition and/or a deletion of one or more cysteine residues.

Related nucleic acid molecules also include fragments of CHL nucleic acid molecules which encode a polypeptide of at least about 25 contiguous amino acids, or about 50 amino acids, or about 75 amino acids, or about 100 amino acids, or about 150 amino acids, or about 200 amino acids, or more than 200 amino acid residues of the CHL polypeptide of any of SEQ ID NO: 2, SEQ ID NO: 5, SEQ ID NO: 8, or SEQ ID NO: 12.

In addition, related CHL nucleic acid molecules also include those molecules which comprise nucleotide sequences which hybridize under moderately or highly stringent conditions as defined herein with the fully complementary sequence of the CHL nucleic acid molecule of any of SEQ ID NO: 1, SEQ ID NO: 4, SEQ ID NO: 7, or SEQ ID NO: 11, or of a molecule encoding a polypeptide, which polypeptide comprises the amino acid sequence as shown in any of SEQ ID NO: 2, SEQ ID NO: 5, SEQ ID NO: 8, or SEQ ID NO: 12, or of a nucleic acid fragment as defined herein, or of a nucleic acid fragment encoding a polypeptide as defined herein. Hybridization probes may be prepared using the CHL sequences provided herein to screen cDNA, genomic or synthetic DNA libraries for related sequences. Regions of the DNA and/or amino acid sequence of CHL polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited).

More stringent conditions (such as higher temperature, lower ionic strength, higher formamide, or other denaturing agent) may also be used—however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et. al., *Nucleic Acid Hybridisation: A Practical Approach* Ch. 4 (IRL Press Limited).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(°C.)=81.5+16.6(\log[Na+])+0.41(\%G+C)-600/N-0.72(\%\text{ formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$Tm=2°$ C per *A-T* base pair $+4°$ C. per *G-C* base pair

*The sodium ion concentration in 6× salt sodium citrate (SSC) is 1M. See Suggs et al., *Developmental Biology Using Purified Genes* 683 (Brown and Fox, eds., 1981).

High stringency washing conditions for oligonucleotides are usually at a temperature of 0-5° C. below the Tm of the oligonucleotide in 6×SSC, 0.1% SDS.

In another embodiment, related nucleic acid molecules comprise or consist of a nucleotide sequence that is at least about 70 percent identical to the nucleotide sequence as shown in any of SEQ ID NO: 1, SEQ ID NO: 4, SEQ ID NO: 7, or SEQ ID NO: 11, or comprise or consist essentially of a nucleotide sequence encoding a polypeptide that is at least about 70 percent identical to the polypeptide as set forth in any of SEQ ID NO: 2, SEQ ID NO: 5, SEQ ID NO: 8, or SEQ ID NO: 12. In preferred embodiments, the nucleotide sequences are about 75 percent, or about 80 percent, or about 85 percent, or about 90 percent, or about 95, 96, 97, 98, or 99 percent identical to the nucleotide sequence as shown in any of SEQ ID NO: 1, SEQ ID NO: 4, SEQ ID NO: 7, or SEQ ID NO: 11, or the nucleotide sequences encode a polypeptide that is about 75 percent, or about 80 percent, or about 85 percent, or about 90 percent, or about 95, 96, 97, 98, or 99 percent identical to the polypeptide sequence as set forth in any of SEQ ID NO: 2, SEQ ID NO: 5, SEQ ID NO: 8, or SEQ ID NO: 12. Related nucleic acid molecules encode polypeptides possessing at least one activity of the polypeptide set forth in any of SEQ ID NO: 2, SEQ ID NO: 5, SEQ ID NO: 8, or SEQ ID NO: 12.

Differences in the nucleic acid sequence may result in conservative and/or non-conservative modifications of the amino acid sequence relative to the amino acid sequence of any of SEQ ID NO: 2, SEQ ID NO: 5, SEQ ID NO: 8, or SEQ ID NO: 12.

Conservative modifications to the amino acid sequence of any of SEQ ID NO: 2, SEQ ID NO: 5, SEQ ID NO: 8, or SEQ ID NO: 12 (and the corresponding modifications to the encoding nucleotides) will produce a polypeptide having functional and chemical characteristics similar to those of CHL polypeptides. In contrast, substantial modifications in the functional and/or chemical characteristics of CHL polypeptides may be accomplished by selecting substitutions in the amino acid sequence of any of SEQ ID NO: 2, SEQ ID NO: 5, SEQ ID NO: 8, or SEQ ID NO: 12 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human CHL polypeptide that are homologous with non-human CHL polypeptides, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the CHL polypeptide, or to increase or decrease the affinity of the CHL polypeptides described herein. Exemplary amino acid substitutions are set forth in Table I.

TABLE I

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in any of SEQ ID NO: 2, SEQ ID NO: 5, SEQ ID NO: 8, or SEQ ID NO: 12 using well-known techniques. For identifying suitable areas of the molecule that may be changed without destroying biological activity, one skilled in the art may target areas not believed to be important for activity. For example, when similar polypeptides with similar activities from the same species or from other species are known, one skilled in the art may compare the amino acid sequence of a CHL polypeptide to such similar polypeptides. With such a comparison, one can identify residues and portions of the molecules that are conserved among similar polypeptides. It will be appreciated that changes in areas of the CHL molecule that are not conserved relative to such similar polypeptides would be less likely to adversely affect the biological activity and/or structure of a CHL polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a CHL polypeptide that correspond to amino acid residues that are important for activity or structure in similar polypeptides. One skilled in the art may opt for chemically similar amino acid substitutions for such predicted important amino acid residues of CHL polypeptides.

One skilled in the art can also analyze the three-dimensional structure and amino acid sequence in relation to that structure in similar polypeptides. In view of such information, one skilled in the art may predict the alignment of amino acid residues of CHL polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each amino acid residue. The variants could be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Opin. Biotechnol.* 7:422-27; Chou et al., 1974, *Biochemistry* 13:22245; Chou et al., 1974, *Biochemistry* 113:211-22; Chou et al., 1978, *Adv. Enzymol. Relat. Areas Mol. Biol.* 47:4548; Chou et al., 1978, *Ann. Rev. Biochem.* 47:251-276; and Chou et al., 1979, *Biophys. J.* 26:367-84. Moreover, computer programs are currently available to assist with predicting secondary structure. One method of predicting secondary structure is based upon homology modeling. For example, two polypeptides or proteins which have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al., 1999, *Nucleic Acids Res.* 27:24447. It has been suggested that there are a limited number of folds in a given polypeptide or protein and that once a critical number of structures have been resolved, structural prediction will become dramatically more accurate (Brenner et al., 1997, *Curr. Opin. Struct. Biol.* 7:369-76).

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science,* 253:164-70; Gribskov et al., 1990, *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

Preferred CHL polypeptide variants include glycosylation variants wherein the number and/or type of glycosylation sites have been altered compared to the amino acid sequence set forth in any of SEQ ID NO: 2, SEQ ID NO: 5, SEQ ID NO: 8, or SEQ ID NO: 12. In one embodiment, CHL polypeptide variants comprise a greater or a lesser number of N-linked glycosylation sites than the amino acid sequence set forth in any of SEQ ID NO: 2, SEQ ID NO: 5, SEQ ID NO: 8, or SEQ ID NO: 12. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred CHL variants include cysteine variants, wherein one or more cysteine residues are deleted or substituted with another amino acid (e.g., serine) as compared to the amino acid sequence set forth in any of SEQ ID NO: 2, SEQ ID NO: 5, SEQ ID NO: 8, or SEQ ID NO: 12. Cysteine variants are useful when CHL polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, related nucleic acid molecules comprise or consist of a nucleotide sequence encoding a polypeptide as set forth in any of SEQ ID NO: 2, SEQ ID NO: 5, SEQ ID NO: 8, or SEQ ID NO: 12 with at least one amino acid insertion and wherein the polypeptide has an activity of the polypeptide set forth in any of SEQ ID NO: 2, SEQ ID NO: 5, SEQ ID NO: 8, or SEQ ID NO: 12, or a nucleotide sequence encoding a polypeptide as set forth in any of SEQ ID NO: 2, SEQ ID NO: 5, SEQ ID NO: 8, or SEQ ID NO: 12 with at least one amino acid deletion and wherein the polypeptide has an activity of the polypeptide set forth in any of SEQ ID NO: 2, SEQ ID NO: 5, SEQ ID NO: 8, or SEQ ID NO: 12. Related nucleic acid molecules also comprise or consist of a nucleotide sequence encoding a polypeptide as set forth in any of SEQ ID NO: 2, SEQ ID NO: 5, SEQ ID NO: 8, or SEQ ID NO: 12 wherein the polypeptide has a carboxyl- and/or amino-terminal truncation and further wherein the polypeptide has an activity of the polypeptide set forth in any of SEQ ID NO: 2, SEQ ID NO: 5, SEQ ID NO: 8, or SEQ ID NO: 12. Related nucleic acid molecules also comprise or consist of a nucleotide sequence encoding a polypeptide as set forth in any of SEQ ID NO: 2, SEQ ID NO: 5, SEQ ID NO: 8, or SEQ ID NO: 12 with at least one modification selected from the group consisting of amino acid substitutions, amino acid insertions, amino acid deletions, carboxyl-terminal truncations, and amino-terminal truncations and wherein the polypeptide has an activity of the polypeptide set forth in any of SEQ ID NO: 2, SEQ ID NO: 5, SEQ ID NO: 8, or SEQ ID NO: 12.

In addition, the polypeptide comprising the amino acid sequence of any of SEQ ID NO: 2, SEQ ID NO: 5, SEQ ID NO: 8, or SEQ ID NO: 12, or other CHL polypeptide, may be fused to a homologous polypeptide to form a homodimer or to a heterologous polypeptide to form a heterodimer. Heterologous peptides and polypeptides include, but are not limited to: an epitope to allow for the detection and/or isolation of a CHL fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in any of SEQ ID NO: 2, SEQ ID NO: 5, SEQ ID NO: 8, or SEQ ID NO: 12, or other CHL polypeptide.

Fusions can be made either at the amino-terminus or at the carboxyl-terminus of the polypeptide comprising the amino acid sequence set forth in any of SEQ ID NO: 2, SEQ ID NO: 5, SEQ ID NO: 8, or SEQ ID NO: 12, or other CHL polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of any of SEQ ID NO: 2, SEQ ID NO: 5, SEQ ID NO: 8, or SEQ ID NO: 12, or other CHL polypeptide, is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas an Fab is short-lived. Capon et al., 1989, Nature 337:525-31.

When constructed together with a therapeutic protein, an Fc domain can provide longer half-life or incorporate such functions as Fc receptor binding, protein A binding, complement fixation, and perhaps even placental transfer. Id. Table II summarizes the use of certain Fc fusions known in the art.

TABLE II

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al., 1995, J. Immunol. 154: 5590-600 |
| IgG1 | TNF receptor | septic shock | Fisher et al., 1996, N. Engl. J. Med. 334: 1697-1702; Van Zee et al., 1996, J. Immunol. 156: 2221-30 |
| IgG, IgA, IgM, or IgE (excluding the first domain) | TNF receptor | inflammation, autoimmune disorders | U.S. Pat. No. 5,808,029 |
| IgG1 | CD4 receptor | AIDS | Capon et al., 1989, Nature 337: 525-31 |
| IgG1, IgG3 | N-terminus of IL-2 | anti-cancer, antiviral | Harvill et al., 1995, Immunotech. 1: 95-105 |
| IgG1 | C-terminus of OPG | osteoarthritis; bone density | WO 97/23614 |
| IgG1 | N-terminus of leptin | anti-obesity | PCT/US 97/23183, filed Dec. 11, 1997 |
| Human Ig Cγ1 | CTLA-4 | autoimmune disorders | Linsley, 1991, J. Exp. Med., 174: 561-69 |

In one example, a human IgG hinge, CH2, and CH3 region may be fused at either the amino-terminus or carboxyl-terminus of the CHL polypeptides using methods known to the skilled artisan. In another example, a human IgG hinge, CH2, and CH3 region may be fused at either the amino-terminus or carboxyl-terminus of a CHL polypeptide fragment (e.g., the predicted extracellular portion of CHL polypeptide).

The resulting CHL fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a natu-rally occurring Fc region, or may be altered to improve certain qualities, such as therapeutic qualifies, circulation time, or reduced aggregation.

Identity and similarity of related nucleic acid molecules and polypeptides are readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heinle, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM J Applied Math.*, 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978)(PAM250 comparison matrix); Henikoff et al., 1992, *Proc. Natl. Acad. Sci USA* 89:10915-19 (BLOSUM 62 comparison matrix)).

Preferred parameters for polypeptide sequence comparison include the following:

Algorithm: Needleman and Wunsch, 1970, *J. Mol. Biol.* 48:443-53;

Comparison matrix: BLOSUM 62 (Henikoff et al., supra);

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:
  Algorithm: Needleman and Wunsch, supra;
  Comparison matrix: matches=+10, mismatch=0
  Gap Penalty: 50
  Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of a CHL polypeptide can readily be obtained in a variety of ways including, without limitation, chemical synthesis, cDNA or genomic library screening, expression library screening, and/or PCR amplification of cDNA.

Recombinant DNA methods used herein are generally those set forth in Sambrook et al., *Molecular Cloning: A Laboratory Manual* (Cold Spring Harbor Laboratory Press, 1989) and/or *Current Protocols in Molecular Biology* (Ausubel et al., eds., Green Publishers Inc. and Wiley and Sons 1994). The invention provides for nucleic acid molecules as described herein and methods for obtaining such molecules.

Where a gene encoding the amino acid sequence of a CHL polypeptide has been identified from one species, all or a portion of that gene may be used as a probe to identify orthologs or related genes from the same species. The probes or primers may be used to screen cDNA libraries from various tissue sources believed to express the CHL polypeptide. In addition, part or all of a nucleic acid molecule having the sequence as set forth in any of SEQ ID NO: 1, SEQ ID NO: 4, SEQ ID NO: 7, or SEQ ID NO: 11 may be used to screen a genomic library to identify and isolate a gene encoding the amino acid sequence of a CHL polypeptide. Typically, conditions of moderate or high stringency will be employed for screening to minimize the number of false positives obtained from the screening.

Nucleic acid molecules encoding the amino acid sequence of CHL polypeptides may also be identified by expression cloning which employs the detection of positive clones based upon a property of the expressed protein. Typically, nucleic acid libraries are screened by the binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence that encodes the amino acid sequence of a CHL polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a CHL polypeptide can be inserted into an expression vector. By introducing the expression vector into an appropriate host, the encoded CHL polypeptide may be produced in large amounts.

Another method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA encoding the amino acid sequence of a CHL polypeptide, are then added to the cDNA along with a polymerase such as Taq polymerase, and the polymerase amplifies the cDNA region between the two primers.

Another means of preparing a nucleic acid molecule encoding the amino acid sequence of a CHL polypeptide is chemical synthesis using methods well known to the skilled artisan such as those described by Engels et al., 1989, *Angew. Chem. Intl. Ed.* 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of a CHL polypeptide will be several hundred nucleotides in length. Nucleic acids larger than about 100 nucleotides can be synthesized as several fragments using these methods. The fragments can then be ligated together to form the full-length nucleotide sequence of a CHL gene. Usually, the DNA fragment encoding the amino-terminus of the polypeptide will have an ATG, which encodes a methionine residue. This methionine may or may not be present on the mature form of the CHL polypeptide, depending on whether the polypeptide produced in the host cell is designed to be secreted from that cell. Other methods known to the skilled artisan may be used as well.

In certain embodiments, nucleic acid variants contain codons which have been altered for optimal expression of a CHL polypeptide in a given host cell. Particular codon alterations will depend upon the CHL polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "Celegans_high.cod," "Celegans_low.cod," "*Drosophila*_high.cod," "Human_high.cod," "Maize_high.cod," and "Yeast_high.cod."

In some cases, it may be desirable to prepare nucleic acid molecules encoding CHL polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Vectors and Host Cells

A nucleic acid molecule encoding the amino acid sequence of a CHL polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a CHL polypeptide may be amplified/expressed in prokaryotic, yeast, insect (baculovirus systems) and/or eukaryotic host cells. Selection of the host cell will depend in part on whether a CHL polypeptide is to be post-translationally modified (e.g., glycosylated and/or phosphorylated). If so, yeast, insect, or mammalian host cells are preferable. For a review of expression vectors, see *Meth. Enz.*, vol. 185 (D. V. Goeddel, ed., *Academic Press* 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the CHL polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification of the CHL polypeptide from the host cell. Affinity purification can be accomplished, for example, by column chromatography using antibodies against the tag as an affinity matrix. Optionally, the tag can subsequently be removed from the purified CHL polypeptide by various means such as using certain peptidases for cleavage.

Flanking sequences may be homologous (ie., from the same species and/or strain as the host cell), heterologous (i.e., from a species other than the host cell species or strain), hybrid (i.e., a combination of flanking sequences from more than one source), or synthetic, or the flanking sequences may be native sequences which normally function to regulate CHL polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein—other than the CHL gene flanking sequences—will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of a CHL polypeptide. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a CHL polypeptide. As a result, increased quantities of CHL polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a CHL polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct a CHL polypeptide out of the host cell. Typically, a nucleotide sequence encoding the signal sequence is positioned in the coding region of a CHL nucleic acid molecule, or directly at the 5' end of a CHL polypeptide coding region. Many signal sequences have been identified, and any of those that are functional in the selected host cell may be used in conjunction with a CHL nucleic acid molecule. Therefore, a signal sequence may be homologous (naturally occurring) or heterologous to the CHL nucleic acid molecule. Additionally, a signal sequence may be chemically synthesized using methods described herein. In most cases, the secretion of a CHL polypeptide from the host cell via the presence of a signal peptide will result in the removal of the signal peptide from the secreted CHL polypeptide. The signal sequence may be a component of the vector, or it may be a part of a CHL nucleic acid molecule that is inserted into the vector.

Included within the scope of this invention is the use of either a nucleotide sequence encoding a native CHL polypeptide signal sequence joined to a CHL polypeptide coding region or a nucleotide sequence encoding a heterologous signal sequence joined to a CHL polypeptide coding region. The heterologous signal sequence selected should be one that is recognized and processed, i.e., cleaved by a signal peptidase, by the host cell. For prokaryotic host cells that do not recognize and process the native CHL polypeptide signal sequence, the signal sequence is substituted by a prokaryotic signal sequence selected, for example, from the group of the alkaline phosphatase, penicillinase, or heat-stable enterotoxin II leaders. For yeast secretion, the native CHL polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired CHL polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the CHL gene especially where the gene used is a full-length genomic sequence or a fragment thereof. Where the intron is not naturally occurring within the gene (as for most cDNAs), the intron may be obtained from another source. The position of the intron with respect to flanking sequences and the CHL gene is generally important, as the intron must be transcribed to be effective. Thus, when a CHL cDNA molecule is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding the CHL polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding CHL polypeptide by removing the promoter from the source DNA by restriction enzyme digestion and inserting the desired promoter sequence into the vector. The native CHL promoter sequence may be used to direct amplification and/or expression of a CHL nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling CHL gene expression include, but are not limited to: the SV40 early promoter region (Bemoist and Chambon, 1981, *Nature* 290:304-10); the CMV promoter; the promoter contained in the 3' long terminal repeat of Rous sarcoma virus (Yamamoto, et al., 1980, *Cell* 22:787-97); the herpes thymidine kinase promoter (Wagner et al., 1981, *Proc. Natl. Acad. Sci. U.S.A.* 78:144445); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Also of interest are the following animal transcriptional control regions, which exhibit tissue specificity and have been utilized in transgenic animals: the elastase I gene control region which is active in pancreatic acinar cells (Swift et al., 1984, *Cell* 38:639-46; Ornitz et al., 1986, *Cold Spring Harbor Symp. Quant. Biol.* 50:399409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region which is active in testicular, breast, lymphoid and mast cells (Leder et al., 1986, *Cell* 45:485-95); the albumin gene control region which is active in liver (Pinkert et al., 1987, *Genes and Devel.* 1:268-76); the alpha-fetoprotein gene control region which is active in liver (Krumlauf et al., 1985, *Mol. Cell. Biol.*, 5:1639-48; Hammer et al., 1987, *Science* 235:53-58); the alpha 1-antitrypsin gene control region which is active in the liver (Kelsey et al., 1987, *Genes and Devel.* 1:161-71); the beta-globin gene control region which is active in myeloid cells (Mogram et al., 1985, *Nature* 315:338-40; Kollias et al., 1986, *Cell* 46:89-94); the myelin basic protein gene control region which is active in oligodendrocyte cells in the brain (Readhead et al., 1987, *Cell* 48:703-12); the myosin light chain-2 gene control region which is active in skeletal muscle (Sani, 1985, *Nature* 314:283-86); and the gonadotropic releasing hormone gene control region which is active in the hypothalamus (Mason et al., 1986, *Science* 234:1372-78).

An enhancer sequence may be inserted into the vector to increase the transcription of a DNA encoding a CHL polypeptide of the present invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-fetoprotein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a CHL nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Pub. No. WO 90/14363) and pFast-BacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems, La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.).

After the vector has been constructed and a nucleic acid molecule encoding a CHL polypeptide has been inserted into the proper site of the vector, the completed vector may be inserted into a suitable host cell for amplification and/or polypeptide expression. The transformation of an expression vector for a CHL polypeptide into a selected host cell may be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, or vertebrate cell). The host cell, when cultured under appropriate conditions, synthesizes a CHL polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(-) cells (Urlaub et al., 1980, *Proc. Natl. Acad. Sci. U.S.A.* 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E.*

*coli* (e.g., HB101, DH5□, DH10, and MC1061) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described, for example, in Kitts et al., 1993, *Biotechniques*, 14:810-17; Lucklow, 1993, *Curr. Opin. Biotechnol.* 4:564-72; and Lucklow et al., 1993, *J. Virol.*, 67:4566-79. Preferred insect cells are Sf-9 and Hi5 (Invitrogen).

One may also use transgenic animals to express glycosylated CHL polypeptides. For example, one may use a transgenic milk-producing animal (a cow or goat, for example) and obtain the present glycosylated polypeptide in the animal milk. One may also use plants to produce CHL polypeptides, however, in general, the glycosylation occurring in plants is different from that produced in mammalian cells, and may result in a glycosylated product which is not suitable for human therapeutic use.

Polypeptide Production

Host cells comprising a CHL polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a CHL polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If a CHL polypeptide has been designed to be secreted from the host cells, the majority of polypeptide may be found in the cell culture medium. If however, the CHL polypeptide is not secreted from the host cells, it will be present in the cytoplasm and/or the nucleus (for eukaryotic host cells) or in the cytosol (for gram-negative bacteria host cells).

For a CHL polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a CHL polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized CHL polypeptide can then be analyzed using gel electrophoresis, immunoprecipitation, or the like. If it is desired to isolate the CHL polypeptide, isolation may be accomplished using standard methods such as those described herein and in Marston et al., 1990, *Meth. Enz.*, 182:264-75.

In some cases, a CHL polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol(DTT)/dithiane DTT, and 2-2-mercaptoethanol(bME)/dithio-b(ME). In many instances, a cosolvent may be used or may be needed to increase the efficiency of the refolding, and the more common reagents used for this purpose include glycerol, polyethylene glycol of various molecular weights, arginine and the like.

If inclusion bodies are not formed to a significant degree upon expression of a CHL polypeptide, then the polypeptide will be found primarily in the supernatant after centrifugation of the cell homogenate. The polypeptide may be further isolated from the supernatant using methods such as those described herein.

The purification of a CHL polypeptide from solution can be accomplished using a variety of techniques. If the polypeptide has been synthesized such that it contains a tag such as Hexahistidine (CHL polypeptide/hexaHis) or other small peptide such as FLAG (Eastman Kodak Co., New Haven, Conn.) or myc (Invitrogen, Carlsbad, Calif.) at either its carboxyl- or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the Qiagen® nickel columns) can be used for purification of CHL polypeptide/polyHis. See, e.g., *Current Protocols in Molecular Biology* § 10.11.8 (Ausubel et al., eds., Green Publishers Inc. and Wiley and Sons 1993).

Additionally, CHL polypeptides may be purified through the use of a monoclonal antibody that is capable of specifically recognizing and binding to a CHL polypeptide.

Other suitable procedures for purification include, without limitation, affinity chromatography, immunoaffinity chromatography, ion exchange chromatography, molecular sieve chromatography, HPLC, electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

CHL polypeptides may also be prepared by chemical synthesis methods (such as solid phase peptide synthesis) using techniques known in the art such as those set forth by Merrifield et al., 1963, *J. Am. Chem. Soc.* 85:2149; Houghten et al., 1985, *Proc Natl Acad. Sci. USA* 82:5132; and Stewart and Young, *Solid Phase Peptide Synthesis* (Pierce Chemical Co. 1984). Such polypeptides may be synthesized with or without a methionine on the amino-terminus. Chemically synthesized CHL polypeptides may be oxidized using methods set forth in these references to form disulfide bridges. Chemically synthesized CHL polypeptides are expected to have comparable biological activity to the corresponding CHL polypeptides produced recombinantly or purified from natural sources, and thus may be used interchangeably with a recombinant or natural CHL polypeptide.

Another means of obtaining CHL polypeptide is via purification from biological samples such as source tissues and/or fluids in which the CHL polypeptide is naturally found. Such purification can be conducted using methods for protein purification as described herein. The presence of the CHL polypeptide during purification may be monitored, for example, using an antibody prepared against recombinantly produced CHL polypeptide or peptide fragments thereof.

A number of additional methods for producing nucleic acids and polypeptides are known in the art, and the methods can be used to produce polypeptides having specificity for CHL polypeptide. See, e.g., Roberts et al., 1997, *Proc. Natl. Acad. Sci. U.S.A.* 94:12297-303, which describes the production of fusion proteins between an mRNA and its encoded peptide. See also, Roberts, 1999, *Curr. Opin. Chem. Biol.* 3:268-73. Additionally, U.S. Pat. No. 5,824,469 describes methods for obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those that exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive CHL polypeptide expression libraries, which can subsequently be used for high throughput phenotypic screening in a variety of assays, such as biochemical assays, cellular assays, and whole organism assays (e.g., plant, mouse, etc.).

Synthesis

It will be appreciated by those skilled in the art that the nucleic acid and polypeptide molecules described herein may be produced by recombinant and other means.

Selective Binding Agents

The term "selective binding agent" refers to a molecule that has specificity for one or more CHL polypeptides. Suitable selective binding agents include, but are not limited to, antibodies and derivatives thereof, polypeptides, and small molecules. Suitable selective binding agents may be prepared using methods known in the art. An exemplary CHL polypeptide selective binding agent of the present invention is capable of binding a certain portion of the CHL polypeptide thereby inhibiting the binding of the polypeptide to a CHL polypeptide receptor.

Selective binding agents such as antibodies and antibody fragments that bind CHL polypeptides are within the scope of the present invention. The antibodies may be polyclonal including monospecific polyclonal; monoclonal (MAbs); recombinant; chimeric; humanized, such as CDR-grafted; human; single chain; and/or bispecific; as well as fragments; variants; or derivatives thereof. Antibody fragments include those portions of the antibody that bind to an epitope on the CHL polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a CHL polypeptide generally are produced in animals (e.g., rabbits or mice) by means of multiple subcutaneous or intraperitoneal injections of CHL polypeptide and an adjuvant. It may be useful to conjugate a CHL polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-CHL antibody titer.

Monoclonal antibodies directed toward CHL polypeptides are produced using any method that provides for the production of antibody molecules by continuous cell lines in culture. Examples of suitable methods for preparing monoclonal antibodies include the hybridoma methods of Kohler et al., 1975, *Nature* 256:495-97 and the human B-cell hybridoma method (Kozbor, 1984, *J. Immunol.* 133:3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with CHL polypeptides.

Monoclonal antibodies of the invention may be modified for use as therapeutics. One embodiment is a "chimeric" antibody in which a portion of the heavy (H) and/or light (L)

chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, *Proc. Natl. Acad. Sci.* 81:6851-55.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, *Nature* 321:522-25; Riechmann et al., 1998, *Nature* 332:323-27; Verhoeyen et al., 1988, *Science* 239:1534-36), by substituting at least a portion of a rodent complementarity-determining region (CDR) for the corresponding regions of a human antibody.

Also encompassed by the invention are human antibodies that bind CHL polypeptides. Using transgenic animals (e.g., mice) that are capable of producing a repertoire of human antibodies in the absence of endogenous immunoglobulin production such antibodies are produced by immunization with a CHL polypeptide antigen (i.e., having at least 6 contiguous amino acids), optionally conjugated to a carrier. See, e.g., Jakobovits et al., 1993, *Proc. Natl. Acad. Sci.* 90:2551-55; Jakobovits et al., 1993, *Nature* 362:255-58; Bruggermann et al., 1993, *Year in Immuno.* 7:33. In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human (rather than, e.g., murine) amino acid sequences, including variable regions which are immunospecific for these antigens. See PCT App. Nos. PCT/US96/05928 and PCT/US93/06926. Additional methods are described in U.S. Pat. No. 5,545,807, PCT App. Nos. PCT/US91/245 and PCT/GB89/01207, and in European Patent Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, *J. Mol. Biol.* 227:381; Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in PCT App. No. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-CHL antibodies of the invention may be employed in any known assay method, such as competitive binding assays, direct and indirect sandwich assays, and immunoprecipitation assays (Sola, *Monoclonal Antibodies: A Manual of Techniques* 147-158 (CRC Press, Inc., 1987)) for the detection and quantitation of CHL polypeptides. The antibodies will bind CHL polypeptides with an affinity that is appropriate for the assay method being employed.

For diagnostic applications, in certain embodiments, anti-CHL antibodies may be labeled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, $^{125}$I, $^{99}$Tc, $^{111}$In, or $^{67}$Ga; a fluorescent or chemiluminescent compound, such as fluorescein isothiocyanate, rhodamine, or luciferin; or an enzyme, such as alkaline phosphatase, □-galactosidase, or horseradish peroxidase (Bayer, et al., 1990, *Meth. Enz.* 184:138-63).

Competitive binding assays rely on the ability of a labeled standard (e.g., a CHL polypeptide, or an immunologically reactive portion thereof) to compete with the test sample analyte (an CHL polypeptide) for binding with a limited amount of anti-CHL antibody. The amount of a CHL polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-CHL antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of a CHL polypeptide. In one embodiment, antagonist antibodies of the invention are antibodies or binding fragments thereof which are capable of specifically binding to a CHL polypeptide and which are capable of inhibiting or eliminating the functional activity of a CHL polypeptide in vivo or in vitro. In preferred embodiments, the selective binding agent, e.g., an antagonist antibody, will inhibit the functional activity of a CHL polypeptide by at least about 50%, and preferably by at least about 80%. In another embodiment, the selective binding agent may be an anti-CHL polypeptide antibody that is capable of interacting with a CHL polypeptide binding partner (a ligand or receptor) thereby inhibiting or eliminating CHL polypeptide activity in vitro or in vivo. Selective binding agents, including agonist and antagonist anti-CHL polypeptide antibodies, are identified by screening assays that are well known in the art.

The invention also relates to a kit comprising CHL selective binding agents (such as antibodies) and other reagents useful for detecting CHL polypeptide levels in biological samples. Such reagents may include a detectable label, blocking serum, positive and negative control samples, and detection reagents.

Microarrays

It will be appreciated that DNA microarray technology can be utilized in accordance with the present invention. DNA microarrays are miniature, high-density arrays of nucleic acids positioned on a solid support, such as glass. Each cell or element within the array contains numerous copies of a single nucleic acid species that acts as a target for hybridization with a complementary nucleic acid sequence (e.g., mRNA). In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA that is specifically bound to each target nucleic acid molecule. In this way, the expression of thousands of genes can be quantitated in a high throughput, parallel manner from a single sample of biological material.

This high throughput expression profiling has a broad range of applications with respect to the CHL molecules of the invention, including, but not limited to: the identification and validation of CHL disease-related genes as targets for therapeutics; molecular toxicology of related CHL molecules and inhibitors thereof; stratification of populations and generation of surrogate markers for clinical trials; and enhancing related CHL polypeptide small molecule drug discovery by aiding in the identification of selective compounds in high throughput screens.

Chemical Derivatives

Chemically modified derivatives of CHL polypeptides may be prepared by one skilled in the art, given the disclosures described herein. CHL polypeptide derivatives are modified in a manner that is different—either in the type or location of the molecules naturally attached to the polypeptide. Derivatives may include molecules formed by the deletion of one or more naturally-attached chemical groups. The polypeptide comprising the amino acid sequence of any of SEQ ID NO: 2, SEQ ID NO: 5, SEQ ID NO: 8, or SEQ ID NO: 12, or other CHL polypeptide, may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules which may be used to prepare covalently attached CHL polypeptide multimers.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the polypeptide comprising the amino acid sequence of any of SEQ ID NO: 2, SEQ ID NO: 5, SEQ ID NO: 8, or SEQ ID NO: 12, or other CHL polypeptide, becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the CHL polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, *Focus on Growth Factors* 3:4-10; European Patent Nos. 0154316 and 0401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, CHL polypeptides may be chemically coupled to biotin. The biotin/CHL polypeptide molecules are then allowed to bind to avidin, resulting in tetravalent avidin/biotin/CHL polypeptide molecules. CHL polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present CHL polypeptide derivatives include those described herein for CHL polypeptides. However, the CHL polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents; rabbits, goats, sheep, or other farm animals, in which the genes encoding native CHL polypeptide have been disrupted (i.e., "knocked out") such that the level of expression of CHL polypeptide is significantly decreased or completely abolished. Such animals may be prepared using techniques and methods such as those described in U.S. Pat. No. 5,557,032.

The present invention further includes non-human animals such as mice, rats, or other rodents; rabbits, goats, sheep, or other farm animals, in which either the native form of a CHL gene for that animal or a heterologous CHL gene is over-expressed by the animal, thereby creating a "transgenic" animal. Such transgenic animals may be prepared using well known methods such as those described in U.S. Pat. No. 5,489,743 and PCT Pub. No. WO 94/28122.

The present invention further includes non-human animals in which the promoter for one or more of the CHL polypeptides of the present invention is either activated or inactivated (e.g., by using homologous recombination methods) to alter the level of expression of one or more of the native CHL polypeptides.

These non-human animals may be used for drug candidate screening. In such screening, the impact of a drug candidate on the animal may be measured. For example, drug candidates may decrease or increase the expression of the CHL gene. In certain embodiments, the amount of CHL polypeptide that is produced may be measured after the exposure of the animal to the drug candidate. Additionally, in certain embodiments, one may detect the actual impact of the drug candidate on the animal. For example, over-expression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Assaying for Other Modulators of CHL Polypeptide Activity

In some situations, it may be desirable to identify molecules that are modulators, ie., agonists or antagonists, of the activity of CHL polypeptide. Natural or synthetic molecules that modulate CHL polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of a CHL polypeptide. Most commonly, a test molecule will interact directly with a CHL polypeptide. However, it is also contemplated that a test molecule may also modulate CHL polypeptide activity indirectly, such as by affecting CHL gene expression, or by binding to a CHL polypeptide binding partner (e.g., receptor or ligand). In one embodiment, a test molecule will bind to a CHL polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with CHL polypeptides are encompassed by the present invention. In certain embodiments, a CHL polypeptide is incubated with a test molecule under conditions that permit the interaction of the test molecule with a CHL polypeptide, and the extent of the interaction is measured. The test molecule can be screened in a substantially purified form or in a crude mixture.

In certain embodiments, a CHL polypeptide agonist or antagonist may be a protein, peptide, carbohydrate, lipid, or small molecular weight molecule that interacts with CHL polypeptide to regulate its activity. Molecules which regulate CHL polypeptide expression include nucleic acids which are complementary to nucleic acids encoding a CHL polypeptide, or are complementary to nucleic acids sequences which direct or control the expression of CHL polypeptide, and which act as anti-sense regulators of expression.

Once a test molecule has been identified as interacting with a CHL polypeptide, the molecule may be further evaluated for its ability to increase or decrease CHL polypeptide activity. The measurement of the interaction of a test molecule with CHL polypeptide may be carried out in several formats, including cell-based binding assays, membrane binding assays, solution-phase assays, and immunoassays. In general, a test molecule is incubated with a CHL polypeptide for a specified period of time, and CHL polypeptide activity is determined by one or more assays for measuring biological activity.

The interaction of test molecules with CHL polypeptides may also be assayed directly using polyclonal or monoclonal antibodies in an immunoassay. Alternatively, modified forms of CHL polypeptides containing epitope tags as described herein may be used in solution and immunoassays.

In the event that CHL polypeptides display biological activity through an interaction with a binding partner (e.g., a receptor or a ligand), a variety of in vitro assays may be used to measure the binding of a CHL polypeptide to the corresponding binding partner (such as a selective binding agent, receptor, or ligand). These assays may be used to screen test molecules for their ability to increase or decrease the rate and/or the extent of binding of a CHL polypeptide to its binding partner. In one assay, a CHL polypeptide is immobilized in the wells of a microtiter plate. Radiolabeled CHL polypeptide binding partner (for example, iodinated CHL polypeptide binding partner) and a test molecule can then be added either one at a time (in either order) or simultaneously to the wells. After incubation, the wells can be washed and counted for radioactivity, using a scintillation counter, to determine the extent to which the binding partner bound to the CHL polypeptide. Typically, a molecule will be tested over a range of concentrations, and a series of control wells lacking one or more elements of the test assays can be used for accuracy in the evaluation of the results. An alternative to this method involves reversing the "positions" of the proteins, i.e., immobilizing CHL polypeptide binding partner to the microtiter plate wells, incubating with the test molecule and radiolabeled CHL polypeptide, and determining the extent of CHL polypeptide binding. See, e.g., *Current Protocols in Molecular Biology*, chap. 18 (Ausubel et al., eds., Green Publishers Inc. and Wiley and Sons 1995).

As an alternative to radiolabeling, a CHL polypeptide or its binding partner may be conjugated to biotin, and the presence of biotinylated protein can then be detected using streptavidin linked to an enzyme, such as horse radish peroxidase (HRP) or alkaline phosphatase (AP), which can be detected colorometrically, or by fluorescent tagging of streptavidin. An antibody directed to a CHL polypeptide or to a CHL polypeptide binding partner, and which is conjugated to biotin, may also be used for purposes of detection following incubation of the complex with enzyme-linked streptavidin linked to AP or HRP.

A CHL polypeptide or a CHL polypeptide binding partner can also be immobilized by attachment to agarose beads, acrylic beads, or other types of such inert solid phase substrates. The substrate-protein complex can be placed in a solution containing the complementary protein and the test compound. After incubation, the beads can be precipitated by centrifugation, and the amount of binding between a CHL polypeptide and its binding partner can be assessed using the methods described herein. Alternatively, the substrate-protein complex can be immobilized in a column with the test molecule and complementary protein passing through the column. The formation of a complex between a CHL polypeptide and its binding partner can then be assessed using any of the techniques described herein (e.g., radiolabelling or antibody binding).

Another in vitro assay that is useful for identifying a test molecule which increases or decreases the formation of a complex between a CHL polypeptide binding protein and a CHL polypeptide binding partner is a surface plasmon resonance detector system such as the BIAcore assay system (Pharmacia, Piscataway, N.J.). The BIAcore system is utilized as specified by the manufacturer. This assay essentially involves the covalent binding of either CHL polypeptide or a CHL polypeptide binding partner to a dextran-coated sensor chip that is located in a detector. The test compound and the other complementary protein can then be injected, either simultaneously or sequentially, into the chamber containing the sensor chip. The amount of complementary protein that binds can be assessed based on the change in molecular mass that is physically associated with the dextran-coated side of the sensor chip, with the change in molecular mass being measured by the detector system.

In some cases, it may be desirable to evaluate two or more test compounds together for their ability to increase or decrease the formation of a complex between a CHL polypeptide and a CHL polypeptide binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for an effect on the formation of a complex between a CHL polypeptide and CHL polypeptide binding partner. The assays may be automated to screen compounds generated in phage display, synthetic peptide, and chemical synthesis libraries.

Compounds which increase or decrease the formation of a complex between a CHL polypeptide and a CHL polypeptide binding partner may also be screened in cell culture using cells and cell lines expressing either CHL polypeptide or CHL polypeptide binding partner. Cells and cell lines may be obtained from any mammal, but preferably will be from human or other primate, canine, or rodent sources. The binding of a CHL polypeptide to cells expressing CHL polypeptide binding partner at the surface is evaluated in the presence or absence of test molecules, and the extent of binding may be determined by, for example, flow cytometry using a biotinylated antibody to a CHL polypeptide binding partner. Cell culture assays can be used advantageously to further evaluate compounds that score positive in protein binding assays described herein.

Cell cultures can also be used to screen the impact of a drug candidate. For example, drug candidates may decrease or increase the expression of the CHL gene. In certain embodiments, the amount of CHL polypeptide or a CHL polypeptide fragment that is produced may be measured after exposure of the cell culture to the drug candidate. In certain embodiments, one may detect the actual impact of the drug candidate on the cell culture. For example, the over-expression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Internalizing Proteins

The tat protein sequence (from HIV) can be used to internalize proteins into a cell. See, e.g., Falwell et al., 1994, *Proc. Natl. Acad. Sci. U.S.A.* 91:664-68. For example, an 11 amino acid sequence (Y-G-R-K-K-R-R-Q-R-R-R; SEQ ID NO: 18) of the HIV tat protein (termed the "protein transduction domain," or TAT PDT) has been described as mediating delivery across the cytoplasmic membrane and the nuclear membrane of a cell. See Schwarze et al., 1999, *Science* 285:1569-72; and Nagahara et al., 1998, *Nat. Med.* 4:1449-52. In these procedures, FITC-constructs (FITC-labeled G-G-G-G-Y-G-R-K-K-R-R-Q-R-R-R; SEQ ID NO: 19), which penetrate tissues following intraperitoneal administration, are prepared, and the binding of such constructs to cells is detected by fluorescence-activated cell sorting (FACS) analysis. Cells treated with a tat-☐-gal fusion protein will demonstrate ☐-gal activity. Following injection, expression of such a construct can be detected in a number of tissues, including liver, kidney, lung, heart, and brain tissue. It is believed that such constructs undergo some degree of unfolding in order to enter the cell, and as such, may require a refolding following entry into the cell.

It will thus be appreciated that the tat protein sequence may be used to internalize a desired polypeptide into a cell. For example, using the tat protein sequence, a CHL antagonist (such as an anti-CHL selective binding agent, small molecule, soluble receptor, or antisense oligonucleotide) can be administered intracellularly to inhibit the activity of a CHL molecule. As used herein, the term "CHL molecule" refers to both CHL nucleic acid molecules and CHL polypeptides as defined herein. Where desired, the CHL protein itself may also be internally administered to a cell using these procedures. See also, Straus, 1999, *Science* 285:1466-67.

Cell Source Identification Using CHL Polypeptide

In accordance with certain embodiments of the invention, it may be useful to be able to determine the source of a certain cell type associated with a CHL polypeptide. For example, it may be useful to determine the origin of a disease or pathological condition as an aid in selecting an appropriate therapy. In certain embodiments, nucleic acids encoding a CHL polypeptide can be used as a probe to identify cells described herein by screening the nucleic acids of the cells with such a probe. In other embodiments, one may use anti-CHL polypeptide antibodies to test for the presence of CHL polypeptide in cells, and thus, determine if such cells are of the types described herein.

CHL Polypeptide Compositions and Administration

Therapeutic compositions are within the scope of the present invention. Such CHL polypeptide pharmaceutical compositions may comprise a therapeutically effective amount of a CHL polypeptide or a CHL nucleic acid molecule in admixture with a pharmaceutically or physiologically acceptable formulation agent selected for suitability with the mode of administration. Pharmaceutical compositions may comprise a therapeutically effective amount of one or more CHL polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See *Remington's Pharmaceutical Sciences* (18th Ed., A. R. Gennaro, ed., Mack Publishing Company 1990.

The optimal pharmaceutical composition will be determined by a skilled artisan depending upon, for example, the intended route of administration, delivery format, and desired dosage. See, e.g., *Remington's Pharmaceutical Sciences*, supra. Such compositions may influence the physical state, stability, rate of in vivo release, and rate of in vivo clearance of the CHL molecule.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute. In one embodiment of the present invention, CHL polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the CHL polypeptide product may be formulated as a lyophilizate using appropriate excipients such as sucrose.

The CHL polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired CHL molecule in a pharmaceutically acceptable vehicle. A particularly suitable vehicle for parenteral injection is sterile distilled water in which a CHL molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, CHL polypeptide may be formulated as a dry powder for inhalation. CHL polypeptide or nucleic acid molecule inhalation solutions may also be formulated with a propellant for aerosol delivery. In yet another embodiment, solutions may be nebulized. Pulmonary administration is further described in PCT Pub. No. WO 94/20069, which describes the pulmonary delivery of chemically modified proteins.

It is also contemplated that certain formulations may be administered orally. In one embodiment of the present invention, CHL polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the CHL polypeptide. Diluents, flavorings, low melting point waxes, vegetable oils, lubricants, suspending agents, tablet disintegrating agents, and binders may also be employed.

Another pharmaceutical composition may involve an effective quantity of CHL polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional CHL polypeptide pharmaceutical compositions will be evident to those skilled in the art, including formulations involving CHL polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., PCT/US93/00829, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and European Patent No. 058481), copolymers of L-glutamic acid and gamma ethyl-L-glutamate (Sidman et al., 1983, *Biopolymers* 22:547-56), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(–)-3-hydroxybutyric acid (European Patent No. 133988). Sustained-release compositions may also include liposomes, which can be prepared by any of several methods known in the art. See, e.g., Eppstein et al., 1985, *Proc. Natl. Acad. Sci. USA* 82:3688-92; and European Patent Nos. 036676, 088046, and 143949.

The CHL pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of a CHL pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the CHL molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 □g/kg to up to about 100 mg/kg or more, depending on the factors mentioned above. In other embodiments, the dosage may range from 0.1 □g/kg up to about 100 mg/kg; or 1 □g/kg up to about 100 mg/kg; or 5 □g/kg up to about 100 mg/kg.

The frequency of dosing will depend upon the pharmacokinetic parameters of the CHL molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use CHL polypeptide pharmaceutical compositions in an ex vivo manner. In such instances, cells, tissues, or organs that have been removed from the patient are exposed to CHL polypeptide pharmaceutical compositions after which the cells, tissues, or organs are subsequently implanted back into the patient.

In other cases, a CHL polypeptide can be delivered by implanting certain cells that have been genetically engineered, using methods such as those described herein, to express and secrete the CHL polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

As discussed herein, it may be desirable to treat isolated cell populations (such as stem cells, lymphocytes, red blood cells, chondrocytes, neurons, and the like) with one or more CHL polypeptides. This can be accomplished by exposing the isolated cells to the polypeptide directly, where it is in a form that is permeable to the cell membrane.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally-silent CHL gene, or an under-expressed gene, and thereby produce a cell which expresses therapeutically efficacious amounts of CHL polypeptides.

Homologous recombination is a technique originally developed for targeting genes to induce or correct mutations in transcriptionally active genes. Kucherlapati, 1989, *Prog. in Nucl. Acid Res. & Mol. Biol.* 36:301. The basic technique was developed as a method for introducing specific mutations into specific regions of the mammalian genome (Thomas et al., 1986, *Cell* 44:419-28; Thomas and Capecchi, 1987, *Cell* 51:503-12; Doetschman et al., 1988, *Proc. Natl. Acad. Sci. U.S.A.* 85:8583-87) or to correct specific mutations within defective genes (Doetschman et al., 1987, *Nature* 330:576-78). Exemplary homologous recombination techniques are described in U.S. Pat. No. 5,272,071; European Patent Nos. 9193051 and 505500; PCT/US90/07642, and PCT Pub No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with or control the expression of a CHL polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired CHL polypeptide. The control element controls a portion of the DNA present in the host cell genome. Thus, the expression of the desired CHL polypeptide may be achieved not by transfection of DNA that encodes the CHL gene itself, but rather by the use of targeting DNA (containing regions of homology with the endogenous gene of interest) coupled with DNA regulatory segments that provide the endogenous gene sequence with recognizable signals for transcription of a CHL gene.

In an exemplary method, the expression of a desired targeted gene in a cell (i.e., a desired endogenous cellular gene) is altered via homologous recombination into the cellular genome at a preselected site, by the introduction of DNA which includes at least a regulatory sequence, an exon, and a splice donor site. These components are introduced into the chromosomal (genomic) DNA in such a manner that this, in effect, results in the production of a new transcription unit (in which the regulatory sequence, the exon, and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, CHL polypeptide production from a cell's endogenous CHL gene involves first using homologous recombination to place a recombination sequence from a site-specific recombination system (e.g., Cre/loxP, FLP/FRT) (Sauer, 1994, *Curr. Opin. Biotechnol.*, 5:521-27; Sauer, 1993, *Methods Enzymol.*, 225:890-900) upstream of (i.e., 5' to) the cell's endogenous genomic CHL polypeptide coding region. A plasmid containing a recombination site homologous to the site that was placed just upstream of the genomic CHL polypeptide coding region is introduced into the modified cell line along with the appropriate recombinase enzyme. This recombinase causes the plasmid to integrate, via the plasmid's recombination site, into the recombination site located just upstream of the genomic CHL polypeptide coding region in the cell line (Baubonis and Sauer, 1993, *Nucleic Acids Res.* 21:2025-29; O'Gorman et al., 1991, *Science* 251:1351-55). Any flanking sequences known to increase transcription (e.g., enhancer/promoter, intron, translational enhancer), if properly positioned in this plasmid, would integrate in such a manner as to create a new or modified transcriptional unit resulting in de novo or increased CHL polypeptide production from the cell's endogenous CHL gene.

A further method to use the cell line in which the site specific recombination sequence had been placed just upstream of the cell's endogenous genomic CHL polypeptide coding region is to use homologous recombination to introduce a second recombination site elsewhere in the cell line's genome. The appropriate recombinase enzyme is then introduced into the two-recombination-site cell line, causing a recombination event (deletion, inversion, and translocation) (Sauer, 1994, *Curr. Opin. Biotechnol.*, 5:521-27; Sauer, 1993, *Methods Enzymol.*, 225:890-900) that would create a new or modified transcriptional unit resulting in de novo or increased CHL polypeptide production from the cell's endogenous CHL gene.

An additional approach for increasing, or causing, the expression of CHL polypeptide from a cell's endogenous CHL gene involves increasing, or causing, the expression of a gene or genes (e.g., transcription factors) and/or decreasing the expression of a gene or genes (e.g., transcriptional repressors) in a manner which results in de novo or increased CHL polypeptide production from the cell's endogenous CHL gene. This method includes the introduction of a non-naturally occurring polypeptide (e.g., a polypeptide comprising a site specific DNA binding domain fused to a transcriptional factor domain) into the cell such that de novo or increased CHL polypeptide production from the cell's endogenous CHL gene results.

The present invention further relates to DNA constructs useful in the method of altering expression of a target gene. In certain embodiments, the exemplary DNA constructs comprise: (a) one or more targeting sequences, (b) a regulatory sequence, (c) an exon,. and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of CHL polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a CHL polypeptide, which nucleotides may be used as targeting sequences.

CHL polypeptide cell therapy, e.g., the implantation of cells producing CHL polypeptides, is also contemplated. This embodiment involves implanting cells capable of synthesizing and secreting a biologically active form of CHL polypeptide. Such CHL polypeptide-producing cells can be cells that are natural producers of CHL polypeptides or may be recombinant cells whose ability to produce CHL polypeptides has been augmented by transformation with a gene encoding the desired CHL polypeptide or with a gene augmenting the expression of CHL polypeptide. Such a modification may be accomplished by means of a vector suitable for delivering the gene as well as promoting its expression and secretion. In order to minimize a potential immunological reaction in patients being administered a CHL polypeptide, as may occur with the administration of a polypeptide of a foreign species, it is preferred that the natural cells producing CHL polypeptide be of human origin and produce human CHL polypeptide. Likewise, it is preferred that the recombinant cells producing CHL polypeptide be transformed with an expression vector containing a gene encoding a human CHL polypeptide.

Implanted cells may be encapsulated to avoid the infiltration of surrounding tissue. Human or non-human animal cells may be implanted in patients in biocompatible, semipermeable polymeric enclosures or membranes that allow the release of CHL polypeptide, but that prevent the destruction of the cells by the patient's immune system or by other detrimental factors from the surrounding tissue. Alternatively, the patient's own cells, transformed to produce CHL polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (PCT Pub. No. WO 95/05452 and PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in PCT Pub. No. WO 91/10425 (Aebischer et al.). See also, PCT Pub. No. WO 91/10470 (Aebischer et al.); Winn et al., 1991, *Exper.* *Neurol.* 113:322-29; Aebischer et al., 1991, *Exper. Neurol.* 111:269-75; and Tresco et al., 1992, *ASAIO* 38:17-23.

In vivo and in vitro gene therapy delivery of CHL polypeptides is also envisioned. One example of a gene therapy technique is to use the CHL gene (either genomic DNA, cDNA, and/or synthetic DNA) encoding a CHL polypeptide which may be operably linked to a constitutive or inducible promoter to form a "gene therapy DNA construct." The promoter may be homologous or heterologous to the endogenous CHL gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the CHL gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see PCT Pub. Nos. WO 96/41865, WO 97/31898, and WO 97/31899). The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See Aridor et al., 2000, *Science* 287:816-17 and Rivera et al., 2000, Science 287:826-30.

Other suitable control means or gene switches include, but are not limited to, the systems described herein. Mifepristone (RU486) is used as a progesterone antagonist. The binding of a modified progesterone receptor ligand-binding domain to the progesterone antagonist activates transcription by forming a dimer of two transcription factors that then pass into the nucleus to bind DNA. The ligand-binding domain is modified to eliminate the ability of the receptor to bind to the natural ligand. The modified steroid hormone receptor system is further described in U.S. Pat. No. 5,364,791 and PCT Pub. Nos. WO 96/40911 and WO 97/10337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain, DNA-binding domain, and ligand-binding domain to initiate transcription. The ecdysone system is further described in U.S. Pat. No. 5,514,578 and PCT Pub. Nos. WO 97/38117, WO 96/37609, and WO 93/03162.

Another control means uses a positive tetracycline-controllable transactivator. This system involves a mutated tet repressor protein DNA-binding domain (mutated tet R4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding CHL polypeptide into cells via local injection of a CHL nucleic acid molecule or by other appropriate viral or non-viral delivery vectors. Heffi 1994, *Neurobiology* 25:1418-35. For example, a nucleic acid molecule encoding a CHL polypeptide may be contained in an adeno-associated virus (AAV) vector for delivery to the targeted cells (see, e.g., Johnson, PCT Pub. No. WO 95/34670; PCT App. No. PCT/US95/07178). The recombinant AAV genome typically contains AAV inverted terminal repeats flanking a DNA sequence encoding a CHL polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 (involving adenoviral vectors), U.S. Pat. No. 5,672,510 (involving retroviral vectors), U.S. Pat. No. 5,635,399 (involving retroviral vectors expressing cytokines).

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and PCT Pub. No. WO 96/40958 (involving nuclear ligands).

It is also contemplated that CHL gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous CHL polypeptide expression in a cell via gene therapy is to insert one or more enhancer elements into the CHL polypeptide promoter, where the enhancer elements can serve to increase transcriptional activity of the CHL gene. The enhancer elements used will be selected based on the tissue in which one desires to activate the gene—enhancer elements known to confer promoter activation in that tissue will be selected. For example, if a gene encoding a CHL polypeptide is to be "turned on" in T-cells, the Ick promoter enhancer element may be used. Here, the functional portion of the transcriptional element to be added may be inserted into a fragment of DNA containing the CHL polypeptide promoter (and optionally, inserted into a vector and/or 5' and/or 3' flanking sequences) using standard cloning techniques. This construct, known as a "homologous recombination construct," can then be introduced into the desired cells either ex vivo or in vivo.

Gene therapy also can be used to decrease CHL polypeptide expression by modifying the nucleotide sequence of the endogenous promoter. Such modification is typically accomplished via homologous recombination methods. For example, a DNA molecule containing all or a portion of the promoter of the CHL gene selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding CHL gene. The deletion of the TATA box or the transcription activator binding site in the promoter may be accomplished by generating a DNA construct comprising all or the relevant portion of the CHL polypeptide promoter (from the same or a related species as the CHL gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Therapeutic Uses

CHL nucleic acid molecules, polypeptides, and agonists and antagonists thereof can be used to treat, diagnose, ameliorate, or prevent a number of diseases, disorders, or conditions, including those recited herein.

CHL polypeptide agonists and antagonists include those molecules which regulate CHL polypeptide activity and either increase or decrease at least one activity of the mature form of the CHL polypeptide. Agonists or antagonists may be co-factors, such as a protein, peptide, carbohydrate, lipid, or small molecular weight molecule, which interact with CHL polypeptide and thereby regulate its activity. Potential polypeptide agonists or antagonists include antibodies that react with either soluble or membrane-bound forms of CHL polypeptides that comprise part or all of the extracellular domains of the said proteins. Molecules that regulate CHL polypeptide expression typically include nucleic acids encoding CHL polypeptide that can act as anti-sense regulators of expression.

Preliminary biological and biochemical characterization suggests several therapeutic utilities for CHL polypeptides. CHL polypeptides, fragments, variants, and/or derivatives may be used to prevent or treat bone diseases such as osteopetrosis and osteoporosis, aid in tissue regeneration and wound healing, or function in hematopoietic stem cell-genesis and expansion.

In clinical settings, the adult body is the major therapeutic target, and proteins that are produced and work in a normal healthy body may, therefore, give significant therapeutic benefits when they have been shown to function in organ homeostasis. In an adult organism, one of the major roles of the BMP-family of gene products—specifically BMP2 and BMP4—is the regulation of bone-mass. Since BMP 1 has been shown to cleave and inactivate CHD and probably CHL polypeptide, and has been isolated with BMP2 and BMP3 from bone (Wozney et al., 1988, *Science* 242:1528-34; Celeste et al, 1990, *Proc. Nat. Acad. Sci. USA* 87: 984347), it is possible that CHL polypeptide and CHD play key regulatory roles in osteogenesis. This implies that one of the rate-limiting steps for the control of bone mass may be the regulation of the BMP2/4 activity through CHL polypeptide and BMP 1, as well as through Noggin. Thus, by administering CHL polypeptides or anti-CHL antibodies, the amount and activity of CHL polypeptide may be controlled and the bone density of in an adult decreased or increased as desired.

The direct delivery of BMP4 or other BMP-family members to the regenerating bone through the blood stream appears to be a straightforward therapeutic concept for treatment of osteopetrosis. However, it may be difficult to accomplish since BMP4 is known, to travel only a short distance in vivo (Jones et al., 1996, *Curr. Biol.* 6:1468-75). By forming a complex with CHL polypeptide, BMP may migrate further— as in the case of CHD in an embryo leading to the formation of a concentration gradient for BMP4 (Jones and Smith, 1998, *Dev. Biol.* 194:12-17). Patients suffering from either osteopetrosis or osteoporosis would benefit from improved treatments.

BMP polypeptides have been shown to function in organ formation during late embryogenesis. It is well-known that organ formation in embryonic kidney, lung, and gut are affected by BMP4 expression (Hogan 1996, *Genes Dev.* 10:1580-94). CHL polypeptide is shown herein to be expressed in the lung and small intestine, while CHD is known to be expressed in the kidney. Thus, it is possible that by using a combination of BMP4 and CHL polypeptide (or of BMP and CHD) the proliferation and differentiation of progenitor cells in these tissues could be controlled permitting for the regulation of tissue regeneration or wound healing in vivo.

Agonists or antagonists of CHL polypeptide function may be used (simultaneously or sequentially) in combination with one or more cytokines, growth factors, antibiotics, anti-inflammatories, and/or chemotherapeutic agents as is appropriate for the condition being treated.

Other diseases or disorders caused by or mediated by undesirable levels of CHL polypeptides are encompassed within the scope of the invention. Undesirable levels include excessive levels of CHL polypeptides and sub-normal levels of CHL polypeptides.

Uses of CHL Nucleic Acids and Polypeptides

Nucleic acid molecules of the invention (including those that do not themselves encode biologically active polypeptides) may be used to map the locations of the CHL gene and related genes on chromosomes. Mapping may be done by techniques known in the art, such as PCR amplification and in situ hybridization.

CHL nucleic acid molecules (including those that do not themselves encode biologically active polypeptides), may be useful as hybridization probes in diagnostic assays to test, either qualitatively or quantitatively, for the presence of a CHL nucleic acid molecule in mammalian tissue or bodily fluid samples.

Other methods may also be employed where it is desirable to inhibit the activity of one or more CHL polypeptides. Such inhibition may be effected by nucleic acid molecules that are complementary to and hybridize to expression control sequences (triple helix formation) or to CHL mRNA. For example, antisense DNA or RNA molecules, which have a sequence that is complementary to at least a portion of a CHL gene can be introduced into the cell. Anti-sense probes may be designed by available techniques using the sequence of the CHL gene disclosed herein. Typically, each such antisense molecule will be complementary to the start site (5' end) of each selected CHL gene. When the antisense molecule then hybridizes to the corresponding CHL mRNA, translation of this mRNA is prevented or reduced. Anti-sense inhibitors provide information relating to the decrease or absence of a CHL polypeptide in a cell or organism.

Alternatively, gene therapy may be employed to create a dominant-negative inhibitor of one or more CHL polypeptides. In this situation, the DNA encoding a mutant polypeptide of each selected CHL polypeptide can be prepared and introduced into the cells of a patient using either viral or non-viral methods as described herein. Each such mutant is typically designed to compete with endogenous polypeptide in its biological role.

In addition, a CHL polypeptide, whether biologically active or not, may be used as an immunogen, that is, the polypeptide contains at least one epitope to which antibodies may be raised. Selective binding agents that bind to a CHL polypeptide (as described herein) may be used for in vivo and in vitro diagnostic purposes, including, but not limited to, use in labeled form to detect the presence of CHL polypeptide in a body fluid or cell sample. The antibodies may also be used to prevent, treat, or diagnose a number of diseases and disorders, including those recited herein. The antibodies may bind to a CHL polypeptide so as to diminish or block at least one activity characteristic of a CHL polypeptide, or may bind to a polypeptide to increase at least one activity characteristic of a CHL polypeptide (including by increasing the pharmacokinetics of the CHL polypeptide).

The CHL polypeptides of the present invention can be used to clone CHL polypeptide receptors, using an expression cloning strategy. Radiolabeled ($^{125}$Iodine) CHL polypeptide or affinity/activity-tagged CHL polypeptide (such as an Fc fusion or an alkaline phosphatase fusion) can be used in binding assays to identify a cell type or cell line or tissue that expresses CHL polypeptide receptors. RNA isolated from such cells or tissues can be converted to cDNA, cloned into a mammalian expression vector, and transfected into mammalian cells (such as COS or 293 cells) to create an expression library. A radiolabeled or tagged CHL polypeptide can then be used as an affinity ligand to identify and isolate from this library the subset of cells that express the CHL polypeptide receptors on their surface. DNA can then be isolated from these cells and transfected into mammalian cells to create a secondary expression library in which the fraction of cells expressing CHL polypeptide receptors is many-fold higher than in the original library. This enrichment process can be repeated iteratively until a single recombinant clone containing a CHL polypeptide receptor is isolated. Isolation of the CHL polypeptide receptors is useful for identifying or developing novel agonists and antagonists of the CHL polypeptide signaling pathway. Such agonists and antagonists include soluble CHL polypeptide receptors, anti-CHL polypeptide receptor antibodies, small molecules, or antisense oligonucleotides, and they may be used for treating, preventing, or diagnosing one or more of the diseases or disorders described herein.

In addition to indicating that CHL polypeptides interact with and inhibit the activity of BMP4, preliminary biological and biochemical characterization suggests several other utilities for CHL polypeptides.

Since BMP2 is the most closely related BMP-family member to BMP4, CHL polypeptide may also inhibit the function of BMP2. In addition, interactions with other BMP-family members may also be detected. Furthermore, CHL polypeptide may also interact with a novel set of proteins that are not related to the BMP family. The murine, rat, and human CHL nucleic acids described herein are useful tools for obtaining the corresponding recombinant proteins. The recombinant CHL polypeptides of the present invention can be used to identify proteins that interact with this protein. For example, the CHL polypeptides may also be used to determine whether CHL polypeptide interacts directly with a membrane or intracellular receptor.

The murine, rat, and human CHL nucleic acids of the present invention are also useful tools for isolating the corresponding chromosomal CHL polypeptide genes. For example, mouse chromosomal DNA containing CHL sequences can be used to construct knockout mice, thereby permitting an examination of the in vivo role for CHL polypeptide. The human CHL genomic DNA can be used to identify heritable tissue-degenerating diseases.

As described herein, CHL mRNA has been identified in a set of bone marrow stroma cell lines that are known to support hematopoietic stem cells and early progenitor cells, but has not been identified in stroma cell lines which support only committed progenitor cells (see Example 4). On the other hand, the CHL mRNA is detected in bone marrow, but not in fetal liver or in peripheral blood leukocytes. These observations imply that CHL polypeptide or CHL-interacting proteins might have some function in regulating hematopoietic stem cell survival and maintenance, specifically in the bone marrow environment. The CHL polypeptides and CHL nucleic acids described herein may provide useful tools for in vitro expansion of hematopoietic stem cells. Alternatively, BMP4 or other putative CHL-interacting molecules can be used for regulating the survival and maintenance of hematopoietic stem cells.

BMP4 is an essential factor for generating hematopoietic progenitor cells from the mouse ES cells. However, the effective concentration of BMP4 falls into a narrow range (0.5 ng/ml to 5 ng/ml), which is consistent with the idea that the difference in the active concentration of BMP correlates with the difference in the resulting cell-type from the totipotent epiblast. A system for the reproducible in vitro generation of hematopoietic stem cells from ES cells has not yet been disclosed. However, it may be achieved by precise control of the concentration of BMP4. The CHL polypeptides, anti-CHL antibodies, and CHL nucleic acids of the present invention would be useful tools for optimizing the culturing conditions for the in vitro generation of hematopoietic stem cells from ES cells.

Primitive hematopoietic stem cells have been recently defined in the mouse yolk sac (Yoder et al., 1997, *Proc. Natl. Acad. Sci. USA* 94:6776-80). This subclass of hematopoietic stem cells does not exhibit a marrow-repopulating activity in adults. However, when exposed to a newborn liver environment, the primitive stem cells are converted to long-term marrow-repopulating stem cells (i.e., definitive stem cells). This can also be accomplished by culturing the primitive stem cells on certain stroma cell lines. The long-term maintenance of the definitive stem cells in culture and the long-term generation of the definitive stem cells from the primitive stem cells in culture have not yet been distinguished. The preferential expression of CHL mRNA in the stroma cell lines which support the definitive stem cell survival and maintenance suggests that interactions between BMP and CHL polypeptide or between BMP and CHD system might also function in the stem cell maintenance and/or generation. Thus the recombinant CHL polypeptides and CHL antibodies of the present invention may be useful tools for the both long-term maintenance and generation of the definitive hematopoietic stem cells in vitro. Alternatively, BMP4 or putative, novel CHL-interacting molecules can be used for controlling these processes.

The primitive hematopoietic stem cells have yet to be fully characterized. While primitive stem cells may be of a lymphocytic cell type, such cells may also be mesodermal precursors which are able to generate hematopoietic cell types as well as other mesodermal progeny. In support of this idea, adult bone marrow has recently been shown to contain endothelial progenitor cells, cells that regenerate liver (Petersen et al., 1999, *Science* 284:1168-70), and a common stem cell that has a capability of deriving endothelial cells, muscle cells and hematopoietic cells in vivo (Ferrari et al., 1998, *Science* 279: 1528-30). Furthermore, the osteoblast cell lineage, which consists of the bone marrow stroma, is known to be derived from a mesenchymal stem cell that is present in bone marrow. The possibility that a common mesodermal stem cell is responsible for the generation of both stroma and hematopoietic cells has also been previously speculated.

Nevertheless, the fact that growth and differentiation of osteoblasts are regulated by BMP and that CHL polypeptide is expressed in bone marrow suggest that the BMP/CHL system might be involved in biological processes in which the bone marrow-mesodermal stem cells are involved. In this respect, the recombinant CHL polypeptides and CHL antibodies of the present invention may be useful for characterization of such multi-lineage stem cells.

As described herein, primitive hematopoietic stem cells have been found in the mouse yolk sac. This class of hematopoietic stem cells has been shown to possess marrow-repopulating activity only following pre-exposure in a new-born liver environment. Since the presence of a primitive stem cell activity has never been investigated in the conventional hematopoietic sites of bone marrow, umbilical cord blood, and fetal liver, this suggests that there may be as yet unidentified (i.e. primitive) hematopoietic stem cells in these tissues. If the primitive hematopoietic stem cell is present in such hematopoietic tissues, it can be a novel target for ex vivo expansion, and could be a better target for gene transfer since such cells are more primitive than definitive stem cells. The concept that the conversion of primitive stem cells to definitive stem cells can also be achieved in culture on certain stroma cell lines makes this idea clinically feasible.

As discussed herein, through the use of BMP/CHD or BMP/CHL it may be possible to regulate primitive hematopoietic stem cells and thereby control adult-marrow repopulating stem cells. Alternatively, it may be possible to control stem cell genesis from a mesodermal stem cell. Thus, the CHL polypeptides and nucleic acids of the present invention, along with BMP, may be useful for ex vivo expansion of hematopoietic stem cells and gene therapy performed through such cells.

Deposits of cDNA encoding murine, rat, and human CHL polypeptide and human CHLd5 polypeptide, subcloned into pSPORT1 (Gibco BRL), having Accession Nos. PTA-961, PTA-962, PTA-963, or PTA-964, were made with the American Type Culture Collection, 10801 University Boulevard, Manassas, Va. 20110-2209 on Nov. 16, 1999.

The following examples are intended for illustration purposes only, and should not be construed as limiting the scope of the invention in any way.

EXAMPLE 1

Cloning of the Murine CHL Polypeptide Gene

Generally, materials and methods as described in Sambrook et al. supra were used to clone and analyze the gene encoding murine CHL polypeptide.

Sequences encoding murine CHL polypeptide were isolated from a normalized cDNA library of the mouse bone marrow stroma cell line, OP9, as a sequence with statistically meaningful homology to the CR domains of chicken CHD. The normalized cDNA library was prepared by using the polymerase chain reaction (PCR) based normalization procedure of Takahashi and Ko, 1994, *Genomics* 23: 202-10.

Part of the normalized OP9 library of $3\times10^5$ independent clones was screened for clones containing signal-like sequences using the amylase-based yeast signal trap method (U.S. patent application Ser. No. 09/026,959). Individual colonies that gave a positive signal were picked, and the cDNA insert was amplified from each yeast clone by PCR using vector primers. The partial clone carrying the 5'-half of the coding region (clone tmsn1-00001-h4) was detected among approximately 400 inserts sequenced.

A full-length cDNA clone (clone tmsn1-00001-h4-wze/agp-61975-a1) was then isolated from an OP9 full-length cDNA library constructed in the pcDNA3.1 expression vector (Invitrogen). Forty-eight individual sub-pools of the full-length cDNA library, each containing $2\times10^4$ independent clones, were screened using a probe generated from the partial CHL nucleic acid sequence by PCR using the primers 2125-05 (5'-A-G-T-G-C-C-C-A-G-C-T-T-T-A-G-T-C-C-A-C-3'; SEQ ID NO: 20) and 2125-06 (5'-G-A-G-A-T-G-A-G-G-A-A-T-A-T-G-C-A-C-G-G-3'; SEQ ID NO: 21). The resulting 350 bp PCR fragment contained 267 bp of the CHL polypeptide coding region and 84 bp 5' non-coding sequence.

Four positive clones were obtained from a screen of $2\times10^4$ recombinant cDNA clones. The clone with the longest insert size (clone tmsn1-00001-h4-wze/agp-61975-a1) was sequenced.

Sequence analysis of the full-length cDNA for murine CHL polypeptide (clone 1-2) indicated that the gene comprises a 999 bp open reading frame encoding a protein of 333 amino acids (FIGS. 1A-1C). The murine CHL polypeptide sequence is predicted to contain a signal peptide (FIG. 1A, predicted signal peptide indicated by underline).

EXAMPLE 2

Cloning of the Rat CHL Polypeptide Gene

Generally, materials and methods as described in Sambrook et al. supra were used to clone and analyze the gene encoding rat CHL polypeptide.

Sequences encoding rat CHL polypeptide were isolated from a normalized rat prostate cDNA library as a result of expression-sequence-tag (EST) sequencing. A partial rat CHL nucleic acid sequence (clone srpb2-00279-a4) of 370 base pairs in length and encoding a polypeptide fragment that is 39% identical to CHD was identified through such analysis. The corresponding full-length rat CHL cDNA (clone srpb2-00279-a4-wz) was subsequently isolated by screening an oligo(dT)-primed rat prostate cDNA library using the partial rat CHL nucleic acid sequence as a probe.

Sequence analysis of the full-length cDNA for rat CHL polypeptide indicated that the gene comprises a 1146 bp open reading frame encoding a protein of 382 amino acids (FIGS. 2A-2D). The rat CHL polypeptide sequence is predicted to contain a signal peptide (FIG. 2A, predicted signal peptide indicated by underline).

EXAMPLE 3

Cloning of the Human CHL Polypeptide Gene

Generally, materials and methods as described in Sambrook et al. supra were used to clone and analyze the gene encoding human CHL polypeptide.

Sequences encoding human CHL polypeptide were isolated from a human fetal brain cDNA library (Stratagene) using the partial rat CHL cDNA clone as a probe. The human CHL cDNA clone that was recovered lacked the amino-terminal end of the coding sequence, and the 5'-end part of the CHL mRNA was cloned separately using RACE methodology using a human heart marathon-ready cDNA kit (Clontech). The first round of PCR was performed using the 5'-primer supplied with the kit (AP 1) and the gene specific primer 2127-58 (5'-G-A-C-A-T-C-T-G-A-C-T-C-G-G-C-T-G-C-3'; SEQ ID NO: 22). The second PCR amplification was performed using the 5'-primer supplied with the kit (AP2) and the gene specific primer 2212-48 (5'-T-C-A-C-G-C-A-G-T-A-A-A-C-C-A-A-C-3'; SEQ ID NO: 23).

The resulting PCR fragment was subcloned into the TOPO cloning vector (Invitrogen), the nucleotide sequence confirmed by sequencing, and the 5' human CHL fragment was then inserted into the partial human CHL cDNA described above in order to reconstruct the full-length human CHL cDNA (termed srpb2-00279-a4-wze).

Sequence analysis of the full-length cDNA for human CHL polypeptide indicated that the gene comprises a 1356 bp open reading frame encoding a protein of 452 amino acids (FIGS. 3A-3C). The human CHL polypeptide sequence is predicted to contain a signal peptide (FIG. 3A, predicted signal peptide indicated by underlined and/or double-underline).

A second form of human CHL cDNA, designated as CHLd5, was identified during the course of constructing the human CHL-FLAG fusion polypeptide (see Example 6). A full-length human CHLd5 DNA fragment in which the stop codon was replaced by a Bam HI site was obtained by PCR using heart cDNA (Clonetech) as a template and the primers 2235-53 (5'-C-G-G-A-A-T-T-C-G-C-C-A-C-C-A-T-G-G-G-A-G-G-C-A-T-G-A-A-A-T-A-C-A-T-C-T-T-T-3'; SEQ ID NO: 24) and 2235-54 (5'-C-G-C-G-G-A-T-C-C-A-C-A-G-T-G-G-C-C-C-T-T-T-T-C-A-G-A-T-C-T-C-T-C-3'; SEQ ID NO: 25). The amplified PCR product was digested with Eco RI and Bam HI, gel purified, and then inserted into the pFLAG-CMVSa expression vector (Sigma). The resulting CHL-FLAG expression plasmid is designated as pFLAGh-CHLd5. This form of human CHL polypeptide has an internal deletion of 5 amino acids ($Gly^{319}$-$Lys^{320}$-$Lys^{321}$-$Ala^{322}$-$Lys^{323}$) immediately following CR3. Interestingly, the identical peptide is present in the murine CHL polypeptide, but is lacking in the rat CHL polypeptide. Therefore, the rat CHL polypeptide may correspond to CHLd5.

Sequence analysis of the full-length cDNA for human CHLd5 polypeptide indicated that the gene comprises a 1341 bp open reading frame encoding a protein of 447 amino acids (FIGS. 4A-4C). The human CHLd5 polypeptide sequence is predicted to contain a signal peptide (FIG. 4A, predicted signal peptide indicated by underlined and/or double-underline).

Computer analysis of the isolated murine, rat, and human sequences indicated that they possessed three repeated CR motifs, in contrast to the four repeats observed in CHD. Although CR motifs have been found in a number of other known proteins, including pro-collagen, a homology search in GenBank revealed that the CHL polypeptide motifs were most closely related to the CR motifs of CHD/SOG. The CR1 and CR3 of CHL polypeptide were particularly found to be highly homologous to the CR3 of CHD/SOD (indicated by gray boxes; FIG. 5). The structural arrangement of the three CR motifs in CHL polypeptide seems to correspond to that of CR2-CR4 in CHD since CHL polypeptide lacks one CR motif as compared to CHD and also lacks the long gap between the CR1 and CR2 motifs of CHD. FIGS. 6A-6E illustrate the amino acid sequence alignment of human CHL polypeptide, human CHLd5 polypeptide, murine CHL polypeptide, rat CHL polypeptide, murine CHD, rat CHD, and human CHD. The murine CHL polypeptide is notable in that it is approximately one-third the size of the 948 amino acid murine CHD protein.

EXAMPLE 4

CHL mRNA Expression

Multiple human or murine tissue northern blots (for mouse, mouse embryo, human, human II, and human immune system II, obtained from Clontech) were probed using a $^{32}$P-dCTP-labeled 350 bp PCR fragment generated by amplification of the murine CHL cDNA clone (see Example 1).

The Northern blots were prehybridized in Express Hybridization solution (Clontech) for 1 hour at 68° C. and then were hybridized in the same solution with the addition of 1.3 ng/mL of labeled probe for 1 hour at 68° C. Following hybridization, the filters were washed three times in 2×SSC and 0.05% SDS for 10 minutes at room temperature, and then twice in 0.1×SSC and 0.1% SDS for 20 minutes at 50° C. Following washing, the blots were subjected to autoradiography.

Figure 7A:
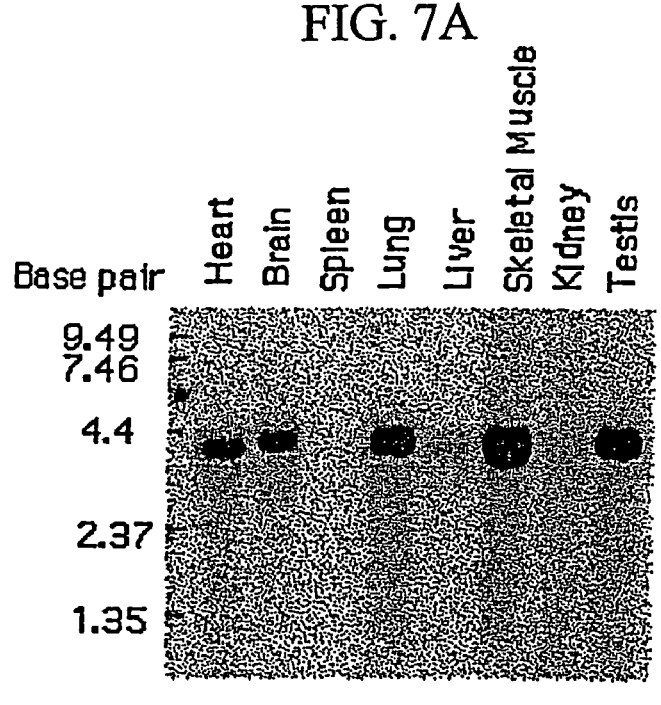
FIGS. 7A-7B illustrate the expression of murine CHL mRNA and beta-actin as a control in (7A) adult tissues and (7B) embryos.
Figure 8:
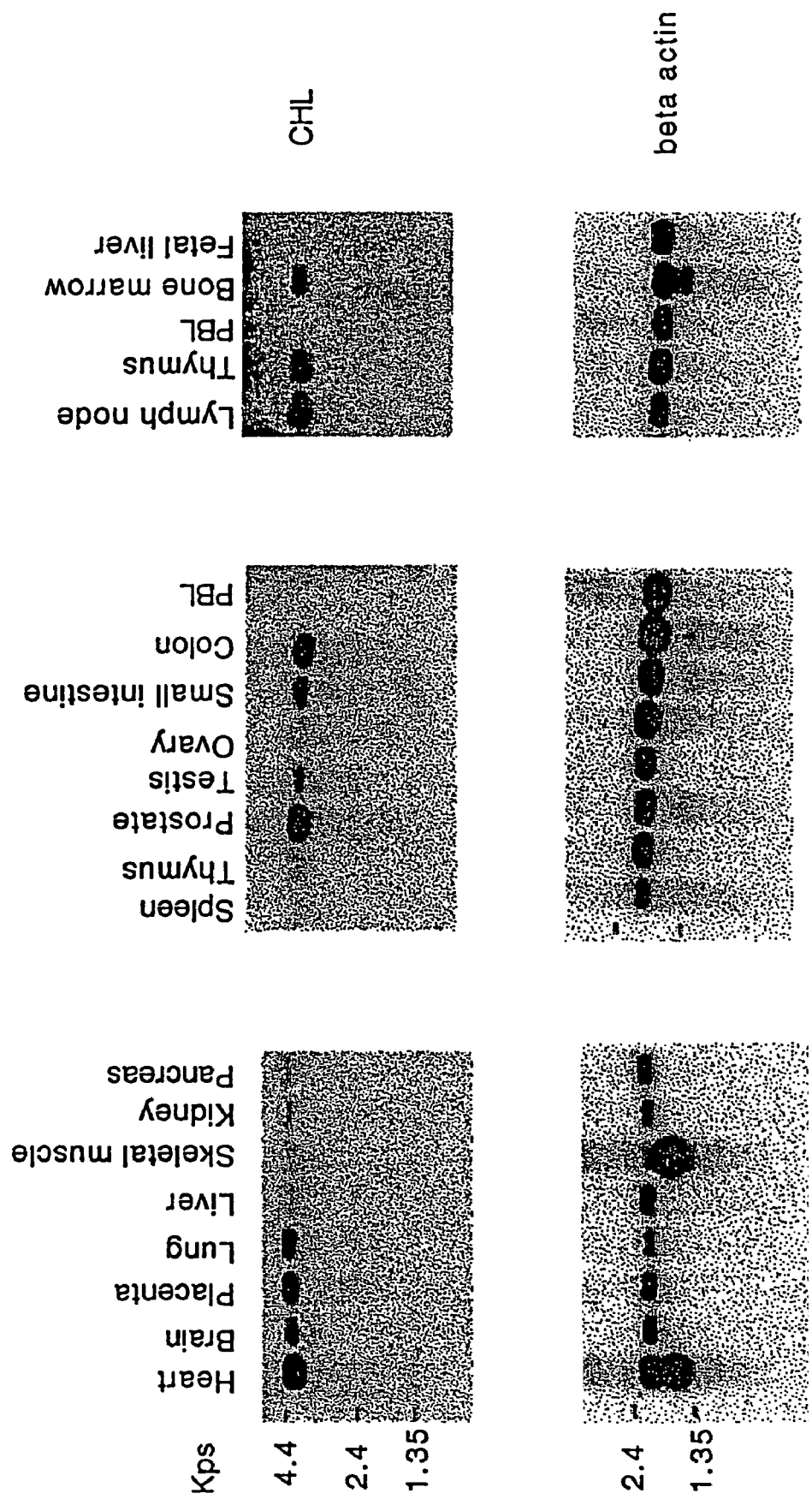
FIG. 8 illustrates the expression of human CHL mRNA and beta-actin as a control in adult and fetal human tissues.

Among the adult murine tissues analyzed, transcripts of 4 kb in length having the highest expression were detected in the heart, brain, lung, and testis, transcripts with a moderate level of expression were detected in skeletal muscle, and transcripts with a lower level of expression were detected in the spleen, liver, and kidney (FIG. 7A). Analysis of human tissue northern blots identified an abundant human transcript of 4-7 kb in length that cross reacts with the murine probe in the heart, brain, lung, placenta, prostate, small intestine and colon (mucosal lining). Lower levels of expression of this transcript were detected in liver, skeletal muscle, kidney, pancreas, thymus, lymph node, spleen, bone marrow, testis, and ovary (FIG. 8). Expression below the level of detection on northern blots was found in peripheral blood leukocytes and fetal liver.

Figure 7B:
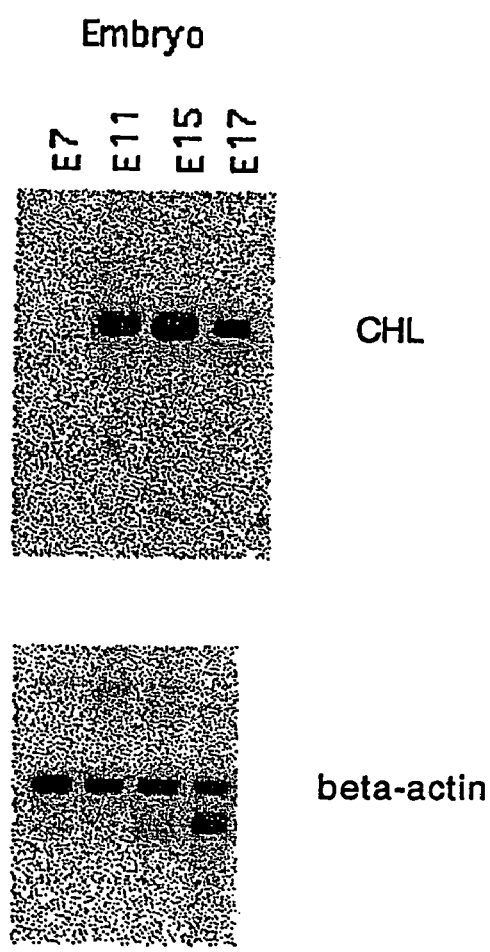

A comparative Northern analysis in mouse embryos provides additional support for a relationship between CHL polypeptide and CHD/SOG. While CHD/SOG has been shown to be expressed in E7 embryos—and at much lower levels in E11, E15 and E17 embryos (Pappano et al., 1998, *Genomics* 52:236-39)—CHL RNA, in contrast, was found to be expressed in E11, E15, and E17 embryos but not in E7 embryos (FIG. 7B). Furthermore, while CHL expression is detected in the adult heart and lung expression of CHD/SOG in these tissues is very weak (Pappano et al., 1998 *Genomics* 52:236-39). In contrast, CHD/SOG expression is detected in the spleen, liver, and kidney (Pappano et al., 1998, *Genomics* 52:236-39), while CHL expression in these tissues is very weak or below the level of detection. The expression pattern of CHL mRNA seems to contrast that of CHD/SOG with only a few exceptions (i.e., brain and testis). Nevertheless, these results suggest that CHL polypeptide is not only structurally related to CHD/SOG but may also be functionally related.

Figure 9A:
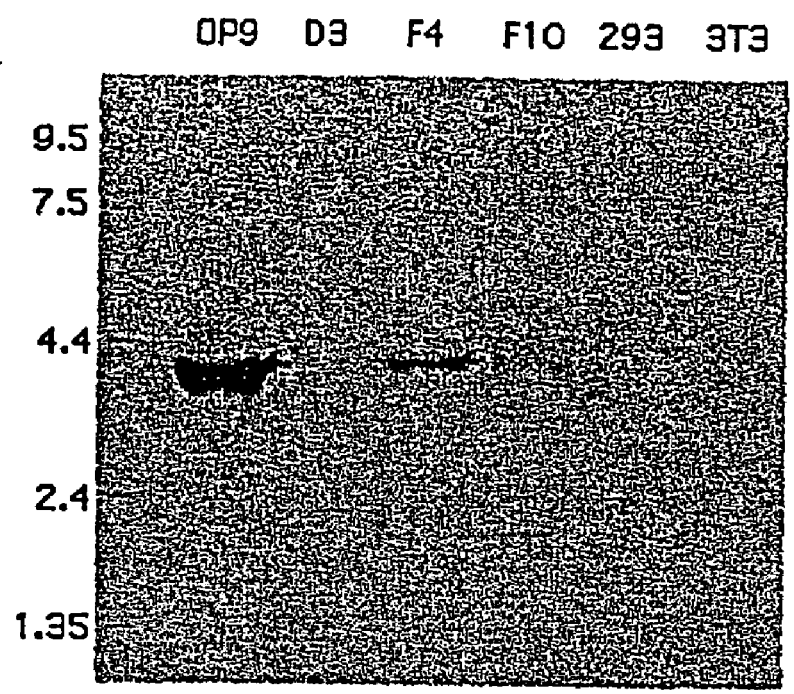
FIGS. 9A-9B illustrate the differential expression of murine CHL mRNA and beta-actin as a control among the stroma cell lines OP9, D3, F4, and F10.
Figure 9B:
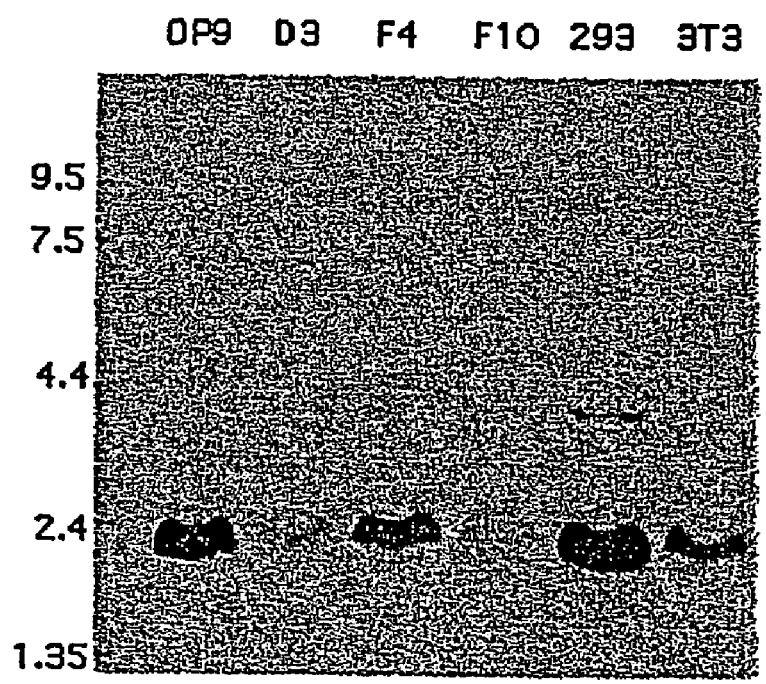

Northern analyses were also performed on several bone-marrow-derived stroma cell lines (FIGS. 9A-9B). CHL polypeptide seems to be expressed differentially according to their properties. The stroma cell lines F10 and F4, which are known to support early hematopoietic progenitor cells (probably stem cells) in the formation of delayed cobblestone areas (CAs), were found to express CHL mRNA (FIG. 9A). However, the stroma cell line D3—a variant supporting only mature hematopoietic progenitor cells in the formation of short-term CAs, does not express CHL mRNA. In this respect, CHL expression correlates with the ability of stroma cells to support survival, maintenance, and differentiation of hematopoietic stem cells. Since bone marrow, but not fetal liver, was found to express CHL mRNA (FIG. 8), it would be expected that CHL polypeptide is expressed by a stroma cell population specific to bone marrow rather than to fetal liver. The results of the Northern analysis also suggest that CHL polypeptide is probably not expressed in mature hematopoietic cell lineages, as peripheral blood leukocytes were found to not express appreciable levels of CHL mRNA (FIG. 8).

The expression of CHL mRNA was localized by in situ hybridization. In situ hybridization was performed as described in Harlow and Lane, *Using Antibodies: A Laboratory Manual* (Cold Spring Harbor Laboratory Press, 1999), using antisense-RNAs synthesized with SP6 RNA polymerase (Ambion, Austin, Tex.) from pSPmCHL5'. The pSPmCHL5' vector was prepared by removing the region between the Cla I and Not I sites of pSPORTmCHL and then linearizing the vector with Eco RI.

Figure 10:
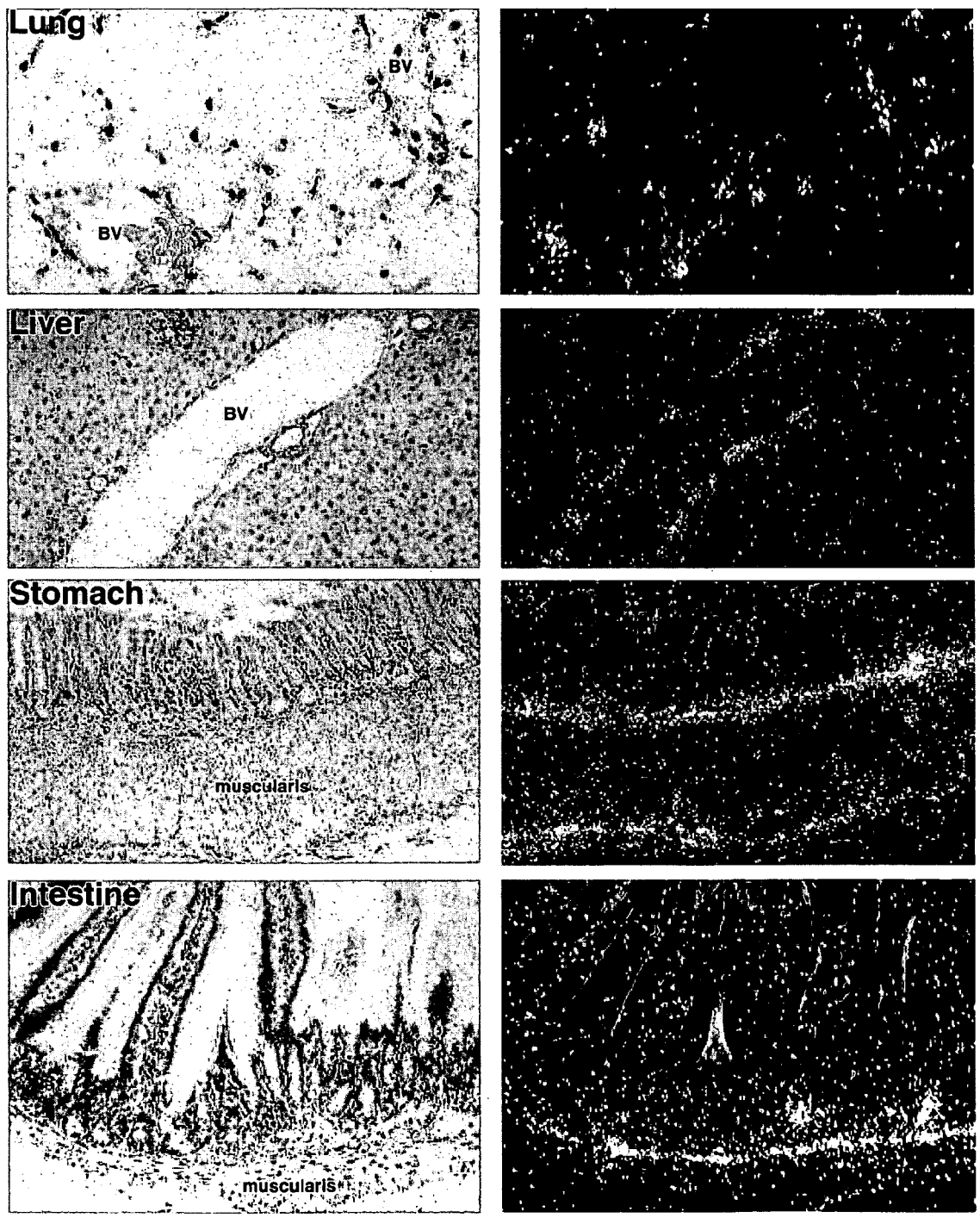
FIG. 10 illustrates the expression of murine CHL mRNA as detected by in situ hybridization in normal adult mouse lung, liver, stomach, and intestine (BV=blood vessel)
Figure 11:
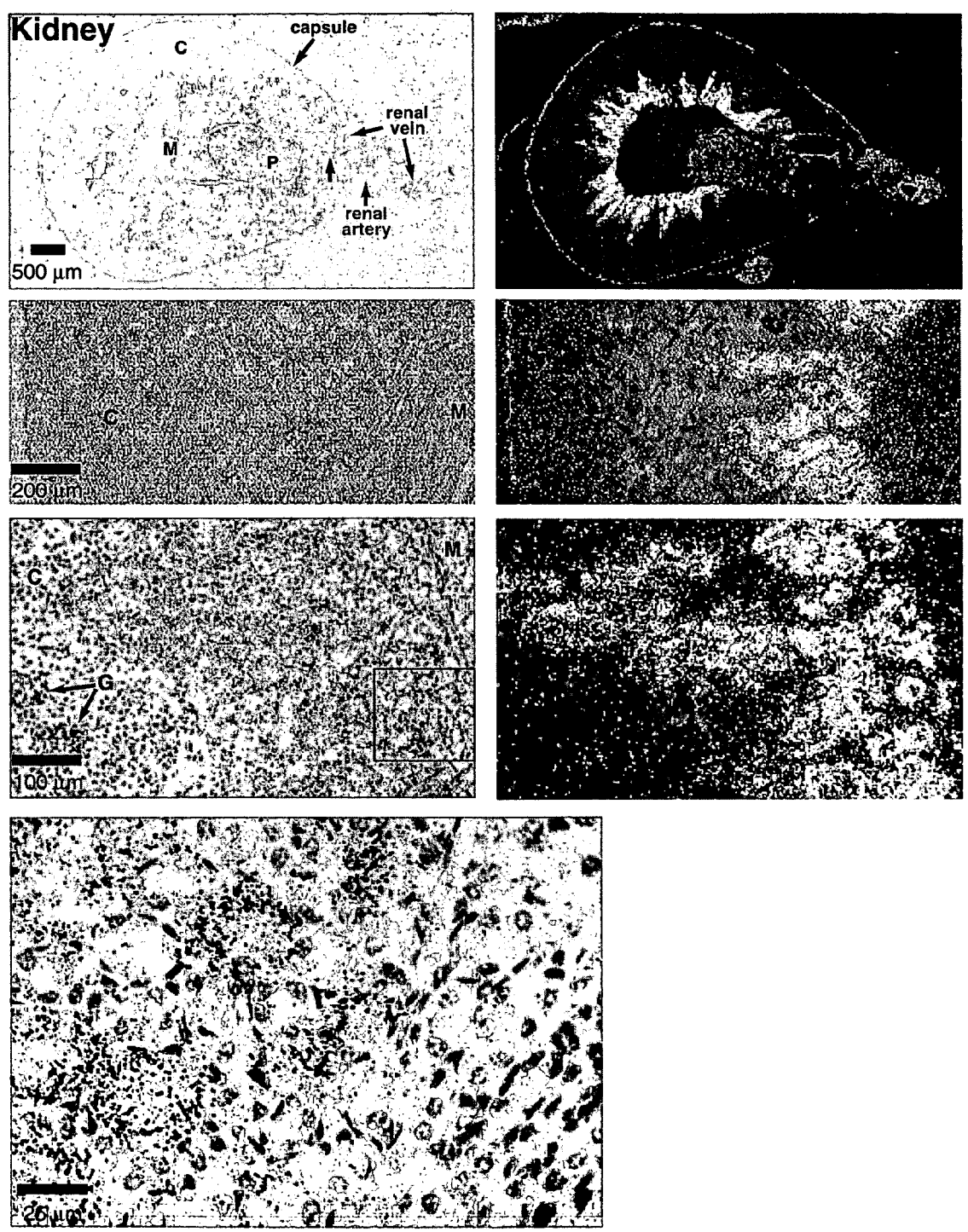
FIG. 11 illustrates the expression of murine CHL mRNA as detected by in situ hybridization in normal adult mouse kidney (boxed area is shown at higher magnification in the lower panel; C=cortex, M=medulla, P=papilla, and G=glomerulus)
Figure 12:
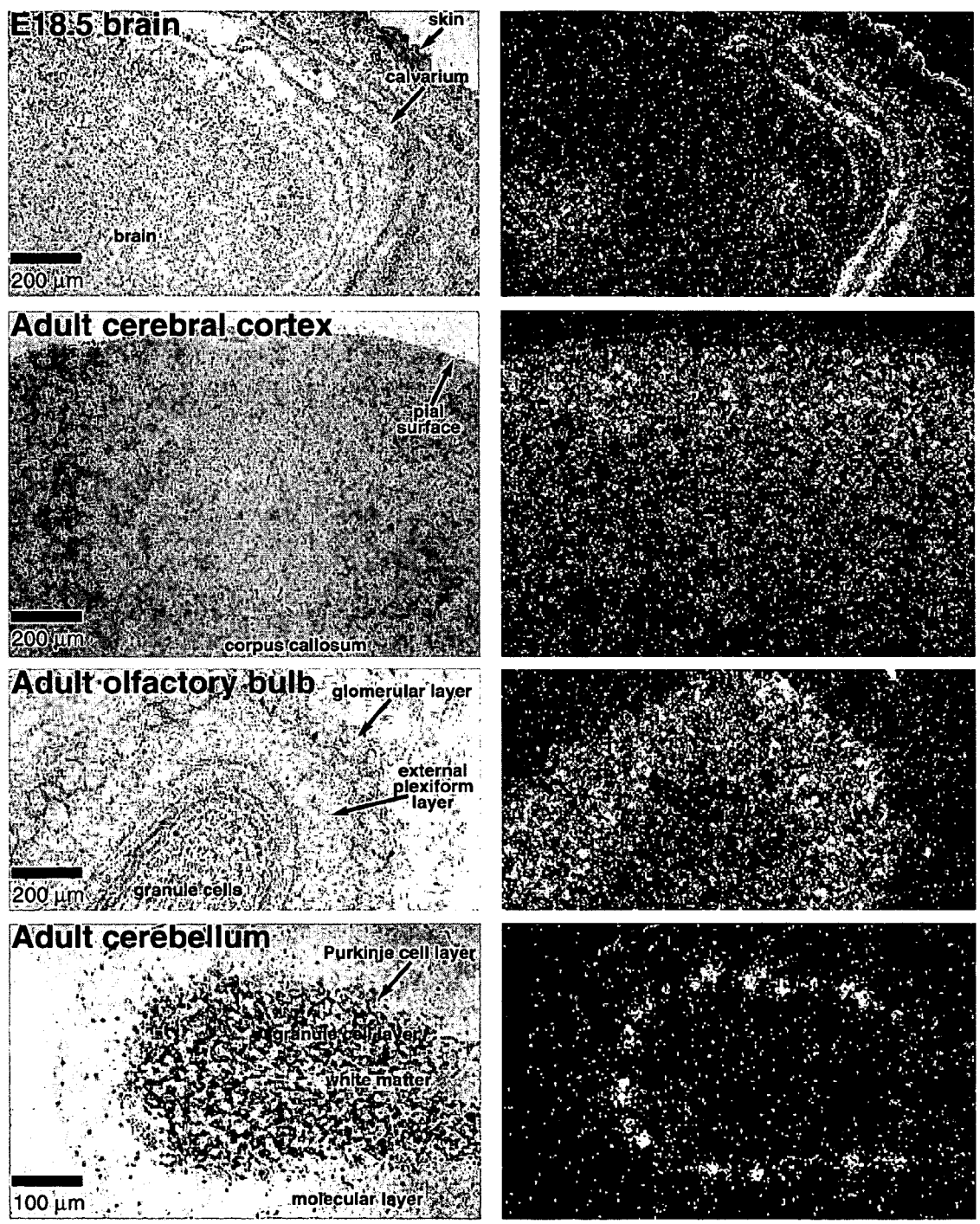
FIG. 12 illustrates the expression of murine CHL mRNA as detected by in situ hybridization in normal embryonic and adult mouse brain.

The expression of CHL mRNA was analyzed in those tissues determined to be CHL-expressing in the Northern blot analysis described above. Populations of fibroblast/connective tissue cells in the female reproductive tract, the gastrointestinal tract (FIG. 10), and the outer medulla of the kidney (FIG. 11) were found to express CHL mRNA. In the brain, CHL transcripts were localized in the cerebral cortex, the external plexiform layer of the olfactory bulb, and Purkinje cells of the cerebellum (FIG. 12). The weak expression of CHL mRNA detected in the lung and liver by Northern analysis, was actually localized to blood vessels supplying these tissues (FIG. 10). Weak expression of CHL mRNA detected in the spleen and lymph nodes was localized to a non-lymphocytic cell population. Interestingly, in situ hybridization revealed additional sites of CHL mRNA expression. These additional sites include skin mesenchyme and white adipose tissue. These observations suggest that, in the adult mouse, CHL mRNA is expressed mainly in cells of mesenchymal origin (with the exception of neuronal cells in the brain).

Figure 13:
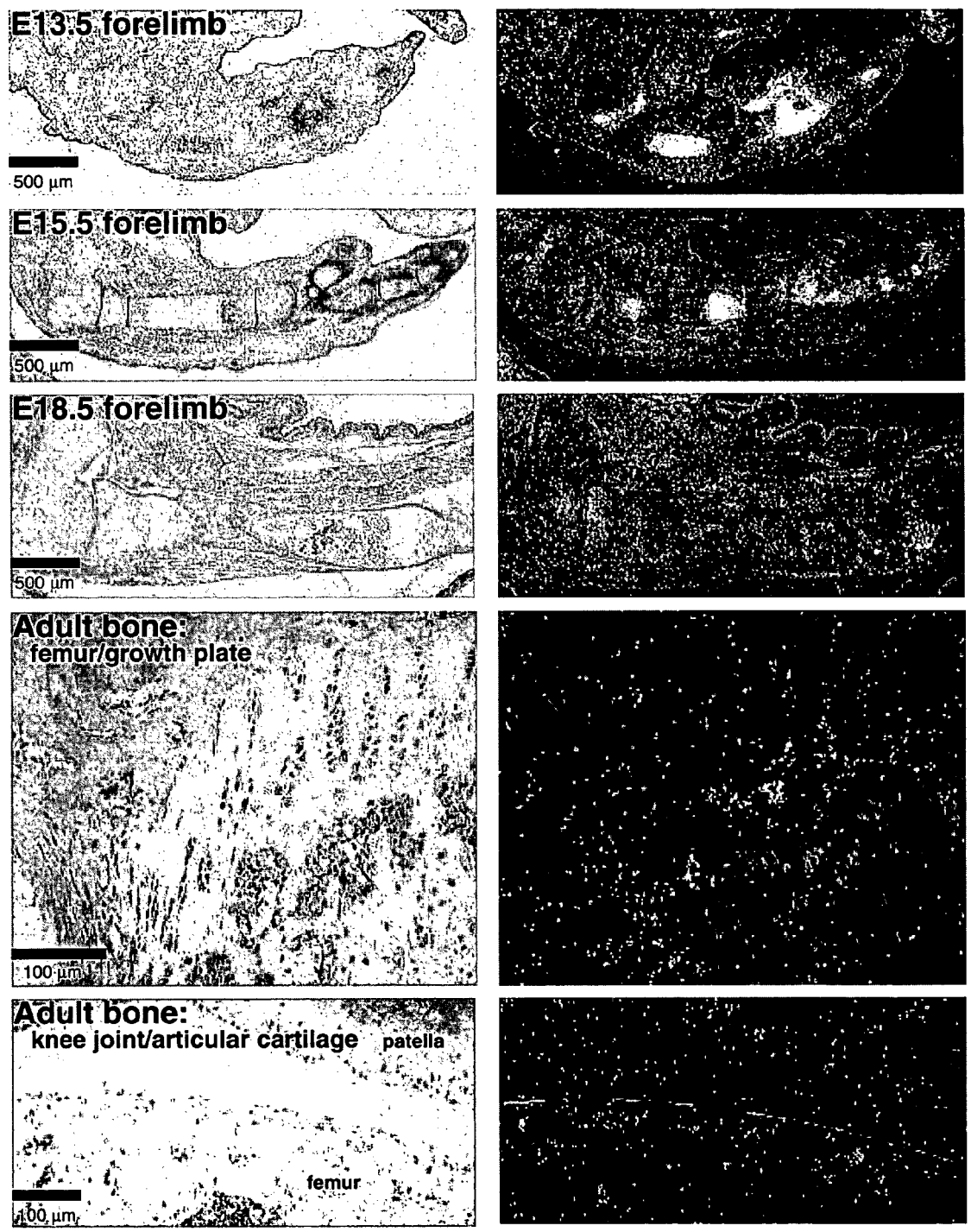
FIG. 13 illustrates the expression of murine CHL mRNA as detected by in situ hybridization in normal embryonic and adult mouse bone.

In day 12.5 mouse embryos, a low level of signal was detected over cephalic mesenchyme in areas where the basiooccipital and exoccipital bones will form, over mesenchymal cells in the lower jaw, and adjacent to the dorsal root ganglia in areas where vertebrae will form. A very low level of signal was also detected over the stomach wall (but not the epithelial lining of the stomach). In day 13.5 embryos, a signal was detected over the cartilage of the ribs, vertebra, limb bone (FIG. 13), and trachea, and possibly over mesenchymal condensations destined to become tendon. In day 14.5 through 18.5 embryos, a detectable signal over the cartilage of the developing bones (FIG. 13) was still present. In bones forming by endochondral formation, the signal appeared to be primarily over the hypertrophic chondrocytes in the growth regions, while the signal was more diffuse and less restricted in, for example, the bones of the head, which develop by intramembranous formation (FIG. 12). Also at these stages, the pattern of expression in the gastrointestinal tract was similar to that of the adult, with a low level of signal being detected in a layer of fibroblast or smooth muscle cells between the mucosa and mucularis. One difference between embryonic and adult CHL mRNA expression concerned the esophagus where a signal was detected in the embryo but not the adult. This difference may have been due to the level of the embryonic sections that were examined.

At several embryonic stages, a signal was detected over relatively undifferentiated mesenchymal/connective tissue-type cells. For example, in day 14.5 embryos, CHL mRNA expression was detected in, and adjacent to, the salivary glands. In addition, CHL mRNA expression was detected in day 18.5 embryos in the subcutaneous tissue.

In summary, the strongest signal detected with the CHL mRNA probe was detected in the developing skeleton of the mouse embryo. Such expression was detected in the cartilage of bones undergoing either intramembranous or endochondral development. In the adult mouse CHL mRNA expression in bone or cartilage (as examined in the growth plate region of long bones, the articular cartilage of the joints, and tracheal cartilage) was either not present or was below the level of sensitivity by in situ analysis. These observations support the argument that CHL mRNA may be an important regulator of bone and cartilage formation.

EXAMPLE 5

Chromosomal Mapping of the Murine CHL Polypeptide Gene

Fluorescence in situ hybridization (FISH) analsis was used to determine the chromosomal localization of the murine CHL gene (Shi et al., 1997, *Genomics* 45:4247). A FISH probe was prepared from a BAC clone isolated from the Mouse ES-129/SvJ II BAC chromosome DNA library (Genome Systems) by PCR using standard techniques and primers corresponding to the second CR domain of the murine CHL gene (5'-T-T-A-C-C-A-C-C-A-G-T-G-A-A-C-A-A-T-A-A-G-G-3'; SEQ ID NO: 26 and 5'-C-T-T-G-A-G-A-C-C-A-C-A-G-T-A-T-A-C-A-T-T-C-C-3'; SEQ ID NO: 27). The isolated BAC clone, F1038, was further examined by PCR using standard techniques and primers covering the 5' untranslated region and signal peptide region of the murine CHL gene (5'-A-G-T-G-C-C-C-A-G-C-T-T-T-A-G-T-C-C-A-C-3'; SEQ ID NO: 28 and 5'-G-T-T-C-T-G-T-T-T-T-G-C-T-T-C-C-T-T-C-T-A-G-3'; SEQ ID NO: 29). From this analysis, it was concluded that the F1038 clone contains at least those exons of the murine CHL gene spanning from the 5' untranslated region to the second CR domain. The murine CHL gene was mapped using F1038 DNA as a probe. It was found to be on the X chromosome.

A partial sequence of the human CHL gene, derived from the q22.1-23 region of the human X chromosome, was found in GenBank (Accession no. AL049176). In order to localize the murine CHL gene on the X chromosome, the X centromere-specific P1 clone (#6856) was also used as a co-hybridization probe (Shi et al., 1997, *Genomics* 45:4247). A total of 80 metaphase cells were analyzed with 72 exhibiting specific labeling. Of these, 10 were used for co-hybridization experiments. The murine CHL gene was located at a position, which was 89% of the distance from the heterochromatic-euchromatic boundary to the telomere of the X chromosome, an area corresponding to band XF3. Therefore, it has been concluded that both human and murine CHL genes are located on a similar region of the X chromosome.

EXAMPLE 6

Production of CHL Polypeptides

A. Expression of CHL Polypeptides in Bacteria

PCR is used to amplify template DNA sequences encoding a CHL polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary vector, such as pAMG21 (ATCC no. 98113) containing the lux promoter and a gene encoding kanamycin resistance is digested with Bam HI and Nde I for directional cloning of inserted DNA. The ligated mixture is transformed into an *E. coli* host strain by electroporation and transformants are selected for kanamycin resistance. Plasmid DNA from selected colonies is isolated and subjected to DNA sequencing to confirm the presence of the insert.

Transformed host cells are incubated in 2xYT medium containing 30 □g/mL kanamycin at 30° C. prior to induction. Gene expression is induced by the addition of N-(3-oxohexanoyl)-dl-homoserine lactone to a final concentration of 30 ng/mL followed by incubation at either 30° C. or 37° C. for six hours. The expression of CHL polypeptide is evaluated by centrifugation of the culture, resuspension and lysis of the bacterial pellets, and analysis of host cell proteins by SDS-polyacrylamide gel electrophoresis.

Inclusion bodies containing CHL polypeptide are purified as follows. Bacterial cells are pelleted by centrifugation and resuspended in water. The cell suspension is lysed by sonication and pelleted by centrifugation at 195,000×g for 5 to 10 minutes. The supernatant is discarded, and the pellet is washed and transferred to a homogenizer. The pellet is homogenized in 5 mL of a Percoll solution (75% liquid Percoll and 0.15 M NaCl) until uniformly suspended and then diluted and centrifuged at 21,600×g for 30 minutes. Gradient fractions containing the inclusion bodies are recovered and pooled. The isolated inclusion bodies are analyzed by SDS-PAGE.

A single band on an SDS polyacrylamide gel corresponding to *E. coli*-produced CHL polypeptide is excised from the gel, and the N-terminal amino acid sequence is determined essentially as described by Matsudaira et al., 1987, *J. Biol. Chem.* 262:10-35.

B. Construction of CHL Polypeptide Mammalian Expression Vectors

A FLAG-tagged murine CHL polypeptide expression construct was prepared as follows. A full-length murine CHL DNA fragment, in which the stop codon was replaced by a BamHI site, was obtained by PCR using the full-length murine cDNA clone as a template and the primers 2149-76 (5'-G-C-T-A-G-C-G-G-C-C-G-C-G-C-C-A-C-C-A-T-G-G-A-T-G-G-C-A-T-G-A-A-A-T-A-C-A-T-C-A-T-T-T-C-3'; SEQ ID NO: 30) and 2149-77 (5'-G-G-T-A-C-C-G-G-A-T-C-C-A-C-C-A-A-A-G-G-C-A-G-G-G-C-C-T-C-C-A-G-C-3'; SEQ ID NO: 31).

The amplified PCR product was digested with Not I and Bam HI, gel purified, and then inserted into the pFLAG-CMV-5a expression vector (Sigma) with the FLAG-sequence attached in-frame with the CHL sequence at its carboxyl-terminus. The fusion site between the CHL and FLAG sequences was subsequently confirmed by sequencing. The resulting CHL-FLAG expression plasmid is designated as pFLAGmCHL.

A FLAG-tagged murine CHD construct was prepared as follows. Murine CHD cDNA was isolated by RT-PCR from a mouse E7 embryo cDNA library (Clontech) using the primers 2170-06 (5'-G-C-T-A-G-C-G-G-C-C-G-C-G-C-C-A-C-C-A-T-G-C-C-G-A-G-C-C-T-C-C-C-G-G-C-C-C-C-G-3'; SEQ ID NO: 32) and 2170-07 (5'-G-G-G-A-T-C-C-G-T-C-G-A-C-G-G-A-G-T-G-C-T-C-C-G-C-T-T-C-T-T-T-C-T-C-C-A-G-3'; SEQ ID NO: 33).

The amplified PCR product was digested with Not I and Sal I, gel purified, and then inserted into the pFLAG-CMV-5a expression vector. Eleven clones were isolated and the corresponding cDNA inserts sequenced. To generate the final CHD-FLAG expression construct (labeled pFLAGmCHD), a 1.9 kb Eco RI-Bgl II fragment of one of the identified clones (clone #16) was replaced with the corresponding 1.9 kb fragment of a separate clone (clone #3) to remove errors in the sequence introduced as a result of PCR amplification.

To analyze the expression of either CHL-FLAG or CHD-FLAG, the pFLAGmCHL and pFLAGmCHD expression constructs were first introduced into human 293T cells using SuperFect transfection reagent (Qiagen), according to the manufacturer's suggested protocols. Prior to, and immediately following transfection, the 293T cells were maintained in DMEM supplemented with 10% Fetal Calf Serum (FCS, Hyclone). Following transfection, the cells were incubated overnight at 37° C. and 5% $CO_2$, and then the culture medium was renewed with serum-free IMDM, supplemented with 5-15% Knockout SR (Gibco BRL), and the cells were incubated for an additional 48 hours. The conditioned medium was then removed and CHL-FLAG and CHD-FLAG protein expression was analyzed by Western blot analysis using the anti-FLAG antibody M2 (Sigma). Approximately, 1 μg/mL of the CHD-FLAG and CHL-FLAG proteins were obtained.

Figure 14A:
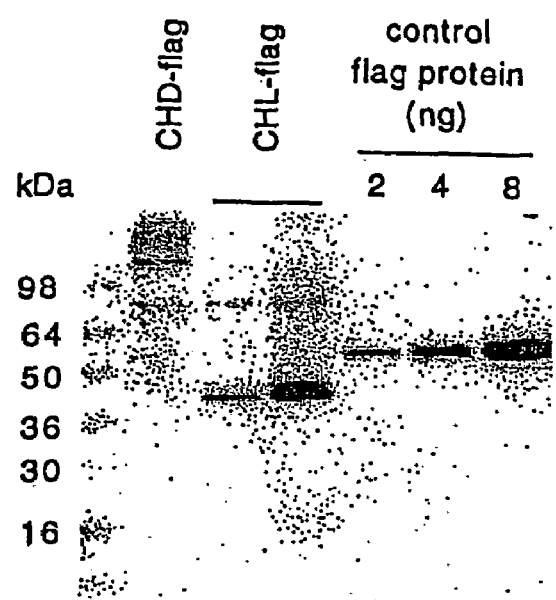
FIGS. 14A-14C illustrate Western blot analysis of CHL-FLAG polypeptides.

To generate clones capable of stably expressing CHL-FLAG or CHD-FLAG, 293 cells were transfected using the calcium phosphate method with either linearized pFLAGm-CHL or pFLAGmCHD and pGKneo (in a ratio of 30 to 1). After incubating the cells for 36 to 48 hours at 37° C., the transfected cells were renewed with fresh medium containing 800 μg/mL G418 (Gibco BRL) for 12 days, and 12 clones were isolated for each transfection reaction. The expression levels of the CHL-FLAG and CHD-FLAG proteins were determined by Western blot analysis using the anti-FLAG M2 antibody. The clones with the highest expression levels (about 0.1 μg of CHL-FLAG or CHD-FLAG/mL of cell supernatant) were selected and expanded (FIG. 14A).

CHL-FLAG and CHD-FLAG proteins were partially purified from the selected clones as follows. Clones expressing the proteins were expanded by growing the cells as suspension cells in a spinner culture with 293 SFM (Gibco BRL). Conditioned medium was collected and cell debris removed by centrifugation. CHL-FLAG and CHD-FLAG proteins were isolated by affinity chromatography using anti-FLAG M2 affinity gel (Sigma) packed in poly-prep chromatography columns (Bio-Rad). The bound fraction, containing the FLAG-tagged CHL polypeptide or CHD protein was eluted by adding 100 μg/mL FLAG peptide (Sigma).

Figure 14B:
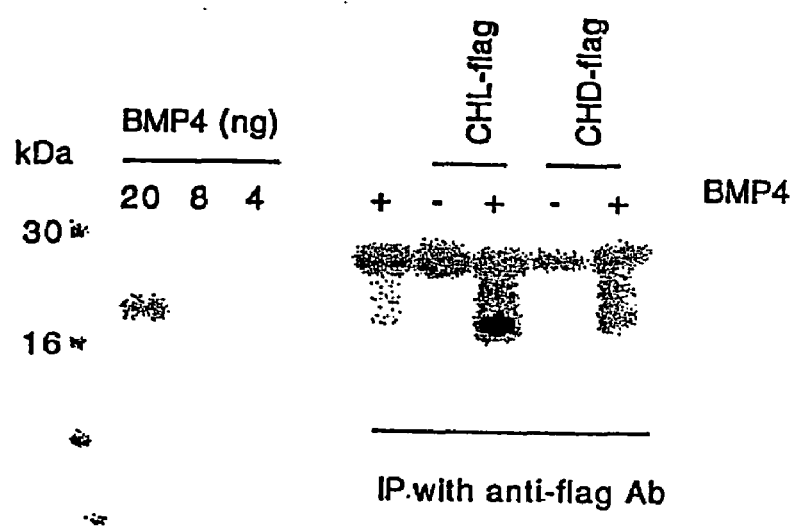
Figure 14C:
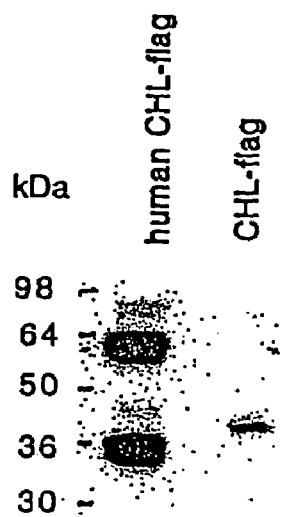

The human CHL-FLAG protein was also constructed in a similar way. A full-length human CHL DNA fragment in which the stop codon was replaced by a Bam HI site was obtained by PCR using the full-length human CHL cDNA clone as a template and the primers 2235-53 and 2235-54. The amplified PCR product was digested with Eco RI and Bam HI, gel purified, and then inserted into the pFLAG-CMV5a expression vector (Sigma). The resulting CHL-FLAG expression plasmid is designated as pFLAGhCHL. The pFLAGh-CHL plasmid was introduced into human 293T cells as described, conditioned medium was removed, and the human CHL-FLAG expression was analyzed by Western blot analysis with anti-FLAG antibody M2 (Sigma) (FIG. 14C).

C. Expression and Purification of CHL Polypeptide in Mammalian Cells

CHL polypeptide expression constructs are introduced into 293 EBNA or CHO cells using either a lipofection or calcium phosphate protocol.

To conduct functional studies on the CHL polypeptides that are produced, large quantities of conditioned media are generated from a pool of hygromycin selected 293 EBNA clones. The cells are cultured in 500 cm Nunc Triple Flasks to 80% confluence before switching to serum free media a week prior to harvesting the media. Conditioned media is harvested and frozen at −20° C. until purification.

Conditioned media is purified by affinity chromatography as described below. The media is thawed and then passed through a 0.2 μm filter. A Protein G column is equilibrated with PBS at pH 7.0, and then loaded with the filtered media. The column is washed with PBS until the absorbance at $A_{280}$ reaches a baseline. CHL polypeptide is eluted from the column with 0.1 M Glycine-HCl at pH 2.7 and immediately neutralized with 1 M Tris-HCl at pH 8.5. Fractions containing CHL polypeptide are pooled, dialyzed in PBS, and stored at −70° C.

For Factor Xa cleavage of the human CHL polypeptide-Fc fusion polypeptide, affinity chromatography-purified protein is dialyzed in 50 mM Tris-HCl, 100 mM NaCl, 2 mM $CaCl_2$ at pH 8.0. The restriction protease Factor Xa is added to the dialyzed protein at 1/100 (w/w) and the sample is digested overnight at room temperature.

EXAMPLE 7

The N-terminal Amino Acid Sequence Determination of the Mature CHL-FLAG and CHD-FLAG Proteins The affinity purified murine CHL-FLAG and murine CHD-FLAG proteins were separated from contaminated proteins by the SDS-polyacrylamide gel electrophoresis, and the major band was excised for amino acid sequence determination with the gas-phase peptide sequencer, Procise 494 (Applied Biosystems). The results have indicated that the murine CHL-FLAG polypeptide precursor (SEQ ID NO: 34) is cleaved between $Thr^{22}$ and $Glu^{23}$, and that the murine CHD-FLAG protein precursor (SEQ ID NO: 36) is cleaved between $Gly^{26}$ and $Thr^{27}$ to generate the mature forms of murine CHL-FLAG polypeptide (SEQ ID NO: 35) and CHD-FLAG protein (SEQ ID NO: 37).

EXAMPLE 8

Production of Anti-CHL Polypeptide Antibodies

Antibodies to CHL polypeptides may be obtained by immunization with purified protein or with CHL peptides produced by biological or chemical synthesis. Suitable procedures for generating antibodies include those described in Hudson and Bay, *Practical Immunology* (2nd ed., Blackwell Scientific Publications).

In one procedure for the production of antibodies, animals (typically mice or rabbits) are injected with a CHL antigen (such as a CHL polypeptide), and those with sufficient serum titer levels as determined by ELISA are selected for hybridoma production. Spleens of immunized animals are collected and prepared as single cell suspensions from which splenocytes are recovered. The splenocytes are fused to mouse myeloma cells (such as Sp2/0-Ag14 cells), are first incubated in DMEM with 200 U/mL penicillin, 200 □g/mL streptomycin sulfate, and 4 mM glutamine, and are then incubated in HAT selection medium (hypoxanthine, aminopterin, and thymidine). After selection, the tissue culture supernatants are taken from each fusion well and tested for anti-CHL antibody production by ELISA.

Alternative procedures for obtaining anti-CHL antibodies may also be employed, such as the immunization of transgenic mice harboring human Ig loci for production of human antibodies, and the screening of synthetic antibody libraries, such as those generated by mutagenesis of an antibody variable domain.

EXAMPLE 9

Biological Activity of Murine CHL in *Xenopus* Embryos

To assay the biological effect of native murine CHL polypeptide in *Xenopus* embryos, a vector carrying the full-length murine CHL cDNA (pcDNA3mCHL), was used for in vitro RNA synthesis. The vector was first linearized with Not I and the capped mRNA was then transcribed with T7 RNA polymerase, using the mMESSAGE mMACHINE T7 kit (Ambion). For mCHL-FLAG, the Eco RI-Sca I fragment of FLAG-tagged CHL polypeptide was first cloned into the Eco RI-Not I site of RN3 (Lemaire et al., 1995, Cell 81:85-94), and then linearized with Sfi I. Then, capped mRNA was transcribed with T3 RNA polymerase. Following either synthesis, recovered RNA was subjected to two rounds of ethanol precipitation with 0.5 M ammonium acetate to remove unincorporated nucleotides, and then quantified by spectrophotometry at 260 nm.

Figure 15A:
FIGS. 15A-15B illustrate the secondary axis-forming activity of murine CHL polypeptide.
Figure 15B:

*Xenopus* embryos were dejellied in 3% cysteine and staged as described in Nieuwkoop and Faber, *Normal Table of Xenopus laevis* (Daudin, ed., Garland Publishing, 1994). Embryos were placed into Steinberg's solution containing 5% Ficoll and 5 nL of RNA was injected into the two ventral blastomeres of 4-cell stage embryos. Following injection with various amounts of RNA, embryos were cultured in 10% Steinberg's solution for 48 hours, and the embryos scored for ectopic axis. Of the embryos injected with 100 pg of either murine CHL-FLAG or native murine CHL RNA, all showed hyperdorsalization phenotypes, in which the anterior portions of the embryos are enlarged and the posterior parts are missing. This result is often observed when an excess amount of RNA carrying axis duplication activity has been injected into the embryo. The injection of 30 pg RNA/embryo was found to be the optimal amount for generating an axis duplication as a result of the introduction of the CHL polypeptide constructs (FIGS. 15A-15B). An axis duplication rate for CHL polypeptide of 86.7% (26/30 embryos) was observed whereas the rate for uninjected control embryos was 0% (0/31 embryos). The axis duplication rate for CHL-FLAG with poly-A was 78.9% (15/19 embryos), which is similar to that of the native CHL polypeptide without the FLAG-peptide and poly-A. As a positive control, experiments were also performed using the cloned murine CHD-FLAG (lacking poly-A). An axis duplication rate of 82.6% (19/23 embryos) was obtained using 1 ng of RNA. CHL polypeptide, with or without a FLAG-tag, is active in antagonizing the endogenous ventralizing factor (presumably, BMP4) in a similar fashion as CHD.

EXAMPLE 10

Biological Activity of Murine CHL Polypeptide in ES Cells

The ability of CHL polypeptide to inhibit the activity of BMP4 was assayed in mouse embryonic stem (ES) cell culture as follows. E14 ES cells were maintained and differentiated as described by Nakayama et al., 1998, *Blood* 91: 2283-95, with the exception that 0.9% methylcellulose (Stem Cell Technology) was added to the differentiation medium. Serum-free differentiation was achieved by replacing the FCS with Knockout-SR (Gibco BRL), at a concentration of 15%, at the pre-culture stage. The initial cell concentration was between 2500 and 4500 cells/ml. Rat SCF was added at 100 ng/ml to all of the differentiation cultures. Differentiated cells, aggregated as embryoid bodies, were collected, resuspended in 0.25% collagenase mix (a 1:1 mixture of Collagenase D (Boehringer Mannheim) and Collagenase XI (Sigma)) and 15% FCS in PBS, and then incubated for 60 minutes at 37° C. A single cell suspension was then obtained by passing the cells through a 21-gauge needle followed by filtration through a 40-□ mesh. The cells were spun, resuspended in 0.5% BSA in PBSA at $5 \times 10^6$ cells/ml, and then stained with 2-20 µg/mL of antibodies against the hematopoietic cell markers CD34, Ter119, and CD45 (Pharmingen). The stained samples were analyzed on a FACScan (Becton Dickinson). Both Ter119+ erythroid cell formation and CD45+ macrophage cell generation were dependent on the addition of between 0.5 to 2 ng/ml of human BMP4 protein (R&D Systems).

Figure 16:
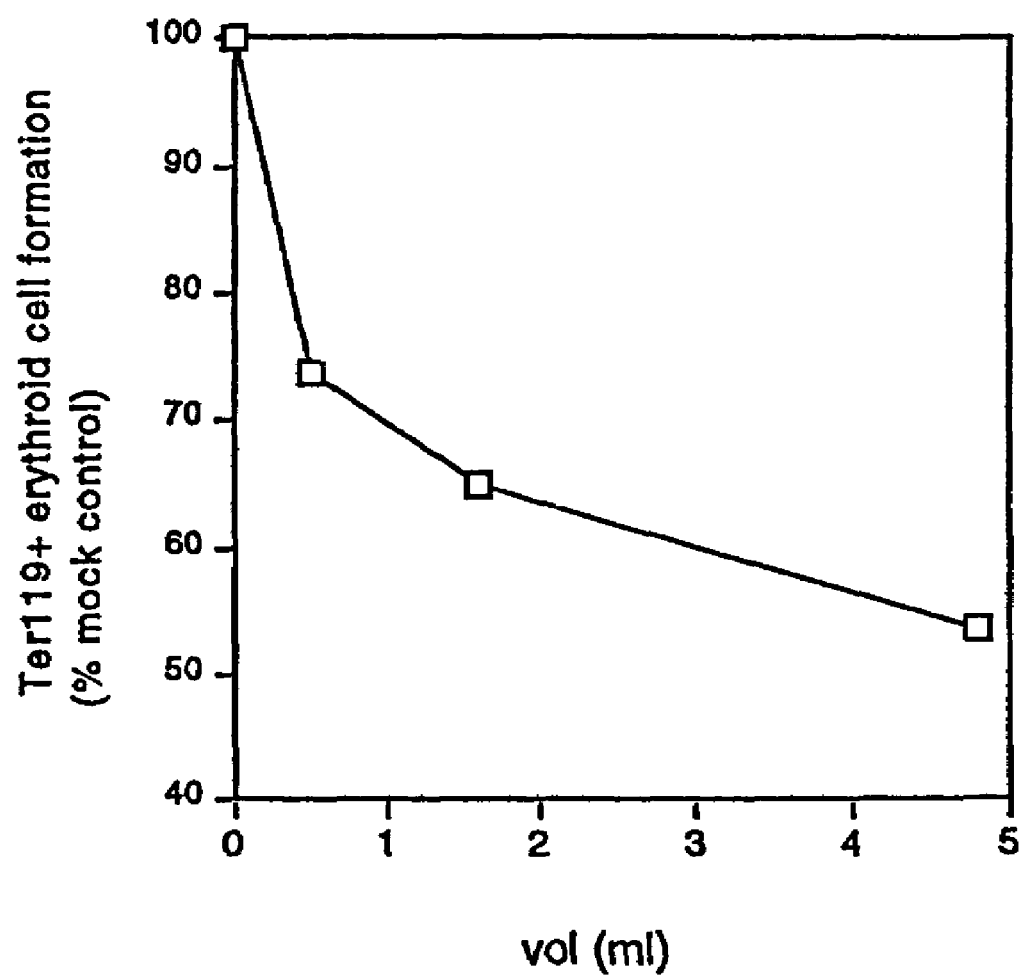
FIG. 16 illustrates the inhibition of Ter119+ erythroid cell generation from ES cells in vitro by the murine CHL-FLAG polypeptide.

To assay the activity of the murine CHL-FLAG protein, a BMP4 concentration of 0.5 ng/mL was utilized, resulting in approximately a half-maximal level of Ter119+erythroid cell formation during 7 days of differentiation. The CHL-FLAG protein made by the transient transfection of 293T cells was added at 0.2 to 2 mL/assay, corresponding to approximately 10 to 100 ng/mL of the CHL-FLAG protein/assay. Decreased levels of CD45+ and Ter119+ cells were detected depending upon the amount of CHL-FLAG protein that was added. For example, the percentage of Ter119+ cells was reduced by 35-50% when 50 to 100 ng/mL of CHL-FLAG protein was added (FIG. 16). This suggests that CHL-FLAG protein is active, perhaps directly, in inhibiting BMP4 activity.

EXAMPLE 11

Direct Interaction of CHL Polypeptide and BMP4

The direct interaction of *Xenopus* CHD protein with human BMP4 protein has been previously demonstrated (Piccolo et al., 1996, *Cell* 86: 589-98). Similar experiments were performed using murine CHL polypeptide. An anti-FLAG antibody M2-conjugated agarose gel (Sigma), recognizing the carboxyl-terminus of the CHL-FLAG and CHD-FLAG fusion proteins was used to immunoprecipitate the CHL-BMP4 complex. Bound BMP4 protein was quantified by Western blot analysis using an anti-BMP2/4 goat polyclonal antibody (Santa Cruz).

Prior to immunoprecipitation, partially purified CHL-FLAG or CHD-FLAG and BMP4 were incubated in TBS (50 mM Tris HC mM NaCl, pH 7.4) for 1 hour at 4° C. Following incubation of the proteins, anti-FLAG M2 affinity gel was added and the reaction incubated for an additional 2 hours at 4° C. in an Eppendorf mixer. After which, the agarose gels were spun down for 3 minutes and washed twice in 1 ml PBS. Following addition of gel loading buffer, the reactions were boiled for 10 minutes, electrophoresed through SDS-polyacrylamide gels under reducing conditions, and then electroblotted onto nitrocellulose membranes.

The filter was subsequently blocked with TBST (10 mM Tris-HCl pH7.5, 0.9% NaCl, 0.1% Tween-20) containing 3% BSA and incubated in the same buffer with a 300-fold dilution of the anti-BMP2/4 antibody for 2 hours at room temperature. The blot was visualized using peroxidase-conjugated anti-goat secondary antibody (Pierce) and the chemiluminescent ECL kit (Amersham). The co-immunoprecipitation of BMP4 protein with either CHL-FLAG or CHD-FLAG suggested that there was a direct physical interaction between CHL polypeptide, or CHD, and BMP4 (FIG. 14B).

EXAMPLE 12

BMP4—Dependent Cell Proliferation and Survival

Figure 17:
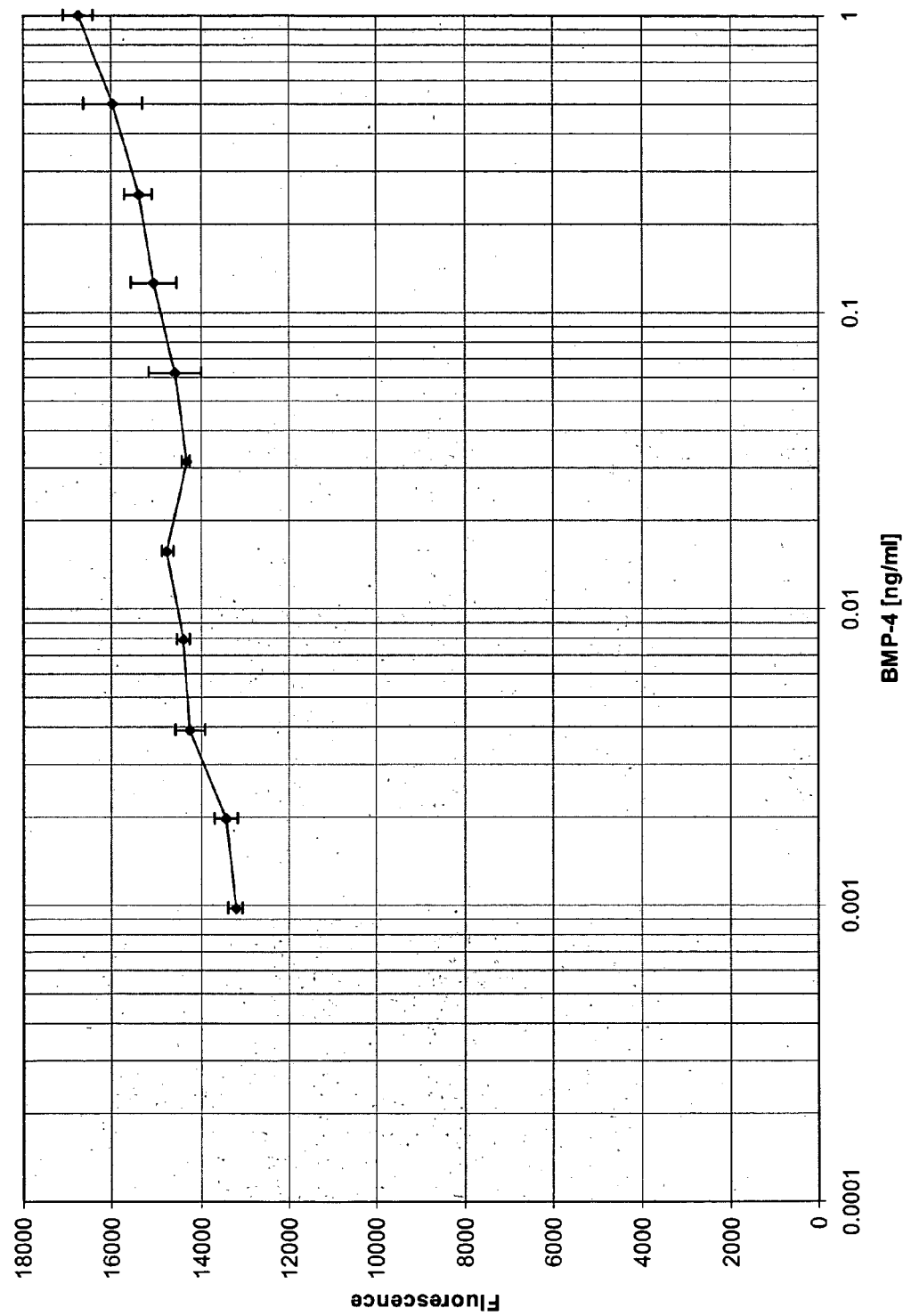
FIG. 17 illustrates the results of a BMP-4-dependent cell proliferation and survival assay in which A5-F stromal cells were incubated with different concentrations pf BMP-4 protein.
Figure 18:
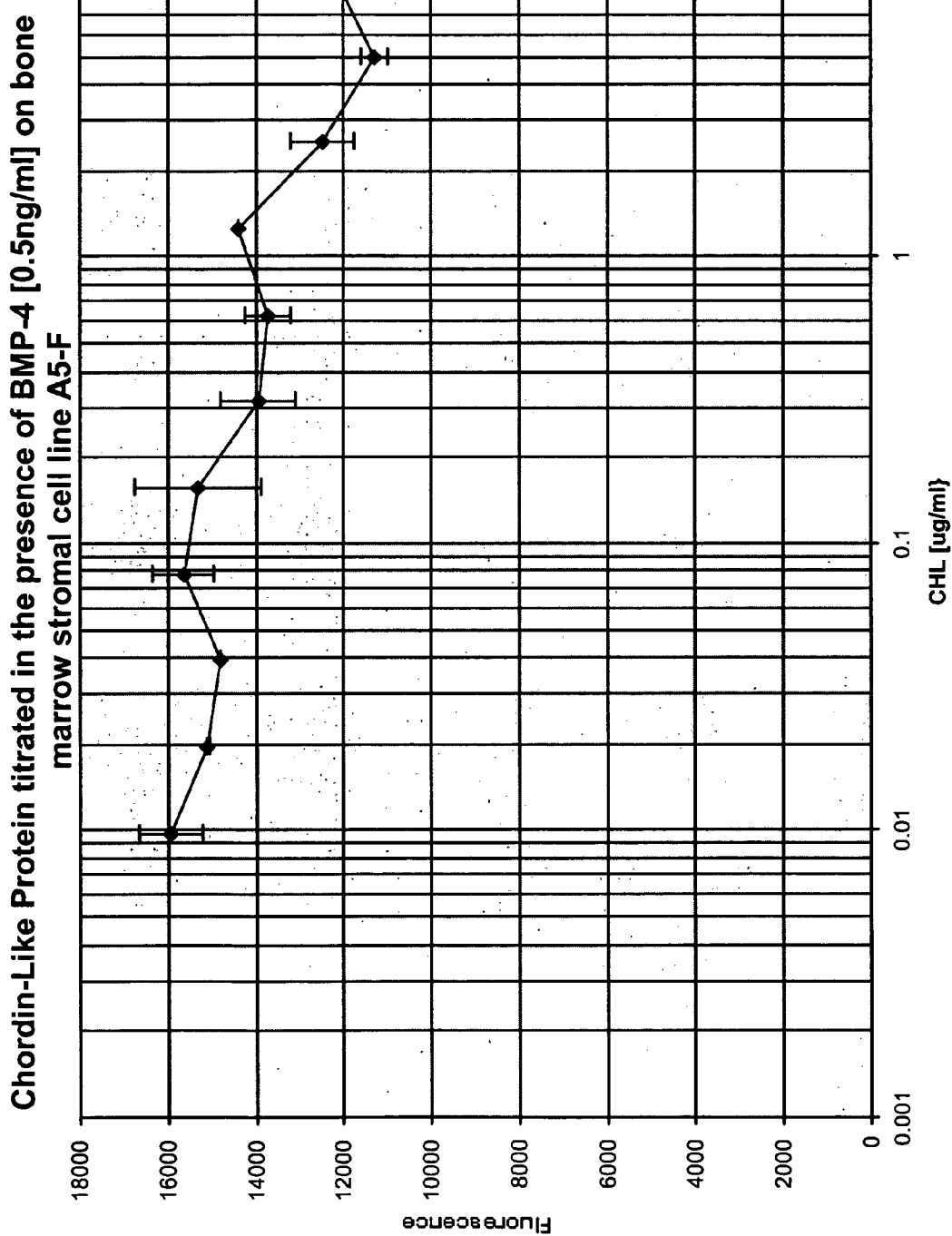
FIG. 18 illustrates the results of a BMP4-dependent cell proliferation and survival assay in which A5-F stromal cells were incubated with a constant concentration of BMP-4 protein and different cocentrations of CHL polypeptide.

To analyze CHL polypeptide-mediated inhibition of BMP4-dependent proliferation and survival in A5-F stromal cells, 100 µl of test sample diluted in Iscove's modified Dulbecco medium (IMDM), 40 µl of 5× serum-free media containing bovine insulin (500 µg/ml), and 2000 A5-F murine bone marrow stromal cells (in a volume of 60 µl in IMDM) were added to each well in a 96-well mouse Collagen IV coated plate (Becton Dickinson). The culture was then incubated for 72 hours at 37° C. and 5% $CO_2$. Following incubation, 22 µl of Alamar Blue Cell Proliferation Indicator (Biosource) was added to each well and the culture was incubated for an additional 24 hours. Following this incubation, the wells were read on a fluorescence microplate reader (BioTech Instruments FL500; using the following settings: excitation at 530/25 nm; emission at 590/35 nm; and sensitivity at 36). In this assay, Alamar Blue Cell Proliferation Indicator serves as a fluorometric growth indicator or detector of metabolic activity. Specifically, Alamar Blue Cell Proliferation Indicator acts as an oxidation-reduction indicator that fluoresces in response to the chemical reduction of growth medium resulting from cell growth. In the presence of continued cell growth, a reduced environment is maintained in the culture medium, while in the presence of inhibited cell growth, an oxidized environment is maintained. Reduction related to cell growth causes the redox indicator to change from an oxidized form (i.e., non-fluorescent, blue) to a reduced form (i.e., fluorescent, red). FIGS. 17-18 illustrate the results of BMP4 dependent cell proliferation and survival assays following incubation of A5-F cells in BMP-4 protein (FIG. 17) or CHL polypeptide (FIG. 18).

EXAMPLE 13

Expression of CHL Polypeptide in Transgenic Mice

To assess the biological activity of CHL polypeptide, a construct encoding a CHL polypeptide/Fc fusion protein under the control of a liver specific ApoE promoter is prepared. The delivery of this construct is expected to cause pathological changes that are informative as to the function of CHL polypeptide. Similarly, a construct containing the full-length CHL polypeptide under the control of the beta actin promoter is prepared. The delivery of this construct is expected to result in ubiquitous expression.

To generate these constructs, PCR is used to amplify template DNA sequences encoding a CHL polypeptide using primers that correspond to the 5' and 3' ends of the desired sequence and which incorporate restriction enzyme sites to permit insertion of the amplified product into an expression vector. Following amplification, PCR products are gel purified, digested with the appropriate restriction enzymes, and ligated into an expression vector using standard recombinant DNA techniques. For example, amplified CHL polypeptide sequences can be cloned into an expression vector under the control of the human β-actin promoter as described by Graham et al., 1997, *Nature Genetics,* 17:272-74 and Ray et al., 1991, *Genes Dev.* 5:2265-73.

Following ligation, reaction mixtures are used to transform an *E. coli* host strain by electroporation and transformants are selected for drug resistance. Plasmid DNA from selected colonies is isolated and subjected to DNA sequencing to confirm the presence of an appropriate insert and absence of mutation. The CHL polypeptide expression vector is purified through two rounds of CsCl density gradient centrifugation, cleaved with a suitable restriction enzyme, and the linearized fragment containing the CHL polypeptide transgene is purified by gel electrophoresis. The purified fragment is resuspended in 5 mM Tris, pH 7.4, and 0.2 mM EDTA at a concentration of 2 mg/ML.

Single-cell embryos from BDF1×BDF1 bred mice are injected as described (PCT Pub. No. WO 97/23614). Embryos are cultured overnight in a $CO_2$ incubator and 15-20 two-cell embryos are transferred to the oviducts of a pseudopregnant CD1 female mice. Offspring obtained from the implantation of microinjected embryos are screened by PCR amplification of the integrated transgene in genomic DNA samples as follows. Ear pieces are digested in 20 mL ear buffer (20 mM Tris, pH 8.0, 10 mM EDTA, 0.5% SDS, and 500 mg/mL proteinase K) at 55° C. overnight. The sample is then diluted with 200 mL of TE, and 2 mL of the ear sample is used in a PCR reaction using appropriate primers.

At 8 weeks of age, transgenic founder animals and control animals are sacrificed for necropsy and pathological analysis. Portions of spleen are removed and total cellular RNA isolated from the spleens using the Total RNA Extraction Kit (Qiagen) and transgene expression determined by RT-PCR. RNA recovered from spleens is converted to cDNA using the SuperScrip™ Preamplification System (Gibco-BRL) as follows. A suitable primer, located in the expression vector sequence and 3' to the CHL polypeptide transgene, is used to prime cDNA synthesis from the transgene transcripts. Ten mg of total spleen RNA from transgenic founders and controls is incubated with 1 mM of primer for 10 minutes at 70° C. and placed on ice. The reaction is then supplemented with 10 mM Tris-HCl, pH 8.3, 50 mM KCl, 2.5 mM $MgCl_2$, 10 mM of each dNTP, 0.1 mM DTT, and 200 U of SuperScript II reverse transcriptase. Following incubation for 50 minutes at 42° C., the reaction is stopped by heating for 15 minutes at 72° C. and digested with 2 U of RNase H for 20 minutes at 37° C. Samples are then amplified by PCR using primers specific for CHL polypeptide.

EXAMPLE 14

Biological Activity of CHL Polypeptide in Transgenic Mice

Prior to euthanasia, transgenic animals are weighed, anesthetized by isofluorane and blood drawn by cardiac puncture. The samples are subjected to hematology and serum chemistry analysis. Radiography is performed after terminal exsanguination. Upon gross dissection, major visceral organs are subject to weight analysis.

Following gross dissection, tissues (i.e., liver, spleen, pancreas, stomach, the entire gastrointestinal tract, kidney, reproductive organs, skin and mammary glands, bone, brain, heart, lung, thymus, trachea, esophagus, thyroid, adrenals, urinary bladder, lymph nodes and skeletal muscle) are removed and fixed in 10% buffered Zn-Formalin for histological examination. After fixation, the tissues are processed into paraffin blocks, and 3 mm sections are obtained. All sections are stained with hematoxylin and exosin, and are then subjected to histological analysis.

The spleen, lymph node, and Peyer's patches of both the transgenic and the control mice are subjected to immunohistology analysis with B cell and T cell specific antibodies as follows. The formalin fixed paraffin embedded sections are deparaffinized and hydrated in deionized water. The sections are quenched with 3% hydrogen peroxide, blocked with Protein Block (Lipshaw, Pittsburgh, Pa.), and incubated in rat monoclonal anti-mouse B220 and CD3 (Harlan, Indianapolis, Ind.). Antibody binding is detected by biotinylated rabbit anti-rat immunoglobulins and peroxidase conjugated streptavidin (BioGenex, San Ramon, Calif.) with DAB as a chromagen (BioTek, Santa Barbara, Calif.). Sections are counterstained with hematoxylin.

After necropsy, MLN and sections of spleen and thymus from transgenic animals and control littermates are removed. Single cell suspensions are prepared by gently grinding the tissues with the flat end of a syringe against the bottom of a 100 mm nylon cell strainer (Becton Dickinson, Franklin Lakes, N.J.). Cells are washed twice, counted, and approximately $1 \times 10^6$ cells from each tissue are then incubated for 10 minutes with 0.5 □g CD16/32(FcγIII/II) Fc block in a 20 □L volume. Samples are then stained for 30 minutes at 2-8° C. in a 100 □L volume of PBS (lacking $Ca^+$ and $Mg^+$), 0.1% bovine serum albumin, and 0.01% sodium azide with 0.5 □g antibody of FITC or PE-conjugated monoclonal antibodies against CD90.2 (Thy-1.2), CD45R (B220), CD11b(Mac-1), Gr-1, CD4, or CD8 (PharMingen, San Diego, Calif.). Following antibody binding, the cells are washed and then analyzed by flow cytometry on a FACScan (Becton Dickinson).

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. An isolated polynucleotide, selected from:
   (a) a polynucleotide comprising nucleotides 1-1341 of SEQ ID NO:11;
   (b) a polynucleotide that encodes a polypeptide comprising amino acids 1-447 of SEQ ID NO:12; and
   (c) a nucleotide sequence complementary to the full-length sequence of (a) or (b).

2. An isolated polynuoleotide, comprising nucleotides 1-1341 of SEQ ID NO:11.

3. An isolated polynucleotide, comprising a polynucleotide that encodes a polypeptide comprising amino acids 1-447 of SEQ ID NO:12.

4. An isolated polynucleotide, selected from:
   (a) a polynucleotide comprising nucleotides 1-1341 of SEQ ID NO:11;
   (b) a polynucleotide that encodes a polypeptide comprising amino acids 1-447 of SEQ ID NO:12; and
   (c) a nucleotide sequence complementary to the full-length sequence of (a) or (b),
   wherein the polynucleotide encodes a polypeptide having a carboxy-terminus truncation, and wherein the encoded truncated polypeptide retains the capacity to bind a bone morphogenetic protein-4.

5. A vector, comprising the nucleic acid molecule of claim 1.

6. An isolated host cell, comprising the vector of claim 5.

7. The host cell of claim 6 that is a eukaryotic cell.

8. The host cell of claim 6 tat is a prokaryotic cell.

9. A process of producing a CHL polypeptide comprising culturing the host cell of claim 6 under suitable conditions to express the polypeptide, wherein said polypeptide is produced, and optionally isolating the polypeptide from the culture.

10. The process of claim 9, wherein the nucleic acid molecule comprises promoter DNA other than the promoter DNA for the native polypeptide of SEQ ID NO:12 operatively linked to the DNA encoding SEQ ID NO:12.

11. A composition, comprising a nucleic acid molecule of any of claims 1, 2, 3, or 4 and a pharmaceutically acceptable formulation agent.

12. A viral vector, comprising a nucleic acid molecule of any of claims 1, 2, 3, or 4.

* * * * *